US010131870B2

(12) United States Patent
Takeuchi et al.

(10) Patent No.: US 10,131,870 B2
(45) Date of Patent: Nov. 20, 2018

(54) TARGETED MUTAGENESIS IN SPIRULINA

(71) Applicant: Lumen Bioscience, Inc., Seattle, WA (US)

(72) Inventors: Ryo Takeuchi, Seattle, WA (US); James Roberts, Seattle, WA (US)

(73) Assignee: LUMEN BIOSCIENCE, INC., Seattle, WA (US)

( * ) Notice: Subject to any disclaimer, the term of this patent is extended or adjusted under 35 U.S.C. 154(b) by 0 days.

(21) Appl. No.: 15/510,028

(22) PCT Filed: Sep. 9, 2015

(86) PCT No.: PCT/US2015/049214
§ 371 (c)(1),
(2) Date: Mar. 9, 2017

(87) PCT Pub. No.: WO2016/040499
PCT Pub. Date: Mar. 17, 2016

(65) Prior Publication Data
US 2017/0298319 A1    Oct. 19, 2017

Related U.S. Application Data

(60) Provisional application No. 62/047,811, filed on Sep. 9, 2014.

(51) Int. Cl.
| | |
|---|---|
| C12N 1/13 | (2006.01) |
| C12N 1/20 | (2006.01) |
| C12N 15/74 | (2006.01) |
| C12N 15/90 | (2006.01) |
| C07K 14/195 | (2006.01) |
| C12N 13/00 | (2006.01) |

(52) U.S. Cl.
CPC ............ *C12N 1/20* (2013.01); *C07K 14/195* (2013.01); *C12N 13/00* (2013.01); *C12N 15/74* (2013.01); *C12N 15/902* (2013.01)

(58) Field of Classification Search
None
See application file for complete search history.

(56) References Cited

U.S. PATENT DOCUMENTS

| | | | |
|---|---|---|---|
| 6,528,314 | B1 | 3/2003 | Le Mouellic et al. |
| 2010/0081178 | A1 | 4/2010 | Roberts et al. |
| 2010/0184169 | A1 | 7/2010 | Roberts et al. |
| 2013/0344549 | A1 | 12/2013 | Roberts et al. |
| 2014/0004580 | A1 | 1/2014 | Roberts et al. |
| 2015/0329868 | A1 | 11/2015 | Hickman et al. |
| 2016/0046902 | A1 | 2/2016 | Roberts et al. |
| 2017/0298319 | A1 | 10/2017 | Takeuchi et al. |

FOREIGN PATENT DOCUMENTS

| | | |
|---|---|---|
| CN | 1528902 | 9/2004 |
| JP | 06-253863 | 9/1994 |
| WO | WO-2009/098089 A2 | 8/2009 |
| WO | WO-2010/048568 | 4/2010 |
| WO | WO-2010/075440 | 7/2010 |
| WO | WO-2012/087963 | 6/2012 |
| WO | WO-2012/087982 | 6/2012 |
| WO | WO-2013/116517 | 8/2013 |
| WO | WO-2014/164232 | 10/2014 |
| WO | WO-2014/164566 | 10/2014 |

OTHER PUBLICATIONS

Ballicora et al, "ADP-Glucose Pyrophosphorylase, a Regulatory Enzyme for Bacterial Glycogen Synthesis", Microbiology and Molecular Biology Reviews, Jun. 2003, vol. 67, No. 2, 14 pgs.
Buschiazzo et al, "Crystal structure of Glycogen Synthase: Homologous Enzymes Catalyze Glycogen Synthesis and Degradation", The EMBO Journal, Jul. 2004, vol. 23, No. 16, 10 pgs.
Cao, et al., "Breeding and Characterization of Amino Acid-Analogue-Resistant Mutants of Arthrospira Platensis", World Journal of Microbiology and Biotechnology, Rapid Communications of Oxford, GB, vol. 30, No. 2, Aug. 24, 2013, pp. 423-428.
Coates et al. "Characterization of Cyanobacterial Hydrocarbon Composition and Distribution of Biosynthetic Pathways", PLOS one, vol. 9, Jan. 2014, pp. 1-12.
Deveraux et al., "A comprehensive set of sequence analysis programs for the VAX", Jan. 1984, Nucleic Acids Research 12, 387-395.
Ducat et al. "Engineering Cyanobacteria to Generate High Value Products", Review, Special Issue—Applied Microbiology, Trends in Biotechnology, Feb. 2011, vol. 29, No. 2, 9 pgs.
Fang et al, "Rapid Mutation of *Spirulina platensis* by a New Mutagenesis System of Atmospheric and Room Temperature Plasmas (ARTP) and Generation of a Mutant Library with Diverse Phenotypes", PLoS ONE, vol. 8, Issue 10, Oct. 2013, 12 pgs.
Fujisawa et al, "Genomic Structure of an Economically Important Cyanobacterium, Arthrospira (*Spirulina*) Platensis NIES-39", DNA Research 17, Advance Access Publication Mar. 2010, pp. 85-103.
Gibson et al, "Enzymatic Assembly of DNA Molecules up to Several Hundred Kilobases", Nature Methods, May 2009, vol. 6, No. 5, 5 pgs.
Gribskov, "Sigma factors from *E. coli, B. subtilis*, phage SP01, and phage T4 are homologous proteins", Aug. 1986, Acids Res. vol. 14, No. 6, pp. 6745-6763.
Guiry, M.D. & Guiry, G.M., 2014, AlgaeBase. World-wide electronic publication, National University of Ireland, Galway. http://www.algaebase.org; searched on Aug. 25, 2014, 1 pg.
Hofvander et al, "A Prokaryotic Acyl-CoA Reductase Performing Reduction of Fatty Acyl-CoA to Fatty Alcohol", FEBS letters 585, Oct. 2011, pp. 3538-3543.
Jin et al, "Crystal Structure of Potato Tuber ADP-Glucose Pyrophosphorylase", The EMBO Journal, Feb. 2005, vol. 24, No. 4, 11 pgs.
Kawata et al, "Transformation of *Spirulina platensis* Strain C1 (*Arthrospira* sp. PCC9438) with Tn5 Transposase Transposon DNA Cation Liposome Complex", Marine Biotechnology, May 2004, 9 pgs.
Lu et al, "Molecular Cloning and Characterization of the pgm Gene Encoding Phosphoglucomutase of *Escherichia coli*", Journal of Bacteriology, Sep. 1994, vol. 176, No. 18, 6 pgs.

(Continued)

*Primary Examiner* — James S Ketter
(74) *Attorney, Agent, or Firm* — Cooley LLP

(57) ABSTRACT

This disclosure describes techniques for creating stable, targeted mutations in *Spirulina* (*Athrospiria*) and *Spirulina* having stable, targeted mutations.

26 Claims, 9 Drawing Sheets

Specification includes a Sequence Listing.

(56) References Cited

OTHER PUBLICATIONS

Makino et al, "Characterization of Cyanobacterial Carotenoid Ketolase CrtW anad Hydroxylase CrtR by Complementation Analysis in *Escherichia coli*", Pant Cell Physiology, Oct. 2008, vol. 49, No. 12, 12 pgs.

The PCT Search Report and Written Opinion dated Dec. 7, 2015 for PCT application No. PCT/US2015/049214, 18 page.

Smith et al, "Comparison of Biosequences", Advanced in Applied Mathematics, vol. 2, Issue 4, Dec. 1981, pp. 482-489.

Toyomizu et al, "Effective Transformation of the Cyanobacterium *Spirulina platensis* using Electroporation", Journal of Applied Phycology, Jun. 2001, vol. 13, Issue 3, 6 pgs.

Van Heeke et al, "Expression of Human Asparagine Synthetase in *Escherichia coli*", The Journal of Biological Chemistry, vol. 264, No. 10, Apr. 1989, 7 pgs.

Yoskikawa, et al., "Single-Laboratory Validation of a Method for the Determination of C-Phycocyanin and Allophycocyanin in *Spirulina* (Arthrospira) Supplements and Raw Materials by Spectrophotometry", J. AOAC Int., 2008, vol. 91 (3), pp. 524-529.

Zhang, et al., "Preliminary Studies on the Genetic Transformation of Spirulina Platensis", Algae and their Biotechnological Potential, Proceedings of the 4th Asia-Pacific Conference on Algal Biotechnology, Jul. 3-6, 2000, in Hong Kong, Springer, NL, Jan. 1, 2011, pp. 263-269.

Toyomizu et al., "Effective transformation of the cyanobacterium *Spirulina platensis* using electroporation," Journal of Applied Phycology 13:209-214 (2001).

Zhang et al., "Preliminary Studies on the Genetic Transformation of *Spirulina platensis*," Algae and Their Biotechnological Potential, 2001, pp. 263-269 (2001).

International Preliminary Report on Patentability issued by the International Searching Authority for Application No. PCT/US2015/049214, dated Mar. 14, 2017, 10 pages.

Ducat, et al. "Engineering cyanobacteria to generate high-value products," Trends Biotechnol. 29(2):95-103 (2011).

Jeamton, et al., "Overcoming Intrinsic Restriction Enzyme Barriers Enhances Transformation Efficiency in Arthrospira platensis C1," Plant Cell Physiol. 58(4): 822-830 (2017).

Kawata et al., "Transformation of *Spirulina platensis* by chromosomal integration," Algal Biotechnology, Ceske Budejovice, Czech Republic Sep. 6-11, 1993 : Progress in Biotechnology of Photoautotrophic Microorganisms : 6th International Conference on Applied Algology : Book of Abstracts, Department of Autotrophic Microorganisms,Jan. 1, 1993 (Jan. 1, 1993), p. 72, XP008178083,abstract.

Klanchui, et al., "Systems biology and metabolic engineering of Arthrospira cell Factories," Comput Struct Biotechnol J. 3(4):e201210015 (2012), 8 pages.

TARGETED MUTAGENESIS IN SPIRULINA

PRIORITY CLAIM

This application is a national stage application of international patent application No. PCT/US15/49214, entitled "Targeted Mutagenesis In *Spirulina*," and filed Sep. 9, 2015, which claims priority to U.S. Provisional Patent Application No. 62/047,811, entitled "Targeted Mutagenesis in *Spirulina*," and filed Sep. 9, 2014. PCT International Application No. PCT/US15/49214 and U.S. Provisional Application Ser. No. 62/047,811 are fully incorporated herein by reference.

SEQUENCE LISTING

The Sequence Listing associated with this application is provided in text format in lieu of a paper copy, and is hereby incorporated by reference into the specification. The name of the text file containing the Sequence Listing is M077-0017PCT_ST25.txt. The text file is about 73 KB, was created on Sep. 9, 2015, and is being submitted electronically via EFS-Web.

BACKGROUND

Cyanobacteria, also called blue-green algae, are photosynthetic organisms that use chlorophyll A and water to reduce carbon dioxide and generate energy-containing compounds. *Spirulina* are free-floating, filamentous cyanobacteria that include the species *Arthrospira platensis* and *Arthrospira maxima*. These two species were formerly classified in the genius *Spirulina*, but are now classified in the genus *Arthrospira*. However, the term "*Spirulina*" remains in use.

Cyanobacteria are generally amenable to genetic manipulation. However, genetic engineering tools for *Spirulina* are limited. Many techniques for genetic manipulation are based on introducing exogenous (foreign) genetic material into a bacterial cell. Cells must be in a state of "competence" to take up genetic material from the surrounding environment. Some types of bacteria are able to naturally take up genetic material. These types of bacteria are referred to as having "natural competence." More commonly, "artificial competence" is induced by making a cell temporarily permeable to genetic material. Techniques for introducing artificial competence by increasing the permeability of an outer cell membrane include incubation in chemical solutions, heat shock, and electroporation which subjects a cell to an electric field. A cell in a state of competence that uptakes exogenous genetic material and incorporates the new genetic material into its genome is said to be have undergone "transformation."

*Spirulina* has been long recognized as difficult to transform by random integration of DNA into a *Spirulina* chromosome, and applicant is not aware of any reports claiming modification of the *Spirulina* genome by targeted introduction of DNA into specific, predetermined chromosome locations. Attempts using electroporation to introduce a gene for chloramphenicol resistance have resulted in chloramphenicol resistance under certain electroporation conditions, but the transformation was not stable (i.e. the chloramphenicol resistance could not be sustained). Subsequent attempts to transform *Spirulina* with a gene for chloramphenicol resistance coupled to a strong promoter by using electroporation achieved cells that grew in the presence of chloramphenicol for 12 months, but the method only allowed the gene for chloramphenicol resistance to be located at random (untargeted) locations in a *Spirulina* chromosome, and even this random integration of exogenous DNA was not conclusively demonstrated. Recently, random mutagenesis has been achieved in *S. platensis* (*A. platensis*) using atmospheric and room-temperature plasma (ARTP). However, random mutagenesis does not transform the *Spirulina* cells through introducing exogenous genetic material, rather mutations are introduced at random sites in the genome. A lack of understanding of how to stably introduce foreign DNA to predetermined chromosome locations into cyanobacteria, *Spirulina* in particular, is recognized as a challenge to working with cyanobacteria as compared to other organisms such as *E. coli* or yeast. Although there was some level of success with random mutagenesis, this research also highlighted the continued lack of an effective system for mutation of *S. plantensis* by introduction and expression an exogenous gene. Moreover, none of the techniques described above have attempted to introduce targeted mutations to specific, pre-determined regions of the *Spirulina* genome.

A need still exists for a technique to efficiently create stable transformants in *Spirulina*. Moreover, there is also a need for techniques that allow for targeted introduction of mutations in the *Spirulina* genome.

BRIEF SUMMARY

This disclosure describes techniques for introducing stable, targeted mutations to the genome of *Spirulina*. This disclosure also describes *Spirulina* modified to contain stable, targeted mutations. Additionally, this disclosure described techniques for using *Spirulina* that have been modified to include one or more stable, targeted mutation to manufacture products of interest.

This disclosure describes methods of creating targeted mutations in *Spirulina* by contacting the *Spirulina* with an osmotic stabilizer, contacting the *Spirulina* with a vector having homology arms, and inducing artificial competence in the *Spirulina*. In an embodiment, the *Spirulina* may be *Athrospiria platensis* NIES-39 or *Arthrospira* sp. PCC 8005. The osmotic stabilizer may be, but is not limited to, polyethylene glycol (PEG), ethylene glycol, glycerol, glucose, sucrose, or any combination thereof. The vector may be a DNA vector, a linear vector, a circular vector, a single stranded polynucleotide, or a double stranded polynucleotide. In an embodiment the vector may be, for example, a pApl-pilA/aadA plasmid.

In an embodiment the homology arms may be the same length. In an embodiment the homology arms may be different lengths. One or both of the homology arms may be at least about 500 bp, at least about 1000 bp, at least about 1500 bp, or at least about 2000 bp.

In an embodiment the artificial competence may be induced by any known technique for introducing artificial competence in prokaryotic cells including incubation in a solution containing divalent cations, electroporation, and ultrasound.

In an embodiment, the method may also include contacting the *Spirulina* with a pH balancer. The *Spirulina* may be contacted by the pH balancer prior to or after contacting the *Spirulina* with the vector. In an embodiment a pH of the *Spirulina* after contacting with the pH balancer is about 7.0 to about 8.0.

This disclosure describes *Spirulina* comprising at least one stable, targeted mutation. In an embodiment the *Spirulina* is *Athrospiria platensis, Athrospiria platensis* NIES-39, or *Arthrospira maxima*. In an embodiment, the stable targeted mutation is inherited for at least 5 generations, at least 10 generations, at least 20 generations, at least 30 generations, at least 40 generations, or at least 50 generations. The mutation may be any type of alteration to the genome including a deletion or disruption of at least a portion of a gene, an insertion of an additional copy of an endogenous gene, or addition of an exogenous gene. In an embodiment, the targeted mutation may include addition of an exogenous protein domain including post-translational modification sites, protein-stabilizing domains, cellular localization signals, and protein-protein interaction domains. In an embodiment, the targeted mutation comprises addition of a nucleic acid sequence that is not translated into a protein including, but not limited to, a non-coding RNA molecule, a gene regulatory element, a promoter, a regulatory protein binding site, a RNA binding site, a ribosome binding site, a transcriptional terminator, or a RNA-stabilizing element.

This disclosure also describes a *Spirulina* cell lacking at least one protein as a result of introducing a modification at the loci of the protein by transformation of the *Spirulina* cell with at least one DNA construct comprising a sequence homologous with at least a portion of the loci and the modification and integration of the DNA construct at the loci, the *Spirulina* cell being otherwise capable of functioning in its native manner.

DETAILED DESCRIPTION

Definitions

Figure 1:
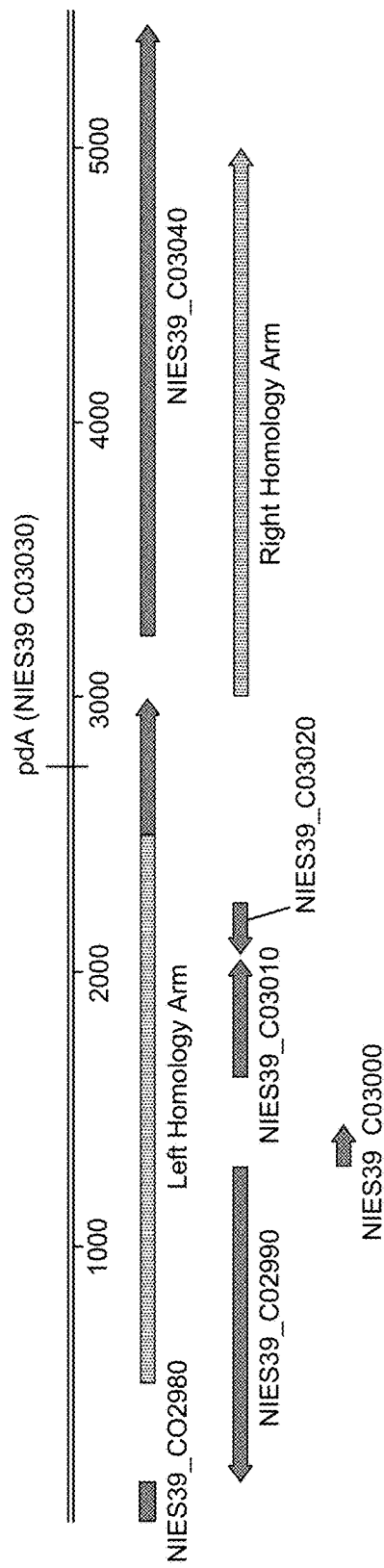
FIG. 1 shows left and right homology arms designed to target the pilA gene locus (NIES39_C03030) in *A. platensis* strain NIES-39.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, illustrative methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

Throughout this specification, unless the context requires otherwise, the words "comprise," "comprises," and "comprising" will be understood to imply the inclusion of a stated step or element or group of steps or elements but not the exclusion of any other step or element or group of steps or elements.

As used herein, the terms "having," "has," "contain," "including," "includes," "include," and "have" have the same open-ended meaning as "comprising," "comprises," and "comprise" provided above.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "about" is meant a quantity, level, value, number, frequency, percentage, dimension, size, amount, weight or length that varies by as much as 30, 25, 20, 15, 10, 9, 8, 7, 6, 5, 4, 3, 2, or 1% to a reference quantity, level, value, number, frequency, percentage, dimension, size, amount, weight, or length.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds) and provided literal support for and includes the end points of 10 and 100.

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. These broad, intermediate, and narrow numerical ranges should be applied not only to the specific values, but should also be applied to differences between these specific values.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences) whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The recitation "polynucleotide" or "nucleic acid" as used herein designates mRNA, RNA, cRNA, rRNA, cDNA, or DNA. The term typically refers to polymeric form of nucleotides of at least 10 bases in length, either ribonucleotides or deoxynucleotides or a modified form of either type of nucleotide. The term includes single and double stranded forms of DNA and RNA.

As used herein, the term "DNA" includes a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

With regard to polynucleotides, the term "exogenous" refers to a polynucleotide sequence that does not naturally occur in a wild-type cell or organism, but is typically introduced into the cell by molecular biological techniques. Examples of exogenous polynucleotides include vectors, plasmids, and/or man-made nucleic acid constructs encoding a desired protein. With regard to polynucleotides, the term "endogenous" or "native" refers to naturally occurring polynucleotide sequences that may be found in a given wild-type cell or organism. A vector, plasmid, or other man-made construct that includes an endogenous polynucleotide sequence combined with polynucleotide sequences of the unmodified vector etc. is, as a whole, an exogenous polynucleotide and may also be referred to as an exogenous polynucleotide including an endogenous polynucleotide sequence. Also, a particular polynucleotide sequence that is isolated from a first organism and transferred to second organism by molecular biological techniques is typically considered an "exogenous" polynucleotide with respect to the second organism.

Polynucleotides may comprise a native sequence (e.g., an endogenous sequence that encodes protein described herein) or may comprise a variant or fragment, or a biological functional equivalent of such a sequence. Polynucleotide variants may contain one or more substitutions, additions, deletions and/or insertions, as further described herein, preferably such that the enzymatic activity of the encoded polypeptide is not substantially diminished relative to the unmodified or reference polypeptide. The effect on the enzymatic activity of the encoded polypeptide may generally be assessed as described herein and known in the art.

As will be understood by those skilled in the art, the polynucleotide sequences of this disclosure can include genomic sequences, extra-genomic, and plasmid-encoded sequences and smaller engineered gene segments that express, or may be adapted to express, proteins, polypeptides, peptides and the like. Such segments may be naturally isolated, or modified synthetically by the hand of man.

Polynucleotides may be single-stranded (coding or antisense) or double-stranded, and may be DNA (genomic, cDNA, or synthetic) or RNA molecules. Additional coding or non-coding sequences may, but need not, be present within a polynucleotide of the present invention, and a polynucleotide may, but need not, be linked to other molecules and/or support materials.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

The percent identity of two sequences, whether nucleic acid or amino acid sequences, is the number of exact matches between two aligned sequences divided by the length of the shorter sequences and multiplied by 100. An approximate alignment for nucleic acid sequences is provided by the Smith-Waterman algorithm. The Smith-Waterman algorithm can be applied to amino acid sequences by using a known scoring matrix (e.g., the scoring matrix developed by Dayhoff) and normalized by any well-known technique such as the Gribskov method. One implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Other suitable programs for calculating the percent identity or similarity between sequences are generally known in the art, for example, the MPSRCH package of programs copyrighted by the University of Edinburgh, developed by John F. Collins and Shane S. Sturrok, and distributed by IntelliGenetics, Inc. (Mountain View, Calif.), and BLAST, used with default parameters. Details of these programs can be found at the following internet address: http://blast.ncbi.nlm.nih.gov/Blast.cgi.

"Polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions. Exemplary nucleotide sequences that encode the proteins and enzymes of the application encompass full-length reference polynucleotides, as well as portions of the full-length or substantially full-length nucleotide sequences of these genes or their transcripts or DNA copies of these transcripts. Portions of a nucleotide sequence may encode polypeptide portions or segments that retain the biological activity of the reference polypeptide.

"Transformation" refers to the stable, heritable alteration in a cell resulting from the uptake and incorporation of exogenous nucleotides into the host-cell genome; also, the transfer of an exogenous gene from one organism into the genome of another organism. Exogenous nucleotides may include gene foreign to the target organism or addition of a nucleotide sequence present in the wild-type organism.

"Targeted mutation" means a change in the DNA sequence of the genome at a pre-determined (specified) genome location. In some cases a targeted mutation will involve the introduction of a pre-determined (specified) DNA sequence alteration at the pre-determined genome location. In other cases a targeted mutation will involve the introduction of a random DNA sequence alteration at the pre-determined genome location.

"Stable" when describing the results of a genetic modification caused by transformation refers to a genetic modification that is maintained in at least a portion of a population of cells for ten or more generations or for a length of time equal or greater to ten times the average generation time for the modified organism.

"Competent" refers to the ability of a cell to take up extracellular nucleotides from the surrounding environment. A cell may be "naturally competent" or "artificially competent." Naturally competent cells are able to take up nucleotides from their surrounding environment under natural conditions. Artificially competent cells are made passively permeable to extracellular nucleotides by exposing the cell to conditions that do not normally occur naturally including incubation in a solution of divalent cations, heat shock, electroporation, and ultrasound.

The terms "wild-type" and "naturally occurring" are used interchangeably to refer to an organism, gene, or gene product that has the characteristics of that organism, gene or gene product (e.g., a polypeptide) when isolated from a naturally occurring source. A wild-type organism, gene, or gene product is that which is most frequently observed in a population and is thus arbitrarily designed the "normal" or "wild-type" form.

As used herein "Spirulina" is synonymous with "Arthrospira." The genus Arthrospria includes 57 species of which 22 are currently taxonomically accepted. Thus, reference to "Spirulina" or "Arthrospira" without further designation includes reference to any of the following species: A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana var. crassa, A. indica, A. jenneri var. platensis, A. jenneri Stizenberger, A. jennerif. purpurea, A. joshii, A. khannae, A. laxa, A. laxissima, A. laxissima, A. leopoliensis, A. major, A. margaritae, A. massartii, A. massartii var. indica, A. maxima, A. meneghiniana, A. miniata var. constricta, A. miniata, A. miniata f. acutissima, A. neapolitana, A. nordstedtii, A. oceanica, A. okensis, A. pellucida, A. platensis, A. platensis var. non-constricta, A. platensis f. granulate, A. platensis f. minor, A. platensis var. tenuis, A. santannae, A. setchellii, A. skujae, A. spirulinoides f. tenuis, A. spirulinoides, A. subsalsa, A. subtilissima, A. tenuis, A. tenuissima, and A. versicolor.

All literature and similar materials cited in this application, including patents, patent applications, articles, books, treatises, and Internet web pages are expressly incorporated by reference in their entirety for any purpose. When definitions of terms in incorporated references appear to differ from the definitions provided in this application, the definition provided in this application shall control.

Targeted Mutations in Spirulina

In an aspect of the invention, a vector having homology arms is taken up by a Spirulina cell in a state of competence and subsequently integrated into one or more chromosomes of the cell. Homologous recombination guided by the sequences of the homology arms changes the genome of the cell due to differences between the original nucleic acid sequence of the genome and the nucleic acid sequence of the vector region between the homology arms.

The present disclosure describes the first technique known to the inventors for inducing competence in Spirulina. Spirulina is not naturally competent and the techniques disclosed herein achieve a transformation where previous techniques for transforming Spirulina have failed. The high levels of endonucleases present in Spirulina have been previously thought to make transformation impossible. Electroporation has been limited to creating competent cells for only brief periods of time due to the tendency of Spirulina cells to lyse when subjected to electroporation. However, transformation by electroporation in the presence of an appropriate osmotic stabilizer achieves transformation that was previously not possible by other techniques.

Prior to transformation, Spirulina may be cultured and washed with an osmotic stabilizer. Spirulina may be cultured in any suitable media for growth of cyanobacteria such as SOT medium. SOT medium includes $NaHCO_3$ 1.68 g, $K_2HPO_4$ 50 mg, $NaNO_3$ 250 mg, $K_2SO_4$ 100 mg, NaCl 100 mg, $MgSO_4 \cdot 7H_2O$, 20 mg, $CaCl_2 \cdot 2H_2O$ 4 mg, $FeSO_4 \cdot 7H_2O$ 1 mg, $Na_2EDTA \cdot 2H_2O$ 8 mg, $A_5$ solution 0.1 mL, and distilled water 99.9 mL. $A_5$ solution includes $H_3BO_3$ 286 mg, $MnSO_4 \cdot 5H_2O$) 217 mg, $ZnSO_4 \cdot 7H_2O$ 22.2 mg, $CuSO_4 \cdot 5H_2O$ 7.9 mg, $Na2MoO_4 \cdot 2H_2O$ 2.1 mg, and distilled water 100 mL. Cultivation may occur with shaking (e.g., 100-300 rpm) at a temperature higher than room temperature (e.g. 25-37° C.) and under continuous illumination (e.g. 20-2,000, 50-500, or 100-200 µmol photon $m^{-2}$ $s^{-1}$). The growing cells may be harvested when the optical density at 750 nm reaches a predetermined threshold (e.g., $OD_{750}$ of 0.3-2.0, 0.5-1.0, or 0.6-0.8). A volume of the harvested cells may be concentrated by centrifugation then resuspended in a solution of pH balancer and salt. The pH balancer may be any suitable buffer that maintains viability of *Spirulina* while keeping pH of the media between 6 and 9 pH, between 6.5 and 8.5 pH, or between 7 and 8 pH. Suitable pH balancers include HEPES, HEPES-NaOH, sodium or potassium phosphate buffer, and TES. The salt solution may be NaCl at a concentration of between 50 mM and 500 mM, between 100 mM and 400 mM, or between 200 mM and 300 mM. In an embodiment between 1-50 mL of 1-100 mM pH balance may be used to neutralize the pH.

Cells collected by centrifugation may be washed with an osmotic stabilizer and optionally a salt solution (e.g. 1-50 mL of 0.1-100 mM NaCl). Any amount of the culture may be concentrated by centrifugation. In an embodiment between 5-500 mL of the culture may be centrifuged. The osmotic stabilizer may be any type of osmotic balancer that stabilizes cell integrity of *Spriulina* during electroporation. In an embodiment, the osmotic stabilizer may be a sugar (e.g. w/v 0.1-25%) such as glucose or sucrose. In an embodiment the osmotic stabilizer may be a simple polyol (e.g. v/v 1-25%) including glycerine, glycerin, or glycerol. In an embodiment the osmotic stabilizer may be a polyether including (e.g. w/v 0.1-20%) polyethylene glycol (PEG), poly(oxyethylene), or poly(ethylene oxide) (PEO). The PEG or PEO may have any molecular weight from 200 to 10,000, from 1000 to 6000, or from 2000 to 4000. In an embodiment the pH balancer or buffer may be used instead of or in addition to the osmotic stabilizer.

The present disclosure also describes creation of targeted mutations in *Spirulina* through homologous recombination by introduction of a vector to competent cells. Artificial competency may be created by the electroporation technique described above or by any other known or future technique for creating competency in *Spirulina*. Known techniques for introducing artificial competence in *Spirulina* include electroporation (with or without an osmotic stabilizer and with or without a pH balancer), incubation in a solution containing divalent cations, and ultrasound. The *Spirulina* cells are contacted by a vector when artificial competency is induced. For example, a vector may be mixed with a solution of *Spirulina* cells prior to electroporation.

Electroporation may be performed in a 0.1-, 0.2- or 0.4-cm electroporation cuvette at between 0.6 and 10 kV/cm, between 2.5 and 6.5 kV/cm, or between 4.0 and 5.0 kV/cm; between 1 and 100 µF, between 30 and 70 µF, or between 45 and 55 µF; and between 10 and 500 mΩ, between 50 and 250 mΩ, or between 90 and 110 mΩ. In an embodiment electroporation may be performed at 4.5 kV/cm, 50 µf, and 100 mΩ.

Following electroporation the cells may be grown in the presence of one or more antibiotics selected based on resistance conferred through successful transformation with the plasmid. Post-electroporation culturing may be performed at reduced illumination levels (e.g. 5-500, 10-100, or 30-60 µmol photon $m^{-2}$ $s^{-1}$). The culturing may also be performed with shaking (e.g. 100-300 rpm). The level of antibiotics in the media may be between 5 and 100 µg/mL. Post-electroporation culturing may be continued for 1-5 days or longer. Successful transformants identified by antibiotic resistance may be selected over a time course of 1 week to 1 month on plates or in 5-100 mL of SOT medium supplemented with 0.1-2.0 µg of appropriate antibiotics.

By "vector" is meant a polynucleotide molecule, preferably a DNA molecule derived, for example, from a plasmid, bacteriophage, yeast, or virus, into which a polynucleotide can be inserted or cloned. A vector may contain one or more synthetic nucleotides or nucleic acid analogues. A vector may contain one or more unique restriction sites. The vector can be one which, when introduced into the host cell, is integrated into the genome and replicated together with the chromosome(s) into which it has been integrated. Such a vector may comprise one or more specific sequences that allow recombination into a particular, desired site of the host chromosome. These specific sequences may be homologous to sequences present in the wild-type genome. A vector system can comprise a single vector or plasmid, two or more vectors or plasmids, some of which increase the efficiency of targeted mutagenesis, or a transposition. The choice of the vector will typically depend on the compatibility of the vector with the host cell into which the vector is to be introduced. The vector can include a reporter gene, such as a green fluorescent protein (GFP), which can be either fused in frame to one or more of the encoded polypeptides, or expressed separately. The vector can also include a positive selection marker such as an antibiotic resistance gene that can be used for selection of suitable transformants. The vector can also include a negative selection marker such as the type II thioesterase (tesA) gene or the *Bacillus subtilis* structural gene (sacB). Use of a reporter or marker allows for identification of those cells that have been successfully transformed with the vector.

In an embodiment, the vector includes one or two homology arms that are homologous to DNA sequences of the *Spirulina* genome which are adjacent to the targeted locus. The sequence of the homology arms may be identical or similar to the regions of the *Spirulina* genome to which the homology arms are complementary. "Homology" or "homologous" as used herein includes both homologous, identical sequences and homologous, non-identical sequences. Homologous non-identical sequences refer to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. As used herein, the degree of homology between the two homologous, non-identical sequences is sufficient to allow homologous recombination there between, utilizing normal cellular mechanisms. Two homologous non-identical sequences can be any length and their degree of non-homology can be as small as a single nucleotide (e.g., for a genomic point mutation introduced targeted homologous recombination) or as large as 10 or more kilobases (e.g., for insertion of a gene at a predetermined locus in a chromosome). Two polynucleotides comprising homologous non-identical sequences need not be the same length. For example, an exogenous polynucleotide (i.e., vector polynucleotide) of between 20 and 10,000 nucleotides or nucleotide pairs can be used.

The characterization of two sequences as homologous, identical sequences or homologous, non-identical sequences may be determined by comparing the percent identity between the two sequences (polynucleotide or amino acid). Homologous, identical sequences have 100% sequence identity. Homologous, non-identical sequences may have sequence identity greater than 80%, greater than 85%, greater than 90%, greater than 91%, greater than 92%, greater than 93%, greater than 94%, greater than 95%, greater than 96%, greater than 97%, greater than 98%, or greater than 99%.

The homology arms may be any length that allows for site-specific homologous recombination. A homology arm may be any length between about 2000 bp and 500 bp including all integer values between. For example, a homology arm may be about 2000 bp, about 1500 bp, about 1000 bp, or about 500 bp. In embodiments having two homology arms the homology arms may be the same or different length. Thus, each of the two homology arms may be any length between about 2000 bp and 500 bp including all integer values between. For example each of the two homology arms may be about 2000 bp, about 1500 bp, about 1000 bp, or about 500 bp.

A portion of the vector adjacent to one or both (i.e., between) homology arms modifies the targeted locus in the *Spirulina* genome by homologous recombination. Techniques for homologous recombination in other organisms are generally known (see, e.g., Kriegler, 1990, *Gene transfer and expression: a laboratory manual*, Stockton Press). The modification may change a length of the targeted locus including a deletion of nucleotides or addition of nucleotides. The addition or deletion may be of any length. The modification may also change a sequence of the nucleotides in the targeted locus without changing the length. The targeted locus may be any portion of the *Spirulina* genome including coding regions, non-coding regions, and regulatory sequences. In an embodiment the mutation may delete a gene thereby creating a knock-out organism. In an embodiment the mutation may add a gene that functions as a reporter or marker (e.g., GFP or antibiotic resistance). In an embodiment the mutation may add an exogenous gene. In an embodiment the mutation may add an endogenous gene under control of an exogenous promoter (e.g., strong promoter, inducible promoter, etc.).

A vector for use in the targeted mutagenesis described above may be produced by assembling a vector backbone with an insert sequence. The vector may be created by any known or later developed technique including restriction enzyme digest followed by ligation or Gibson assembly. Gibson assembly may be performed by combining DNA sequences that will become portions of vector backbone with an exonuclease, DNA polymerase, and DNA ligase then incubating at 50° C. for one hour. The vector backbone may be selected for compatibility with the target organism. For *Spirulina*, suitable vector backbones include, but are not limited to DNA plasmids. The vector backbone may be converted from a continuous loop to a linear form by treatment with an appropriate restriction endonuclease. The ends thereby formed are treated with alkaline phosphatase to remove 5'-phosphate end groups so that the vector may not reform a continuous loop in a DNA ligase reaction without first incorporating an insert segment.

The insert sequence includes one or two homology arms and a nucleotide sequence that, due to differences between the nucleotide sequences of the insert and the wild-type genome sequence of the *Spirulina*, modify a locus of the *Spirulina*. The insert sequence includes the one or two flanking regions adjacent to the locus of interest that correspond to the homology arms which are homologous to regions of the *Spirulina* genome and a portion that is different from the *Spirulina* genome. The portion of the insert sequence that differs from the wild-type nucleotide sequence of the *Spirulina* leads to modification of the *Spirulina* genome due to those differences. The modification may include, but is not limited to, a point mutation, addition of a gene, addition of a regulatory element, addition of a coding region, addition of a non-coding region, deletion of a gene, deletion of a portion of a gene, or deletion of a regulatory element. Generally, it is well-known that strong *E. coli* promoters work well in Cyanobacteria. If the sequence of the target organism is known, a published sequence may be used to design the insert sequence with homology arm(s). Several strains of *Spirulina* have been sequenced such as *Athrospira plantensis* NIES-39. If the sequence is not known a portion of the genome containing the loci of interest may be amplified using PCR and suitable primers. This region may be subsequently sequenced using techniques known to one skilled in the art. In an embodiment an amplified region of the genome may be used to carry out overlap extension PCR to create a deletion. In an embodiment an amplified region of the genome may be digested with a restriction endonuclease that cuts the nucleotide sequence in one place and ligated to an insert nucleotide sequence that has be prepared with compatible ends.

The insert sequence is digested with one or more restriction endonucleases to create ends that are compatible with the ends of the vector backbone. Alternatively, short sequences (e.g., 16-25 bp) that are identical to the terminal regions of the vector backbone are added to the ends of the insert sequence, and these two fragments are circularized by the Gibson assembly method. The length of the insert sequence will be the length of the modifications to the loci of interest and the length of the flanking regions. For example, if the length of the modified sequence is 500 bp and two homology arms each of 2000 bp are desired, then the entire length of the sequence will be 4500 bp. The polynucleotides sequences used as vectors in the present invention, regardless of the length of the coding sequence itself, may be combined with other sequences, such as promoters, transcriptional terminators, additional restriction enzyme sites, multiple cloning sites, other coding segments, and the like, such that their overall length may vary considerably. It is therefore contemplated that a polynucleotide fragment of almost any length may be employed, with the total length preferably being limited only by the ease of preparation and use in the intended recombinant nucleotide protocol.

Illustrative Applications

Neutral Lipid (Wax Ester and Triglyceride) Production

In an embodiment *Spirulina* may be modified to increase production of neutral lipids, including wax esters and/or triglycerides, beyond the level produced by a wild-type *Spirulina* grown under the same condition. Triglycerides and wax esters may be used as a feedstock in the production of biofuels and/or various specialty chemicals. For example, triglycerides may be subject to a transesterification reaction, in which an alcohol reacts with triglyceride oils, such as those contained in vegetable oils, animal fats, recycled greases, to produce biodiesels such as fatty acid alkyl esters. Such reactions also produce glycerin as a by-product, which can be purified for use in the pharmaceutical and cosmetic industries. Triglycerides, or triacylglycerols (TAG), consist primarily of glycerol esterified with three fatty acids, and yield more energy upon oxidation than either carbohydrates or proteins. Triglycerides provide an important mechanism of energy storage for most eukaryotic organisms. In mammals, TAGs are synthesized and stored in several cell types, including adipocytes and hepatocytes. In contrast to eukaryotes, the observation of triglyceride production in prokaryotes has been limited to certain actinomycetes, such as members of the genera *Mycobacterium, Nocardia, Rhodococcus*, and *Streptomyces*, in addition to certain members of the genus *Acinetobacter*.

Certain organisms can be utilized as a source of neutral lipids in the production of biofuels. For example, eukaryotic algae naturally produce triglycerides as energy storage molecules, and certain biofuel-related technologies are presently focused on the use of algae as a feedstock for biofuels. Algae are photosynthetic organisms, and the use of triglyceride-producing organisms such as algae provides the ability to produce biodiesel from sunlight, water, $CO_2$, macronutrients, and micronutrients.

Like algae, cyanobacteria species including *Spirulina* may obtain energy from photosynthesis, utilizing chlorophyll A and water to reduce $CO_2$. However, *Spirulina* lacks the essential enzymes involved in neutral lipid synthesis. Addition of exogenous genes to cyanobacteria increases lipid production. The techniques described above may be used to add genes to *Spirulina* through targeted, homologous recombination. Thus, the techniques described in this disclosure provide a way to add genes known to increase triglyceride and wax ester production in cyanobacteria such as genes encoding diacylglycerol acyltransferase (DGAT), phosphatidate phosphatase, acetyl-CoA carboxylase (ACCase), aldehyde forming acyl-ACP reductase (AAR), alcohol forming fatty acyl-CoA reductase and alcohol forming fatty acyl-ACP reductase (FAR). The techniques described above may also be used to add portions of genes or polynucleotide sequences encoding polypeptide sequences that differ from wild-type DGAT, phosphatidate phosphatase, and/or ACCase polynucleotide sequences but that still have DGAT enzymatic activity, phosphatidate phosphatase enzymatic activity, and/or ACCase enzymatic activity.

Acyl ACP Reductases (AARs) catalyze the reduction of acyl-ACP's to acyl aldehydes, also known as fatty aldehydes. These enzymes are also known as Fatty Acyl ACP Reductasts (FARs). Fatty aldehydes can serve as a substrate for fatty alcohol biosynthesis by a FAR or long chain alcohol dehydrogenase (ADH). One example of an acyl-ACP reductase is PCC7942_orf1594 from *S. elongatus*. The family of AAR genes in cyanobacteria (or FAR genes) have been identified using hidden Markov model protein family patterns TIGR045058 (aldehyde forming long chain fatty acyl ACP reductase) and TIGR04059 (long chain fatty aldehyde decarbonylase) from the TIGRRAMs database.

According to one non-limiting theory, certain embodiments may employ AARs in conjuction with FARs or ADHs to increase synthesis of fatty alcohols, which can then be incorporated into wax esters, mainly by the DGAT-expressing (and thus wax ester-producing) photosynthetic microorganisms described herein. Hence, AARs can be used in any of the embodiments described herein, such as those that produce increased levels of free fatty alcohols, where it is desirable to turn these into wax esters. As noted above, these free fatty alcohols can then be esterified to fatty acids (in the form of acyl-ACP) by DGATs to generate wax esters.

Certain embodiments relate to the use of overexpressed AARs to increase synthesis of fatty alcohols, and thereby increase production of wax esters in a wax ester-producing strain (e.g., a DGAT-expressing strain). For instance, certain embodiments may utilize an AAR, in combination with a fatty acyl reductase, and a DGAT. These embodiments may then further utilize an ACP, an ACCase, or both, and/or any of the modifications to glycogen production and storage or glycogen breakdown described herein.

Fatty Acyl Reductases (FAR) catalyze the two step reduction of acyl-ACP's or acyl-COA's to acyl alcohols, also known as fatty alcohols. The first step proceeds via an acyl aldehyde intermediate, which is then converted in a second step to a fatty alcohol. These same enzymes can also directly reduce fatty aldehydes to fatty alcohols (i.e. step two only). In this case they are sometimes referred to as fatty aldehyde reductases. Fatty alcohols can serve as a substrate for wax ester biosynthesis by a DGAT. Many fatty acyl reductases are characterized by three conserved sequence elements. There is an NADPH binding motif, a motif characteristic of the catalytic site of NADP-utilizing enzymes, and a conserved C-terminal domain, referred to as the Male Sterile 2 domain, that is of unknown function.

According to one non-limiting theory, certain embodiments may employ fatty acyl reductases to increase synthesis of fatty alcohols, which can then be incorporated into wax esters, mainly by the DGAT-expressing (and thus wax ester-producing) photosynthetic microorganisms described herein. Hence, fatty acyl reductases can be used in any of the embodiments described herein, such as those that produce increased levels of free fatty alcohols, where it is desirable to turn these into wax esters. As noted above, these free fatty alcohols can then be esterified to fatty acids (in the form of acyl-ACP) by DGATs to generate wax esters.

Certain embodiments relate to the use of overexpressed fatty acyl reductases to increase synthesis of fatty alcohols, and thereby increase production of wax esters in a wax ester-producing strain (e.g., a DGAT-expressing strain). For instance, certain embodiments may utilize a fatty acyl reductase, possibly in combination with an acyl-ACP reductase, and a DGAT. These embodiments may then further utilize an ACP, an ACCase, or both, and/or any of the modifications to glycogen production and storage or glycogen breakdown described herein.

Diacylglycerol acyltransferases (DGATs) are members of the O-acyltransferase superfamily, which esterify either sterols or diacylglycerols in an oleoyl-CoA-dependent manner. DGAT in particular esterifies diacylglycerols, and this esterification represents the final enzymatic step in the production of triacylglycerols in plants, fungi, and mammals. Specifically, DGAT is responsible for transferring an acyl group from acyl-coenzyme-A to the sn-3 position of 1,2-diacylglycerol (DAG) to form triacylglycerol (TAG). The DGAT may be an *Acinetobacter baylii* ADP1 diacylglycerol acyltransferase (AtfA), a *Streptomyces coelicolor* DGAT, *Plesiomonas Shigelloides* DGAT or *Alcanivorax borkumensis* DGAT. Thus, in an embodiment the DGAT protein comprises a sequence set forth in any one of SEQ ID NOs: 5, 6, or 7. SEQ ID NO: 5 is the sequence of *Acinetobacter* DGAT. SEQ ID NO: 6: is the sequence of a *Streptomyces coelicolor* DGAT. SEQ ID NO: 7: is the sequence of *Alcanivorax borkumensis* DGAT. In plants and fungi, DGAT is associated with the membrane and lipid body fractions. In catalyzing TAGs, DGAT contributes mainly to the storage of carbon used as energy reserves. In animals, however, the role of DGAT is more complex. DGAT not only plays a role in lipoprotein assembly and the regulation of plasma triacylglycerol concentration, but participates as well in the regulation of diacylglycerol levels (Biochemistry of Lipids, Lipoproteins and Membranes 171-203). DGAT proteins may utilize a variety of acyl substrates in a host cell, including fatty acyl-CoA and fatty acyl-ACP molecules. In addition, the acyl substrates acted upon by DGAT enzymes may have varying carbon chain lengths and degrees of saturation, although DGAT may demonstrate preferential activity towards certain molecules.

A "phosphatidate phosphatase" gene as used herein includes any polynucleotide sequence encoding amino acids, such as protein, polypeptide or peptide, obtainable from any cell source, which demonstrates the ability to catalyze the dephosphorylation of phosphatidate (PtdOH) under enzyme reactive conditions, yielding diacylglycerol (DAG) and inorganic phosphate, and further includes any naturally-occurring or non-naturally occurring variants of a phosphatidate phosphatase sequence having such ability. Example phosphatidate phosphatase genes include, but are not limited to, yeast phosphatidate phosphatase, including *Saccharomyces cerevisiae* phosphatidate phosphatase (yPah1). The Pah1-encoded PAP1 enzyme is found in the cytosolic and membrane fractions of the cell, and its association with the membrane is peripheral in nature. As expected from the multiple forms of PAP1 that have been purified from yeast, pah1Δ mutants still contain PAP1 activity, indicating the presence of an additional gene or genes encoding enzymes having PAP1 activity. In an embodiment the phosphatidate phosphatase gene (Pah1) comprises a sequence set forth in SEQ ID NO: 8.

As used herein, an "acetyl CoA carboxylase" gene includes any polynucleotide sequence encoding amino acids, such as protein, polypeptide or peptide, obtainable from any cell source, which demonstrates the ability to catalyze the carboxylation of acetyl-CoA to produce malonyl-CoA under enzyme reactive conditions, and further includes any naturally-occurring or non-naturally occurring variants of an acetyl CoA carboxylase sequence having such ability. Acetyl-CoA carboxylase (ACCase) is a biotin-dependent enzyme that catalyzes the irreversible carboxylation of acetyl-CoA to produce malonyl-CoA through its two catalytic activities, biotin carboxylase (BC) and carboxyltransferase (CT). The biotin carboxylase (BC) domain catalyzes the first step of the reaction: the carboxylation of the biotin prosthetic group that is covalently linked to the biotin carboxyl carrier protein (BCCP) domain. In the second step of the reaction, the carboxyltransferase (CT) domain catalyzes the transfer of the carboxyl group from (carboxy) biotin to acetyl-CoA. Formation of malonyl-CoA by acetyl-CoA carboxylase (ACCase) represents the commitment step for fatty acid synthesis, because malonyl-CoA has no metabolic role other than serving as a precursor to fatty acids. Because of this reason, acetyl-CoA carboxylase represents a pivotal enzyme in the synthesis of fatty acids. The ACCase may be a *Saccharomyces cerevisiae* acetyl-CoA carboxylase (yACC1), a *Triticum aestivum* ACCase, or a *Synechococcus* sp. PCC 7002 ACCAse. In an embodiment the ACCase gene comprises a sequence set forth in SEQ ID NO: 9.

Specifically, phosphatidate phosphatase enzymes catalyze the production of diacylglycerol molecules, an immediate pre-cursor to triglycerides, and DGAT enzymes catalyze the final step of triglyceride synthesis by converting the diacylglycerol precursors to triglycerides. Increased intracellular ACCase activity contributes to the increased production of fatty acids because this enzyme catalyzes the "commitment step" of fatty acid synthesis. Specifically, ACCase catalyzes the production of a fatty acid synthesis precursor molecule, malonyl-CoA.

The genes or nucleotides encoding polypeptides with the desired enzymatic activity may be introduced to the *Spirulina* genome by a vector with a nucleotide sequence encoding DGAT, phosphatidate phosphatase, ACCase, or a polynucleotide sequence that has DGAT enzymatic activity, phosphatidate phosphatase enzymatic activity, or ACCase enzymatic activity between homology arms which target a specific locus of the *Spirulina* genome. The vector may be any vector suitable for transformation of *Spirulina* including the vectors described above. The polynucleotides of the vector may be codon-optimized for expression in *Spirulina*. The vector may include a promoter associated with the added gene. The promoter may be an inducible promoter. As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such nucleotides are typically referred to as "codon-optimized."

In an embodiment the specific locus is be a gene that is replaced with the nucleotide sequence of the vector. Regulatory elements such as a promoter associated with the replaced gene may be used to direct transcription of the nucleotide sequence from the vector. In an embodiment the specific locus may be a non-coding region of the *Spirulina* genome. The nucleotide sequence of the vector between the homology arms may include regulatory elements such as a promoter that are introduced into the *Spirulina* genome together with the genes or nucleotides encoding polypeptides with the desired enzymatic activity. Since wild-type *Spirulina* do not typically encode the enzymes necessary for triglyceride synthesis the techniques described in this disclosure provide a way to add exogenous genes having DGAT activity, phosphatidate phosphatase activity, and/or ACCase enzymatic activity to *Spirulina* in order to increase lipid production.

Reduced Glycogen Production

In an embodiment *Spirulina* may be modified to accumulate a reduced amount of glycogen as compared to a wild-type *Spirulina* grown under the same conditions. By reducing the amount of glycogen produced, carbon assimilated by Cyanobacteria is directed to the synthesis of other carbon-based products such as lipids and/or fatty acids. Deletion of glycogen biosynthesis genes in cyanobacteria decrease glycogen accumulation.

By blocking, disrupting, or down-regulating the natural glycogen synthesis and storage pathway, e.g., by gene mutation or deletion, in Cyanobacteria the resulting strains of photosynthetic microorganisms increase carbon flow into other biosynthetic pathways. Examples of other biosynthetic pathways include existing pathways, such as existing lipid biosynthetic pathways, or pathways that are introduced through genetic engineering, such as fatty acid or triglyceride biosynthesis pathways. This modification of deleting a gene associated with glycogen synthesis may be combined with the modification described above to add exogenous genes associated triglyceride synthesis. The techniques described above may be used to delete all or a portion of one or more genes associated with the glycogen synthesis and/or storage pathway in *Spirulina* including glucose-1-phosphate adenyltransferase (glgC) genes, phosphoglucomutase (pgm) genes, or a glycogen synthase (glgA) genes. Deletions of a portion of a glucose-1-phosphate adenyltransferase (glgC) gene, a phosphoglucomutase (pgm) gene, or a glycogen synthase (glgA) gene that renders the resulting polypeptide without or with a reduced level of enzymatic activity are also contemplated. Decreased glycogen synthesis and/or accumulation may be more pronounced in *Spriulina* grown under stress conditions such as reduced nitrogen.

Glycogen is a polysaccharide of glucose, which functions as a means of carbon and energy storage in most cells, including animal and bacterial cells. More specifically, glycogen is a very large branched glucose homopolymer containing about 90% α-1,4-glucosidic linkages and 10% α-1,6 linkages. For bacteria in particular, the biosynthesis and storage of glycogen in the form of α-1,4-polyglucans represents an important strategy to cope with transient starvation conditions in the environment.

Glycogen biosynthesis involves the action of several enzymes. For instance, bacterial glycogen biosynthesis occurs generally through the following general steps: (1)

formation of glucose-1-phosphate, catalyzed by phosphoglucomutase (Pgm), followed by (2) ADP-glucose synthesis from ATP and glucose 1-phosphate, catalyzed by glucose-1-phosphate adenylyltransferase (GlgC), followed by (3) transfer of the glucosyl moiety from ADP-glucose to a pre-existing α-1,4 glucan primer, catalyzed by glycogen synthase (GlgA). This latter step of glycogen synthesis typically occurs by utilizing ADP-glucose as the glucosyl donor for elongation of the α-1,4-glucosidic chain.

In bacteria, the main regulatory step in glycogen synthesis takes place at the level of ADP-glucose synthesis, or step (2) above, the reaction catalyzed by glucose-1-phosphate adenylyltransferase (GlgC), also known as ADP-glucose pyrophosphorylase. In contrast, the main regulatory step in mammalian glycogen synthesis occurs at the level of glycogen synthase. As shown herein, by altering the regulatory and/or other active components in the glycogen synthesis pathway of photosynthetic microorganisms such as Cyanobacteria, and thereby reducing the biosynthesis and storage of glycogen, the carbon that would have otherwise been stored as glycogen can be utilized to synthesize other carbon-based storage molecules, such as lipids, fatty acids, and triglycerides.

In an embodiment, a Spirulina, expresses a reduced amount of the phosphoglucomutase gene. In particular embodiments, it may comprise a mutation or deletion in the phosphoglucomutase gene, including any of its regulatory elements (e.g., promoters, enhancers, transcription factors, positive or negative regulatory proteins, etc.). Phosphoglucomutase (Pgm), encoded by the gene pgm, catalyzes the reversible transformation of glucose 1-phosphate into glucose 6-phosphate, typically via the enzyme-bound intermediate, glucose 1,6-biphosphate. Although this reaction is reversible, the formation of glucose-6-phosphate is markedly favored.

In an embodiment, a modified Spirulina expresses a reduced amount of a glucose-1-phosphate adenylyltransferase (glgC) gene. In certain embodiments, it may comprise a mutation or deletion in the glgC gene, including any of its regulatory elements. The enzyme encoded by the glgC gene (e.g., EC 2.7.7.27) participates generally in starch, glycogen and sucrose metabolism by catalyzing the following chemical reaction:

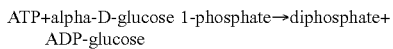
ATP+alpha-D-glucose 1-phosphate→diphosphate+ADP-glucose

Thus, the two substrates of this enzyme are ATP and alpha-D-glucose 1-phosphate, whereas its two products are diphosphate and ADP-glucose. The glgC-encoded enzyme catalyzes the first committed and rate-limiting step in starch biosynthesis in plants and glycogen biosynthesis in bacteria. It is the enzymatic site for regulation of storage polysaccharide accumulation in plants and bacteria, being allosterically activated or inhibited by metabolites of energy flux.

The enzyme encoded by the glgC gene belongs to a family of transferases, specifically those transferases that transfer phosphorus-containing nucleotide groups (i.e., nucleotidyltransferases). The systematic name of this enzyme class is typically referred to as ATP:alpha-D-glucose-1-phosphate adenylyltransferase. Other names in common use include ADP glucose pyrophosphorylase, glucose 1-phosphate adenylyltransferase, adenosine diphosphate glucose pyrophosphorylase, adenosine diphosphoglucose pyrophosphorylase, ADP-glucose pyrophosphorylase, ADP-glucose synthase, ADP-glucose synthetase, ADPG pyrophosphorylase, and ADP:alpha-D-glucose-1-phosphate adenylyltransferase.

In an embodiment, Spirulina expresses a reduced amount of a glycogen synthase gene. In particular embodiments, it may comprise a deletion or mutation in the glycogen synthase gene, including any of its regulatory elements. Glycogen synthase (GlgA), also known as UDP-glucose-glycogen glucosyltransferase, is a glycosyltransferase enzyme that catalyses the reaction of UDP-glucose and (1,4-α-D-glucosyl)$_n$ to yield UDP and (1,4-α-D-glucosyl)$_{n+1}$. Glycogen synthase is an α-retaining glucosyltransferase that uses ADP-glucose to incorporate additional glucose monomers onto the growing glycogen polymer. Essentially, GlgA catalyzes the final step of converting excess glucose residues one by one into a polymeric chain for storage as glycogen.

Classically, glycogen synthases, or α-1,4-glucan synthases, have been divided into two families, animal/fungal glycogen synthases and bacterial/plant starch synthases, according to differences in sequence, sugar donor specificity and regulatory mechanisms. However, detailed sequence analysis, predicted secondary structure comparisons, and threading analysis show that these two families are structurally related and that some domains of animal/fungal synthases were acquired to meet the particular regulatory requirements of those cell types.

Crystal structures have been established for certain bacterial glycogen synthases. These structures show that reported glycogen synthase folds into two Rossmann-fold domains organized as in glycogen phosphorlyase and other glycosyltransferases of the glycosyltransferases superfamily, with a deep fissure between both domains that includes the catalytic center. The core of the N-terminal domain of this glycogen synthase consists of a nine-stranded, predominantly parallel, central β-sheet flanked on both sides by seven α-helices. The C-terminal domain (residues 271-456) shows a similar fold with a six-stranded parallel β-sheet and nine α-helices. The last α-helix of this domain undergoes a kink at position 457-460, with the final 17 residues of the protein (461-477) crossing over to the N-terminal domain and continuing as α-helix, a typical feature of glycosyltransferase enzymes.

These structures also show that the overall fold and the active site architecture of glycogen synthase are remarkably similar to those of glycogen phosphorylase, the latter playing a central role in the mobilization of carbohydrate reserves, indicating a common catalytic mechanism and comparable substrate-binding properties. In contrast to glycogen phosphorylase, however, glycogen synthase has a much wider catalytic cleft, which is predicted to undergo an important interdomain 'closure' movement during the catalytic cycle.

Crystal structures have been established for certain GlgA enzymes. These studies show that the N-terminal catalytic domain of GlgA resembles a dinucleotide-binding Rossmann fold and the C-terminal domain adopts a left-handed parallel beta helix that is involved in cooperative allosteric regulation and a unique oligomerization. Also, communication between the regulator-binding sites and the active site involves several distinct regions of the enzyme, including the N-terminus, the glucose-1-phosphate-binding site, and the ATP-binding site.

The glucose-1-phosphate adenyltransferase (glgC), phosphoglucomutase (pgm), and/or glycogen synthase (glgA) genes may be deleted in whole or part using a vector with homology arms that target the upstream and downstream flanking regions of a given gene and recombines with the Spirulina genome to remove nucleotides in the region between the homology arms or replace nucleotides with a different sequence such as a reporter or marker gene. Given the presence of a reporter or marker in the vector sequence, such as a drug-selectable marker, *Spirulina* cells containing the gene deletion can be readily isolated, identified, and characterized. As one example, selection and isolation may include the use of antibiotic resistant markers known in the art (e.g., kanamycin, spectinomycin, and streptomycin). Such selectable vector-based recombination methods need not be limited to targeting upstream and downstream flanking regions, but may also be targeted to internal sequences within a given gene, as long as that gene is rendered "non-functional." The deletion of all or part of genes that participate in glycogen synthesis does not harm growth of *Spriulina* but reduces production of glycogen.

Modified Carotenoid Production

Carotenoids can be produced from fats and other basic organic metabolic building blocks by Cyanobacteria including *Spirulina*. Carotenoids function in photosynthesis to protect other components of photosynthetic systems from oxidative stress. Carotenoids may also provide various yellow to red shades of pigmentation. Carotenoid biosynthesis in Cyanobacteria can be modified by reducing the expression of certain genes, increasing the expression of certain genes, and/or introducing exogenous genes.

Cyanobacteria which contains deletions of crtG (2,2'(3-carotene hydroxylase) leads to increased synthesis and accumulation of zeaxanthin while maintaining typical rates of exponential growth. Additionally, an expression of crtR (3,3'(3-carotene hydroxylase) or crtZ (cartonenoid-3,3'-hydroxylase) has been demonstrated to lead to production of zeaxanthin in the *E. coli* strain, where a series of genes involved in β-carotene synthesis are introduced, crtE, crtB, crtI and crtY. In an embodiment the crtR gene comprises a sequence set forth in SEQ ID NO: 10. In an embodiment the crtZ gene is from *Brevundimonas* sp. SD212 and comprises a sequence set forth in SEQ ID NO: 11.

Additionally, introduction of crtW (β-carotene oxygenase) and crtZ (cartonenoid-3,3'-hydroxylase) leads to synthesis and accumulation of astaxanthin and canthaxanthin in Cyanobacteria. In an embodiment the crtW gene is from *Brevundimonas* sp. SD212 and comprises a sequence set forth in SEQ ID NO: 12.

The techniques described in this disclosure may be used to knock out or render non-functional *Spirulina* genes in for crtG. Additionally the techniques described in this disclosure may be used to add crtR, crtZ, and crtW genes to the *Spirulina* genome under control of a native *Spirulina* promoter or under control of an exogenous promoter including strong promoters and inducible/repressible promoters. In an embodiment, a promoter regulating expression of crtW and crtZ genes may be a tightly regulated promoter such that in the absence of induction there is no or essentially no expression of the exogenous genes.

For example, to produce carotenoids, a modified *Spirulina* may contain an overexpressed carotenoid hydroxylase (e.g., β-carotene hydroxylase). In these and related embodiments, carotenoid production can be further increased by subjecting the modified photosynthetic microorganism to a stress condition such as, but not limited to, nitrogen deprivation. One illustrative carotenoid hydroxylase is encoded by crtR of *A. plantensis* NIES39_R00430. Another illustrative carotenoid hydroxylase is encoded by crtZ of *Pantoea ananatis*. Also included are homologs or paralogs thereof, functional equivalents thereof, and fragments or variants thereofs. Functional equivalents can include carotenoid hydroxylase with the ability to add hydroxyl groups to β-carotene. These and related embodiments can be further combined with reduced expression and/or activity of an endogenous gylcogen-pathway gene (e.g., glgC in *A. plantensis*), described herein, to shunt carbon away from glycogen production and towards carotenoids.

Modified Phycocyanin and/or Phycoerythrin Production

In an embodiment *Spirulina* may be modified to increase production of phycocyanin and/or phycoerythrin beyond the level produced by a wild-type *Spirulina* grown under the same condition. Phycocyanin and phycoerythrin associated with their bilin chromophores, are natural occurring blue and red pigments, respectively, that are used in the cosmetic, food, and medical imaging industries. These pigment molecules can be purified from cyanobacteria.

One distinguishing feature of many cyanobacteria is a massive light harvesting structure called the phycobilisome. The phycobilisome, which give cyanobacteria their diversity of colors, accounts for up to 60% of the cell's protein. These massive protein structures transfer energy directly to the photosynthetic reaction centers for photochemistry.

The pigment molecules in phycobilisomes that absorb light for photochemistry are linear teterapyrrole molecules called bilins. All bilins are covalently bound through a cysteine thioether linkage to phycobiliproteins. There are three major classes of phycobiliproteins in phycobilisomes; allophycocyanin (AP), phycocyanin (PC) and phycoerythrin (PE). Each class contains a and (3 subunits that form heterodimers. Both the a and (3 subunits of the heterodimer can bind one or more of the bilin pigments.

The major structural components that comprise the phycobilisome can be subdivided into two groups; the "core" substructure and the "rod" substructure. In *Synechococcus* sp. strains, the core substructure consists of two cylinders made of a few types of phycobiliproteins and core linker proteins. The rod substructures are composed of hexamers of the PC a and PC (3 heterodimer. An average of three of these heterohexamers are connected via the linker proteins, and stacked on the core substructure.

The techniques described above may be used to add genes to *Spirulina* through targeted, homologous recombination. The techniques described in this disclosure provide a way to add genes known to encode phycocyanin, or phycoerythrin. The techniques described above may also be used to add portions of genes or polynucleotide sequences encoding polypeptide sequences that differ from wild-type phycocyanin, or phycoerythrin, but that still have the ability to associate with a bilin chromophore.

EXAMPLES

Certain embodiments of the present disclosure now will be illustrated by the following Examples. The present disclosure may, however, be embodied in many different forms and should not be construed as limited to the embodiments set forth herein; rather, these embodiments are provided so that this disclosure will be thorough and complete, and will fully convey the scope of the disclosure to those skilled in the art.

Example 1

*Athrospira plantensis* NIES-39 cells obtained from the Microbial Culture Collection at the National Institute for Environmental Studies (Japan) were cultured in SOT medium with shaking under continuous illumination. When the optical density at 750 nm reached 0.6-0.8, cells were harvested at 1,500×g for 10 min from 60 mL of culture and resuspended in 30 mL of a pH balancer and salt solution. Cells were collected by centrifugation under the same conditions and washed three times with a polyether osmotic stabilizer. The cell suspension was twice diluted in the osmotic stabilizer and then spun down at 1,500×g for 5 min and a total volume of the cell suspension was adjusted to 2 mL.

FIG. 1 shows a targeted gene locus of A. plantensis. This gene locus includes the pilA gene (encoding pili protein). Regions of the A. plantensis genome corresponding to the left homology arm and the right homology arm are also shown. The left homology arm is adjacent to the "left" end (5'-end) of the gene locus of interest and the right homology arm is adjacent to the "right" end (3'-end) of the gene locus of interest. In this example the left homology arm and the right homology arm are about 2000 bp long.

Figure 2:
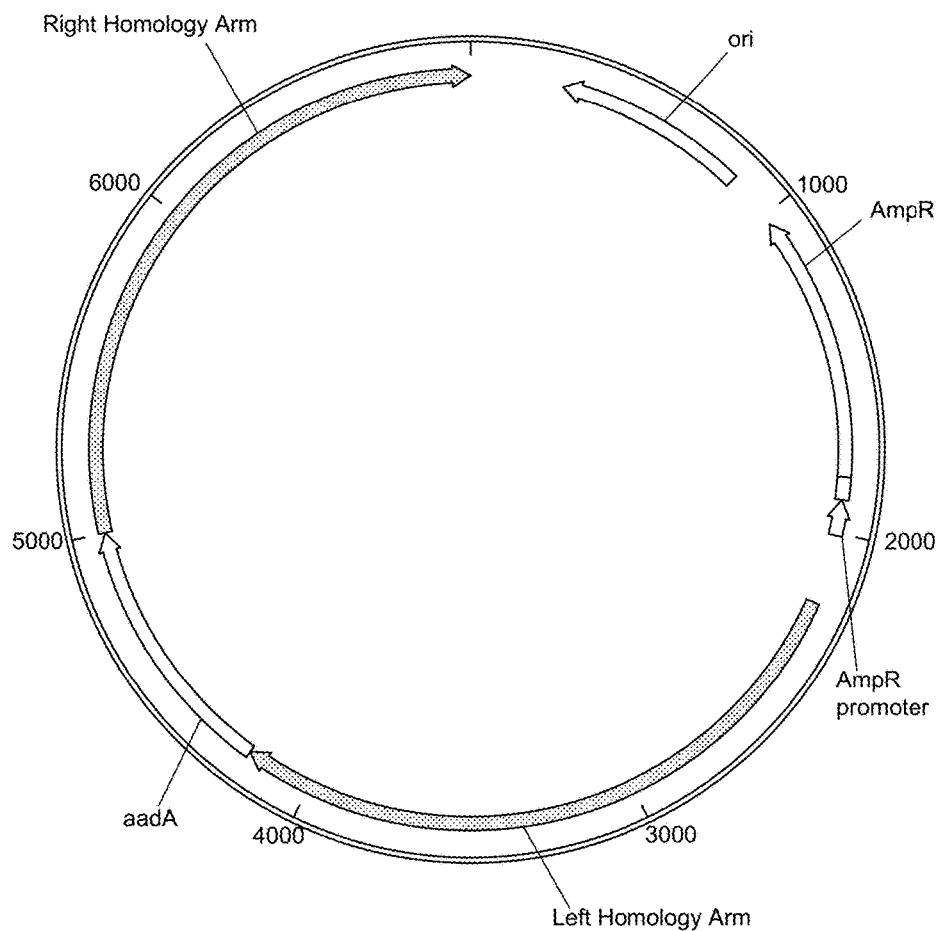
FIG. 2 shows a pApl-pilA/aadA plasmid used for targeted mutagenesis in *A. platensis* strain NIES-39. The plasmid of FIG. 2 has nucleotide sequence SEQ ID NO: 1.

FIG. 2 shows the pApl-pilA/aadA plasmid generated by assembling four PCR fragments containing a vector backbone, the left homology arm, the right homology arm and the aminoglycoside adenylytransferase gene (aadA) using the Gibson assembly method. This plasmid was then used to transform A. plantensis. The pApl-pilA/aadA plasmid includes aadA placed between the homology arms. aadA confers resistance to spectinomycin and streptomycin. Thus, homologous recombination with this plasmid replaces the pilA gene with the aadA gene. The plasmid also contains the AmpR gene (ampicillin resistance) under control of an AmpR promoter and an origin of replication (ori) in E. coli. 2.5 μg of this plasmid was mixed with 200 μL of the cell suspension. Immediately following mixing with the plasmid, the cells were electroporated using a Gene Pulser Xcell™ Microbial System (Bio-Rad, USA).

Following electroporation cells were grown without shaking at reduced illumination in SOT medium for 48 h then transferred to SOT medium supplemented with streptomycin. Presence of streptomycin in the medium selected for transformed cells. The medium including streptomycin was replaced every few days to maintain efficacy of the antibiotic. After growth in the streptomycin medium, the cells were cultured in SOT medium with streptomycin and spectinomycin.

Figure 3A:
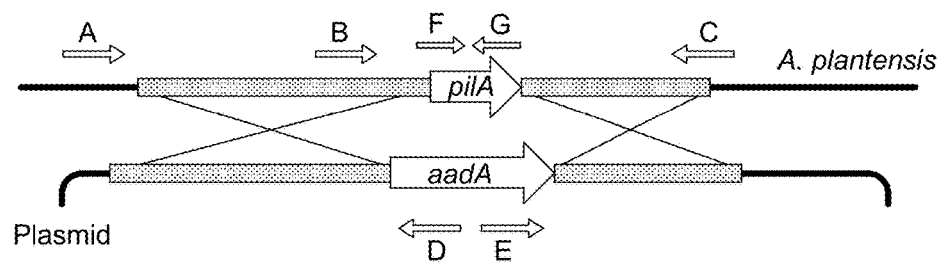
FIG. 3A shows a schematic of homologous recombination at the pilA gene locus (NIES39_C03030) in *A. platensis* strain NIES-39 with the plasmid of FIG. 2 containing the aminoglycoside adenyltransferase gene (aadA). Five PCR primer sites labeled A, B, C, D, E, F, and G are also shown.

FIG. 3A is a schematic of substitution of the open reading frame of pilA gene in A. plantensis with the aminoglycoside adenylyltransferase (aadA) gene contained in the pApl-pilA/aadA plasmid. Following successful homologous recombination the pilA gene was replaced with the aadA gene. Homology arms are shown as thick lines in the schematic. Three primers A, B, and C were identified that bind to the A. plantensis genome and two primers D and E were identified that bind to the aadA gene in the plasmid. The primers A and C were designed to initiate DNA synthesis by a DNA polymerase outside of the homology arms that exist on the aadA-containing plasmid. Thus, primers A and C bind to regions of the A. plantensis genome that remain unchanged following transformation. Primer A has SEQ ID NO: 13. Primer C has SEQ ID NO: 14. Primer B binds to the homology arm upstream of the pilA gene. Primer B has SEQ ID NO: 15. Primers D and E bind to the upstream and downstream ends, respectively, of the aadA gene. Primer D has SEQ ID NO: 16. Primer E has SEQ ID NO: 17.

Figures 3B, 3C:
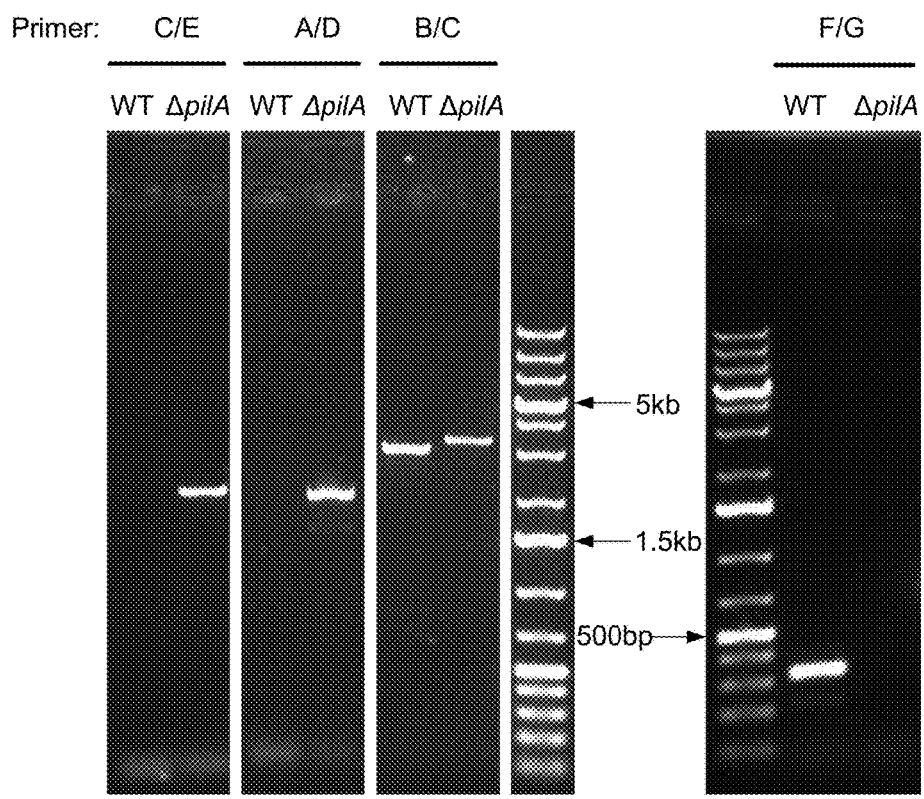
FIG. 3B shows the results of PCR amplification with primers C/E, A/D, and B/C for both wild-type *A. platensis* and *A. platensis* following transformation with the plasmid of FIG. 2.
FIG. 3C shows the results of PCR amplification with primers F/G of the pilA gene sequence in wild-type *A. platensis* and lack of amplification in *A. platensis* following transformation with the vector containing aadA.

FIG. 3B shows results of polymerase chain reaction (PCR) conducted with combinations of different primer pairs comparing wild-type A. plantensis (WT) and A. plantensis following transformation with the pApl-pilA/aadA plasmid (ΔpilA) as described above. Supernatants of boiled bacteria harvested after growth in streptomycin and spectinomycin were used as PCR templates. PCR was conducted under the following conditions: initial denaturation at 98° C. for 1 min and 35 cycles of denaturation at 98° C. for 30 sec, annealing at 71° C.-0.1° C. per cycle for 15 sec and extension at 72° C. for 1.5 min, followed by final extension at 72° C. for 2 min then cooling down to 4° C., for a reaction mixture with primers B and C; initial denaturation at 98° C. for 1 min, followed by 35 cycles of denaturation at 98° C. for 30 sec, annealing at 66° C. for 15 sec and extension at 72° C. for 1 min, followed by final extension at 72° C. for 2 min and cooling down to 4° C., for reaction mixtures with the rest of primers. The integration of aadA into the targeted locus was confirmed using two pairs of the primers (C/E and A/D). The ladder run on the gel has prominent bands at 5 kb, 1.5 kb, and 500 bp. Amplification using the C/E primer pair was not detected on WT but did yield a strong band at 2.2 kb on ΔpilA. Amplification with the A/D primer pair was similarly was not detected on WT but did yield a strong band at 2.1 kb on ΔpilA. Use of the primers B and C allows PCR amplification of the genomic sequences spanning either of pilA or aadA. Amplification of the WT sample (containing pi/A) generated a slightly shorter PCR product of about 3.1 kb than amplification of the transformed sample ΔpilA (containing aadA) of about 3.4 kb. This confirms expectations because the aadA sequence is about 300-bp longer than the pilA sequence. The PCR results demonstrate that the endogenous pilA gene was replaced with the aadA gene.

FIG. 3C shows that PCR with primers F and G complementary to the pilA gene failed to amplify any DNA from transformed cells grown in SOT medium supplemented with streptomycin and spectinomycin indicating that every copy of the pilA gene was replaced in cultures grown in the presence of the antibiotics. However, amplification with primers F and G amplified a 340-bp sequence from WT grown in SOT medium without antibiotics confirming that primers F and G are effective at amplifying the pilA gene. Primer F has SEQ ID NO: 18. Primer G has SEQ ID NO: 19. The ladder run on this gel has prominent bands at 5 kb, 1.5 kb, and 500 bp.

Example 2

Arthrospira sp. PCC 8005 cells were obtained from the Pasture Culture Collection (PCC) of Cyanobacteria maintained in the Laboratory Collection of Cyanobacteria, at Pasteur Institut (Paris) and cultured in SOT medium with shaking under continuous illumination for three days. The cells were diluted by 3 or 4 times in fresh SOT medium during the three day period. The cells were maintained under the above conditions until the optical density at 750 nm reached a desired level. Cells were then harvested at 3,200×g for 10 min from the culture. The supernatant was removed and the cells were suspended in a pH balancer and salt solution to neutralize pH. After centrifugation under the same conditions, cells were washed with 1-50 mL of 0.1-100 mM NaCL and an osmotic stabilizer three times, and then transferred into two 1.5 mL polypropylene microcentrifuge tubes (e.g., Eppendorf® tubes). The 1.5 mL microcentrifuge tubes were centrifuged at 3,200×g for 5 min at room temperature, and the supernatant was discarded. The cell suspension were twice diluted in NaCL and osmolyte solution then centrifuged again at 3,200×g for 5 min. The supernatant was removed and a total volume of the cell suspension was adjusted to 450 μl.

Figure 4:
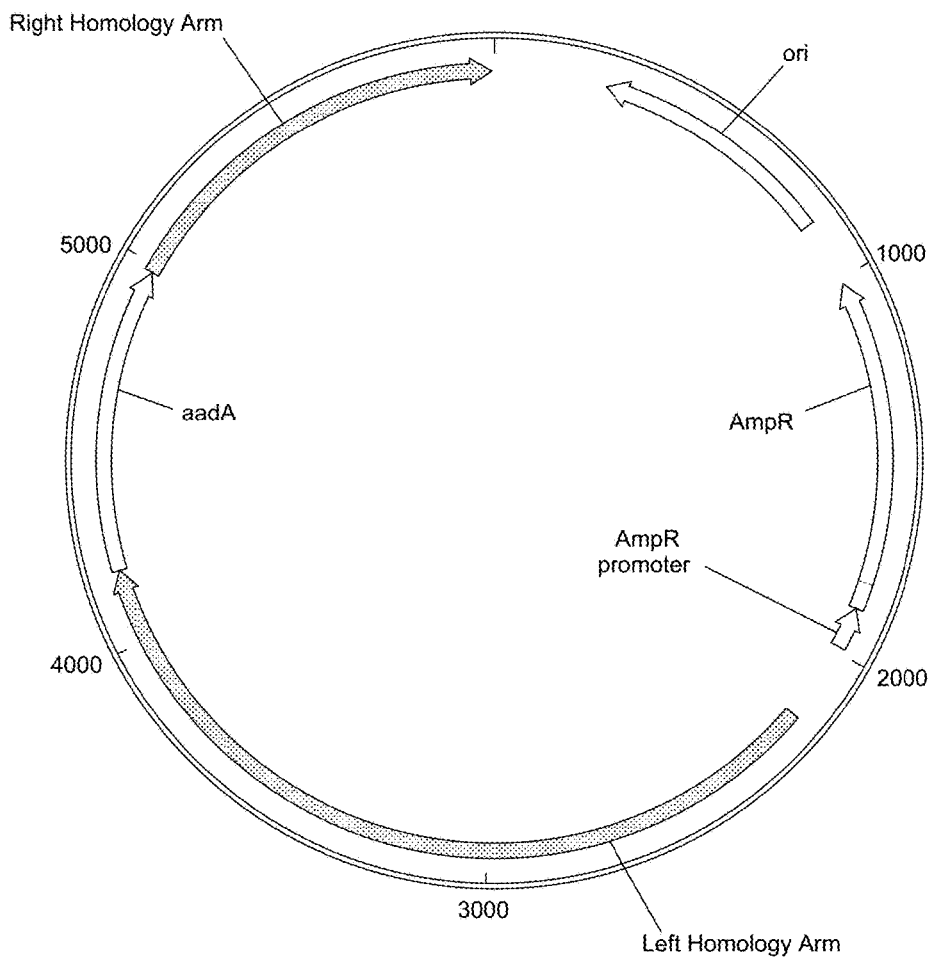
FIG. 4 shows a pApl-pilA8005/aadA plasmid used for targeted mutagenesis in *Arthrospira* sp. PCC 8005. The plasmid of FIG. 4 has nucleotide sequence SEQ ID NO: 2.

FIG. 4 shows the pApl-pilA8005/aadA plasmid (SEQ ID NO: 2) generated by using the Gibson assembly method to join four PCR fragments containing a vector backbone, a left homology arm, a right homology arm, and aadA encoding aminoglycoside adenyltransferase. In the pApl-pilA8005/aadA plasmid, aadA is located between the right and left homology arms which contain sequences identical to the genomic sequences found upstream and downstream of the pilA open reading frame in *Arthrospira* sp. PCC 8005. The left homology arm is 2.0 kb and the right homology arm is 1.0 kb. aadA confers resistance to spectinomycin and streptomycin. Thus, homologous recombination between *Arthrospira* sp. PCC 8005 and this plasmid replaces the pilA gene of *Arthrospira* sp. PCC 8005 with the aadA gene. The pApl-pilA8005/aadA plasmid also contains an operon encoding β-lactamase (AmpR) which confers ampicillin resistance under control of an AmpR promoter and an origin of replication (ori) from *E. coli*.

Four hundred µL of the suspended cells were mixed with 0.1-20 µg of the pApl-pilA8005/aadA plasmid, and transferred into an electroporation cuvette. Immediately following mixing, electroporation was performed using a Gene Pulser Xcell™ Microbial System (Bio-Rad, USA) electroporation system.

Following electroporation, 1 mL of SOT medium was added into the cuvette then the cells and SOT medium were transferred into a 50 mL polypropylene conical centrifuge tube (e.g., Falcon® tube) containing 9 mL of SOT medium. Cells were incubated at reduced illumination at 30° C. Successful transformants identified by antibiotic resistance were selected in the presence of streptomycin and spectinomycin.

Figure 5A:
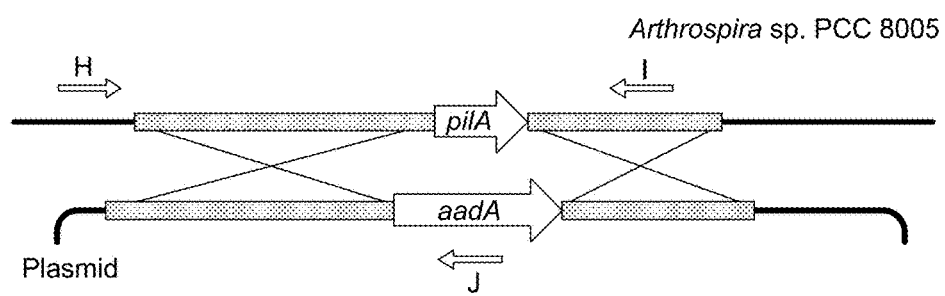
FIG. 5A shows a schematic of homologous recombination at the pilA gene locus in *Arthrospira* sp. PCC 8005 with the plasmid of FIG. 4 containing the aminoglycoside adenyltransferase gene (aadA). Three PCR primer sites labeled H, I, and J are also shown.

FIG. 5A is a schematic of substitution of the open reading frame of pilA gene in *Arthrospira* sp. PCC 8005 with the aminoglycoside adenylyltransferase (aadA) gene contained in the pApl-pilA8005/aadA plasmid. Following successful homologous recombination the pilA gene was replaced with the aadA gene. Homology arms are shown as shaded boxes in the schematic. Two primers H and I were identified that bind to the *Arthrospira* sp. PCC 8005 genome and one primer J was identified that binds to the aadA gene in the plasmid. Primer H initiates DNA synthesis by a DNA polymerase outside of the homology arms that exist on the pApl-pilA8005/aadA plasmid. Thus, primer H binds to a region of the *Arthrospira* sp. PCC 8005 genome that remains unchanged following transformation. Primer H has SEQ ID NO: 20. Primer I binds to the homology arm upstream of the pilA gene. Primer I has SEQ ID NO: 21. Primer J has SEQ ID NO: 22.

Figure 5B:
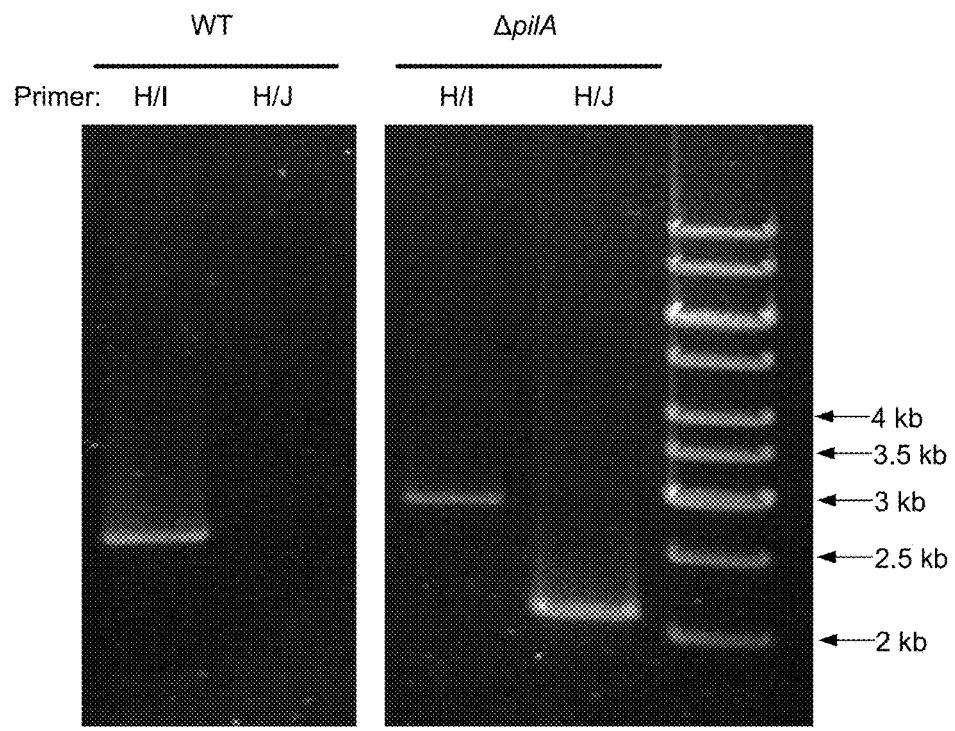
FIG. 5B shows the results of PCR amplification with primers H/I and H/J for both wild-type *Arthrospira* sp. PCC 8005 and *Arthrospira* sp. PCC 8005 following transformation with the plasmid of FIG. 4.

FIG. 5B shows results of PCR conducted on DNA extracted from the cells cultured in the presence of the antibiotics. The PCR was performed with primer pairs H/I and H/J on wild-type *Arthrospira* sp. PCC 8005 (WT) and *Arthrospira* sp. PCC 8005 following transformation with the pApl-pilA8005/aadA plasmid resulting in deletion of pilA (ΔpilA). PCR was conducted under the conditions described above in Example 1. Because there is no annealing site for primer J in wild-type *Arthrospira* sp. PCC 8005, the H/J primer pair will result in amplification only in the reaction mixtures containing DNA extracted from the transformed cells, indicating that pilA of *Arthrospira* sp. PCC 8005 was replaced with aadA. The integration of aadA into the targeted locus was confirmed using two pairs of the primers (H/I and H/J) and comparing the results by running the PCR products on a 1% w/v agarose gel.

Amplification of DNA extracted from wild-type *Arthrospira* sp. PCC 8005 with primer pair H/I shows a band between 2.5 kb and 3 kb indicating presence of the pilA gene. As expected, amplification of WT *Arthrospira* sp. PCC 8005 with the H/i primer pair does not result in any band because without transformation aadA is not present in the *Arthrospira* sp. PCC 8005 genome. DNA extracted from the transformed cells resulted in PCR products when amplified with either the H/I primer pair or the H/i primer pair. When the H/I primers are used on DNA from transformed cells, a band is present at approximately 3 kb which is slightly larger than the band resulting from H/I primer pair amplification of wild-type *Arthrospira* sp. PCC 8005. This demonstrates that the chromosome containing aadA was fully segregated since aadA is approximately 300 bp longer than pilA. The transformed cells, unlike the WT cells, also amplified with the H/i primer pair yielding a band slightly above 2 kb. The PCR results demonstrate that the endogenous pilA gene was replaced with the aadA gene and that the aadA gene was duplicated on all chromosomal copies.

Example 3

*Athrospira plantensis* NIES-39 was modified using the procedure from Example 2 to introduce exogenous genes encoding β-carotene 3,3'-hydroxylase (CrtZ) and β-carotene 4,4'-ketolase (CrtW) into the endogenous NIES39_Q01220 locus. *A. plantentis* does not naturally synthesize astaxanthin, but introduction of crtZ and crtW provides a biosynthesis pathway enabling the synthesis of this valuable carotenoid. The crtZ gene was obtained from *Pantoea ananatis* (SEQ ID NO: 23) and the crtW gene was obtained from *Brevundimonas* sp. SD212 (SEQ ID NO: 24). Both genes have been verified to function in *Synechococcus elongatus* PCC7942 and were codon optimized for expression in cyanobacteria.

Figure 6:
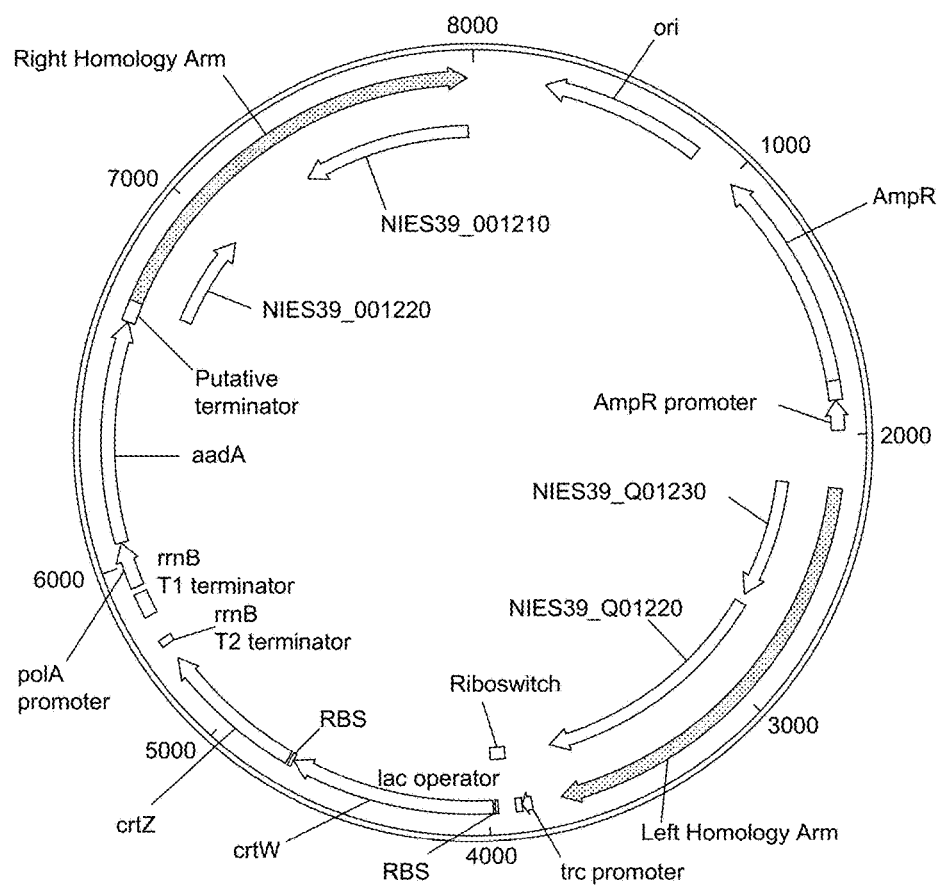
FIG. 6 shows a pApl-NS1/Prs-crtW-crtZ plasmid used to attempt to introduce crtW and crtZ genes by targeted mutagenesis in *A. platensis* strain NIES-39 to enable *A. platensis* to synthesize astaxanthin. The plasmid of FIG. 6 has nucleotide sequence SEQ ID NO: 3.

A pApl-NS1/Prs-crtW-crtZ plasmid was created to introduce crtZ and crtW into *A. plantentis*. This plasmid includes the aadA gene and the crtZ and crtW genes downstream of an inducible trc promoter connected to a riboswitch. FIG. 6 shows the design of the pApl-NS1/Prs-crtW-crtZ plasmid (SEQ ID NO: 3). This plasmid was generated by the same techniques described in Example 1.

Electroporation and culturing techniques were initially performed as described in Example 1 but for using the pApl-NS1/Prs-crtW-crtZ plasmid instead of the pApl-pilA/aadA plasmid from Example 1. Following this change transformation was not successful. Without being bound by theory expression of CrtW and CrtZ in cyanobacteria is believed to disrupt photosystems which may inhibit cell growth. It is theorized that the selected promoter, absent induction, did not sufficiently repress expression of the crtZ and crtW genes. Thus, presence of CrtW and CrtZ proteins may have prevented any transformed cells from growing. Transformation with genes that can inhibit growth may be dependent on a promoter design that very tightly regulates gene expression. Interaction between promotors, inserted genes, and transformation success is an area of further study.

Example 4

*Athrospira plantensis* NIES-39 is modified by adding additional copies of the cpcA and cpcB genes encoding C-phycocyanin α and β subunits. WT *Athrospira plantensis* NIES-39 has only a single set of these genes. Increasing the copy number of these endogenous genes increases synthesis of blue-colored C-phycocyanin. The cpcA (SEQ ID NO: 25) and cpcB (SEQ ID NO: 26) genes were obtained from WT *Athrospira plantensis* NIES-39.

Figure 7:
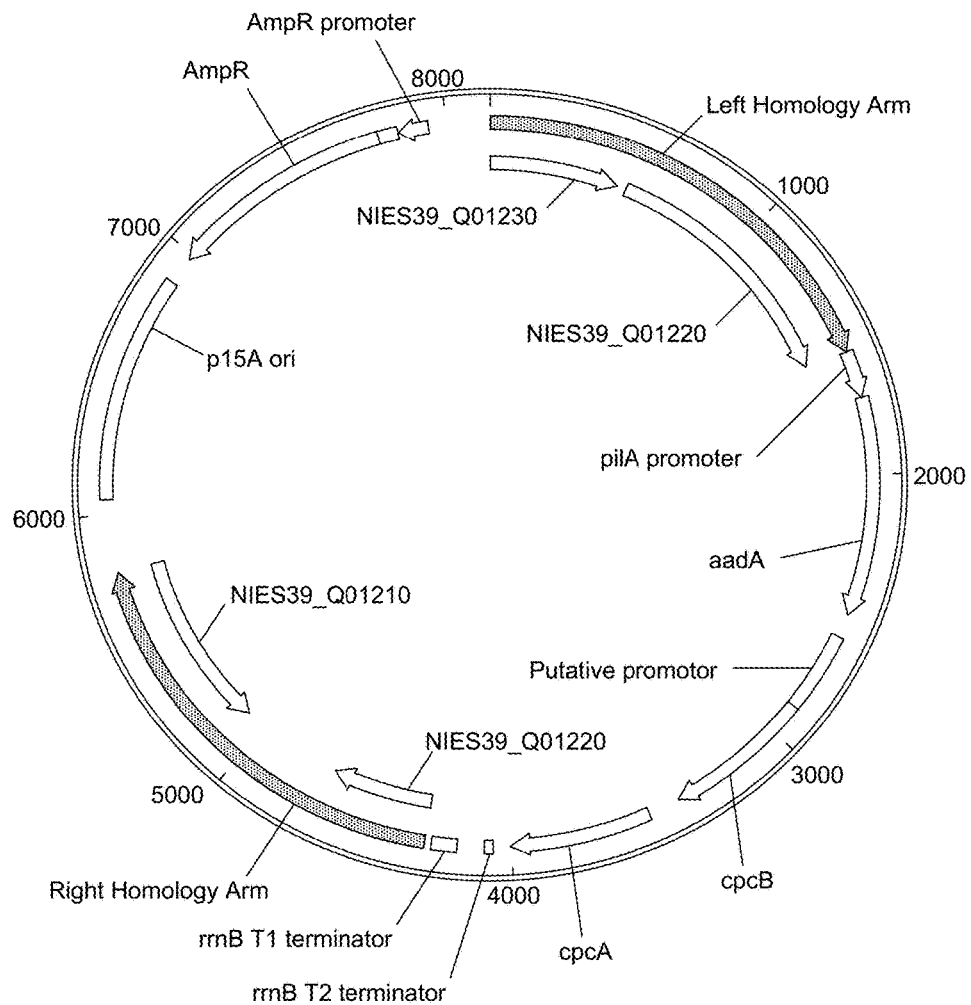
FIG. 7 shows a pApl-NS1/aadA-cpcBA plasmid used to introduce cpcA and cpcB genes by targeted mutagenesis in *A. platensis* strain NIES-39 to add additional copies of these two genes to *Athrospira*. This results in an *Athrospira* strain that overproduces C-phycocyanin. The plasmid of FIG. 7 has the nucleotide sequence SEQ ID NO: 4.

The plasmid used to introduce cpcB and cpcA into *A. plantentis* was created by the techniques described in Example 1. FIG. 7 shows a schematic of the pApl-NS1/aadA-cpcBA plasmid (SEQ ID NO: 4). This plasmid contains a low-copy p15A origin of replication, the pilA promoter (a 168-bp sequence upstream of the pilA open reading frame), aadA, and the genomic sequence (SEQ ID NO: 27) ranging from 278-bp upstream of cpcB to the 3' end of cpcA in the middle of gene locus NIES39_Q01220. The 1.5-kb flanking regions of the insertion site are the left and right homology arms that integrate the exogenous gene operons into the targeted gene locus (i.e. NIES39_Q01220).

*Athrospira plantensis* NIES-39 was transformed with the pApl-NS1/aadA-cpcBA plasmid using the protocol we described in Example 3.

Following transformation, the strain carrying the second copies of cpcB and cpcA was grown in 160 mL of SOT medium in under the same conditions as its parental strain (i.e. *Arthrospira plantensis* NIES-39). Cells were harvested from 12 mL of each culture every other day to quantify the amounts of C-phycocyanin and allophycocyanin. The collected cells were resuspended in 5 mL of 100 mM sodium phosphate buffer (pH 6.0), and centrifuged at 3,200×g for 5 min at room temperature. The pellets were suspended in 2.5 mL of 100 mM sodium phosphate buffer (pH 6.0); and 700 μl of the suspended cells were transferred on pre-scaled PVDF (polyvinylidene fluoride or polyvinylidene difluoride) membranes. The cells were extensively washed with water (15-20 mL×2) on the membranes, and dried in an oven overnight in order to calculate the weight of dry biomass. The remaining cells suspended in 100 mM sodium phosphate buffer (pH 6.0) were stored at −80° C. and diluted in the same 100 mM sodium phosphate buffer to 2.0 mg dry cell weight per mL of buffer. The cells were lysed by gentle agitation at 30° C. overnight and centrifuged at 16,000×g for 30 min at 4° C. The supernatant was transferred into new tubes, and centrifuged again under the same conditions. The supernatant was diluted in 100 mM sodium phosphate buffer (pH 6.0) and the optical densities were measured between 450 nm and 750 nm in 5-nm intervals to confirm that chlorophyll and carotenoids were excluded. The contents of C-phycocyanin (Cpc) and allophycocyanin (Apc) were calculated using the optical densities of clarified cell lysates at 620 nm and 650 nm. Concentrations of C-phycocyanin and allophycocyanin were calculated using the equation $OD_\lambda = C_{Cpc} \times E_{\lambda,Cpc} + C_{Apc} \times E_{\lambda,Apc}$ in which $\lambda$ equals 620 or 650 nm, where $C_{Cpc}$ is the concentration of C-phycocyanin (mg/mL), $E_{\lambda,Cpc}$ is the extinction coefficient of C-phycocyanin, $C_{Apc}$ is the concentration of allophycocyanin (mg/mL), $E_{\lambda,Apc}$ is the extinction coefficient of allophycocyanin, and OD (optical density) is the absorbance. Use of this equation is described in Yoshikawa and Belay (2008) J. AOAC Int.

FIGS. 8A-D are graphs comparing phycocyanin production and growth of *Arthrospira platensis* NIES-39 transformed to include a total of two copies of each of cpcA and cpcB (dotted lines) and WT *Arthrospira platensis* NIES-39 (solid lines). Error bars for all graphs show standard deviation from three independent experiments. Cells were harvested from the cultures every other day i.e. on days 2, 4, and 6 as described above. The data for all FIGS. 8A-D were gathered from cells grown under the same conditions.

Figure 8A:
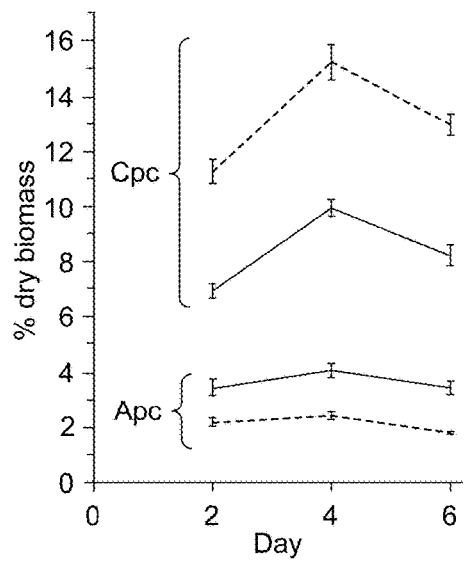
FIGS. 8A-8C shows improvements in C-phycocyanin production in *A. platensis* strain NIES-39 transformed with the plasmid of FIG. 7 as compared to wild-type *A. platensis*.

FIG. 8A shows Cpc and Apc production measured as percent of dry biomass. The transformed strain (dotted line) had approximately 3-5% more of its biomass as Cpc than the WT strain (solid line). For both strains the percentage of Cpc peaked on day 4 then decrease. Levels of Apc were about 1% lower in the transformed strain than in the WT strain.

Table 1 shows phycocyanin levels as a percentage of dry biomass further analyzed as pure phycocyanin and crude phycocyanin.

TABLE 1

| | | % dry biomass | |
|---|---|---|---|
| | Day | WT | pApl-NS1/aadA-cpcBA transformed strain |
| Pure Phycocyanin (%) | 2 | 8.68 ± 0.372 | 12.2 ± 0.490 |
| | 4 | 12.0 ± 0.406 | 16.3 ± 0.685 |
| | 6 | 9.96 ± 0.476 | 13.7 ± 0.391 |
| Crude Phycocyanin (%) | 2 | 18.6 ± 0.802 | 26.3 ± 1.06 |
| | 4 | 25.8 ± 0.875 | 35.1 ± 1.48 |
| | 6 | 21.4 ± 1.02 | 29.6 ± 0.843 |

Pure phycocyanin was calculated using the equation:

$$\% \text{ of dry bio mass as pure phycocyanin} = 100\left(\frac{OD_{260} \times \text{dilution factor}}{7.3 \times \text{dry weight}}\right).$$

Crude phycocyanin represents all phycobiliprotein pigments and was calculated using the equation:

$$\% \text{ of dry bio mass as crude phycocyanin} = 100\left(\frac{OD_{260} \times \text{dilution factor}}{3.39 \times \text{dry weight}}\right).$$

Figure 8B:
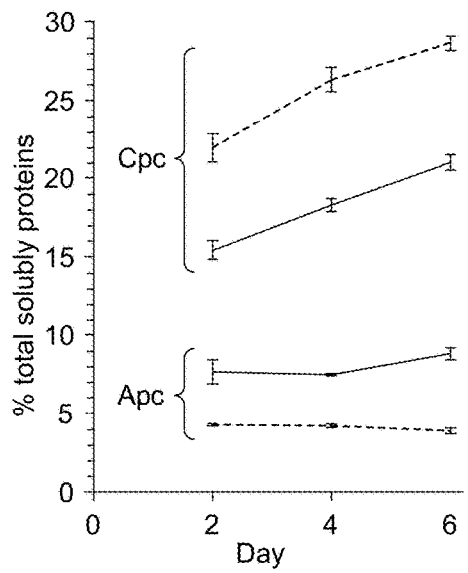

FIG. 8B shows Cpc and Apc production measured as percent of total soluble proteins. For both the WT (solid line) and transformed (dotted line) strains the percent of Cpc increased with time. The transformed strain had approximately 5% more of it total soluble proteins as Cpc than the WT strain. Levels of Apc were lower and relatively stable for both strains with the transformed strain having about 1% fewer of total soluble proteins as Apc than the WT strain.

Figure 8C:
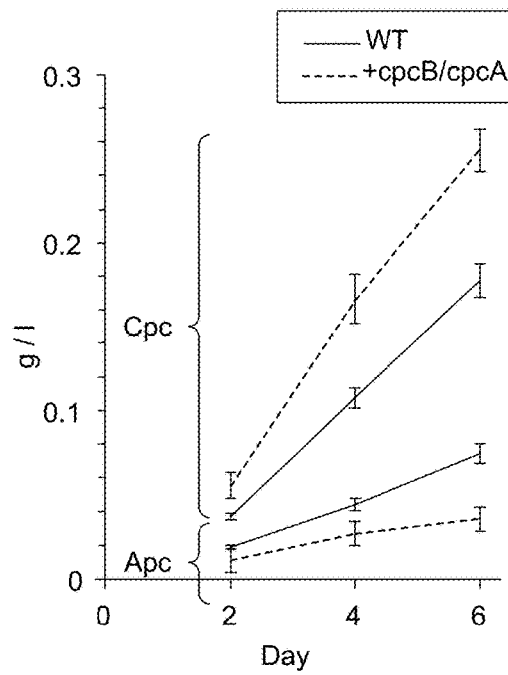

FIG. 8C shows total Cpc and Apc production in grams of phycocyanin per liter of cell culture. The total Cpc production of the transformed strain (dotted line) was more than that of the WT strain (solid line) at all time points and the difference increased with time. Apc levels also increased with time, but the WT strain produced higher levels of Apc than the transformed strain. The contents of Cpc and Apc varied depending on the growth phase, but at all time points and under all conditions, the transformed strain accumulated 50-100% greater amounts of Cpc and less Apc than the WT strain.

Figure 8D:
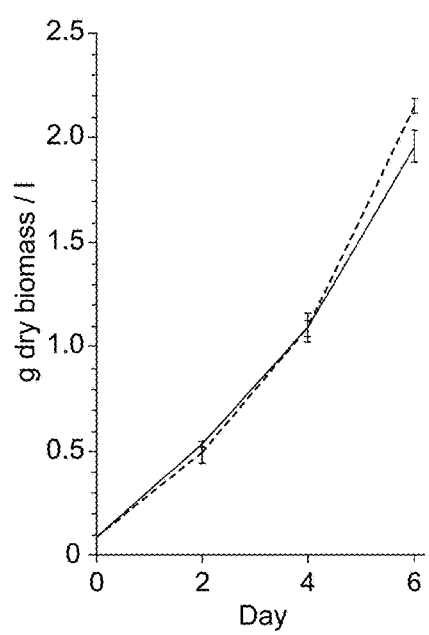
FIG. 8D shows that the transformed *A. platensis* has a growth rate similar to wild-type *A. platensis*.

FIG. 8D compares growth of the WT and transformed strains. The transformed strain grew (dotted line) at the same rate as the WT strain (solid line) on days 0-4 and only slightly slower on day 6.

Example 5

To analyze extracts from WT *Arthrospira platensis* NIES-39 and the transformed strain described above, both strains were cultured in 50 L photobioreactors of SOT medium to obtain biomass enough for protein extraction. The cultures were concentrated using a filter cartridge then the cells were harvested by centrifugation at 3,000×g for 10 min. The concentrated cells were then lyophilized. Two grams of dried biomass from each of the two strains were suspended in 20 mL of water and centrifuged at 3,200×g for 5 min to collect swelling biomass. The supernatant was removed and the pellet was suspended in 20 mL of water. After centrifugation under the same conditions, the pellets were then suspended in 80 mL of 20 mM sodium phosphate buffer (pH 6.0) by repeated pipetting and gently stirred at room temperature for 30 min. Sonication was performed twice at 50% of the maximal amplitude for 30 sec at room temperature using a Qsonica sonicator Q700. Following sonication, the suspended cells were stirred continually overnight at room temperature. To recover water-soluble extracts from the cell lysates, the samples were centrifuged at 4° C. for 30 min at 10,000×g once, then at 16,000×g twice. Seventy two milliliter of the supernatant from each cell lysate was transferred into a glass beaker, and 45 mL of 100% saturated ammonium sulfate in 20 mM sodium phosphate (pH 6.5) was gradually dropped into the beaker where the clarified cell extract was gently stirred at 4° C. The mixtures of the cell lysates and ammonium sulfate were stirred for an hour, precipitated proteins were recovered by centrifugation at 16,000×g for 30 min at 4° C. The pellet was suspended with 20 mM sodium phosphate buffer (pH 6.0) to adjust the total volume to 50 ml, and dialyzed using Slide-A-Lyzer cassettes against 2 L of 20 mM sodium phosphate buffer (pH 6.0) at 4° C. The outer buffer was exchanged three times (3 hours, overnight, then 4 hours). The samples were centrifuged at 4° C. for 30 min at 16,000×g, and the recovered supernatant were centrifuged again under the same conditions.

Figure 9A:
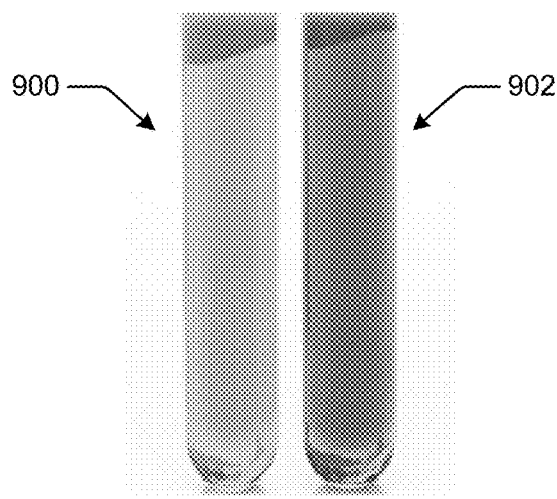
FIG. 9A shows a deeper blue color in a protein extraction from *A. platensis* strain NIES-39 transformed to overproduce C-phycocyanin and a lighter blue protein extraction from wild-type *A. platensis* strain NIES-39.

FIG. 9A is a photograph showing that supernatants recovered from the final centrifugation of the two strains have different intensity of blue color. The tube 900 containing WT *Arthrospira platensis* NIES-39 has a lighter blue color; and the tube 902 containing the strain transformed with the pApl-NS1/aadA-cpcBA plasmid has a darker blue color. C-phycocyanin has an intense blue color with a single visible absorbance maximum around 620 nm. Thus, the deeper blue color was expected from the supernatant of the C-phycocyanin-overproducing strain.

Figure 9B:
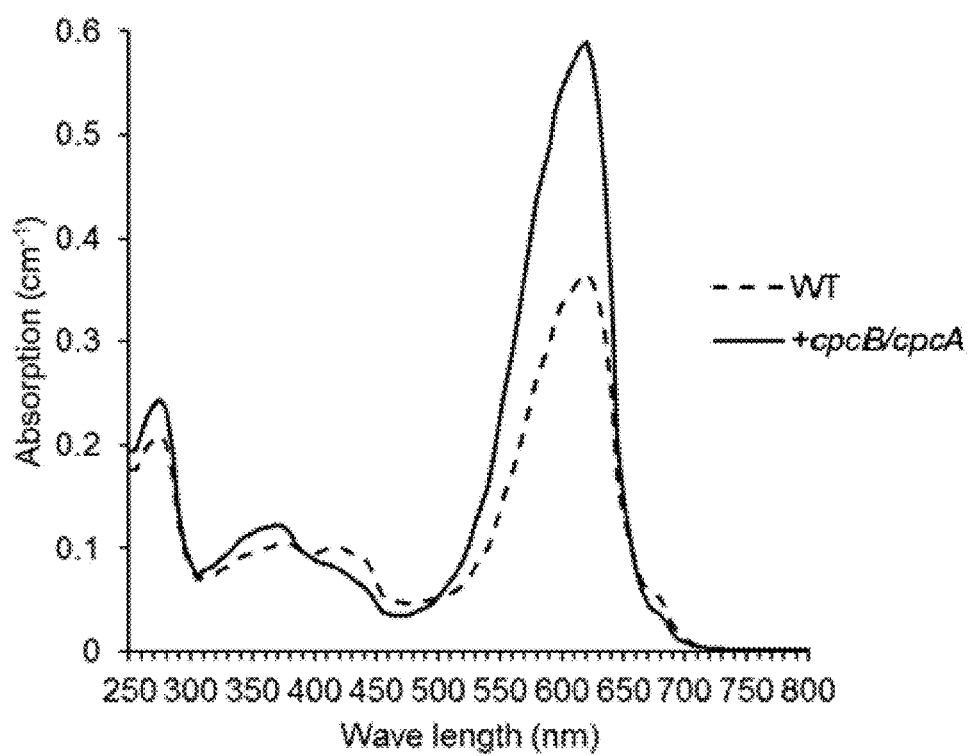
FIG. 9B is a graph showing absorption differences between the protein extractions from the transformed *A. platensis* strain NIES-39 and wild-type *A. platensis* strain NIES-39. Transformed *A. platensis* strain NIES-39 has greater absorption at 620 nm than the wild-type strain.

FIG. 9B is a graph showing absorption differences between the transformed strain (solid line) and the WT strain (dotted line). Both strains exhibited an absorbance peak around 620 nm. The peak absorbance for the transformed strain was approximately 0.60 $cm^{-1}$ and the peak for the WT strain was approximately 0.35 $cm^{-1}$. This quantitatively confirms the qualitative color difference shown in FIG. 9A.

Quality of C-phycocyanin extract can be determined by the ratio of the optical density at 620 nm ($OD_{620}$) to the optical density at 280 nm ($OD_{280}$). A higher ratio indicates a higher yield and purity of C-phycocyanin that may be suitable for higher-value uses such as cosmetics rather than lower value uses such as food grade dye. The graph in FIG. 9B shows that the $OD_{620}/OD_{280}$ ratio for the transformed strain is 2.5 compared to 1.8 for the WT strain. This indicates a 40% higher concentration of C-phycocyanin from the recovered supernatant of the transformed strain.

Illustrative Embodiments

Embodiment 1 is a *Spirulina* comprising at least one stable, targeted mutation.

Embodiment 2 is the *Spirulina* of any one of embodiments 1, 4-11, or 25, wherein the *Spirulina* is *Athrospiria platensis* or *Arthrospira maxima*.

Embodiment 3 is the *Spirulina* of any one of embodiments 1, 2, 4-11, or 25, wherein the *Spirulina* is *Athrospiria platensis* NIES-39 or *Arthrospira* sp. PCC 8005.

Embodiment 4 is the *Spirulina* of any one of embodiments 1-3, 5-11, or 25, wherein the stable targeted mutation is inherited for at least 10 generations.

Embodiment 5 is the *Spirulina* of any one of embodiments 1-4, 6-11, or 25, wherein the stable targeted mutation is integrated into a chromosome of the *Spirulina*.

Embodiment 6 is the *Spirulina* of any one of embodiments 1-5, 7-11, or 25, wherein the targeted mutation comprises a deletion or disruption of at least a portion of a gene.

Embodiment 7 is the *Spirulina* of any one of embodiments 1-6 or 8-11 wherein the targeted mutation comprises an addition of an additional copy of an endogenous gene or addition of an exogenous gene.

Embodiment 8 is the *Spirulina* of any one of embodiments 1-7, 10, or 11 wherein the targeted mutation comprises addition of a gene regulatory element.

Embodiment 9 is the *Spirulina* of embodiment 8, wherein the gene regulatory element is a promoter, a regulatory protein binding site, a RNA binding site, a ribosome binding site, or a RNA stability element.

Embodiment 10 is the *Spirulina* of any one of embodiments 1-9 or 11 wherein the targeted mutation comprises addition of an exogenous or endogenous protein domain.

Embodiment 11 is the *Spirulina* of embodiment 10, wherein the exogenous protein domain is a phosphorylation site, a stability domain, a protein targeting domain, or protein-protein interaction domain.

Embodiment 12 is a method of creating a targeted mutation in *Spirulina*, the method comprising: contacting the *Spirulina* with an osmotic stabilizer; contacting the *Spirulina* with a vector having homology arms; and inducing artificial competence in the *Spirulina*.

Embodiment 13 is the method of any one of embodiments 12 or 15-24, wherein the *Spirulina* is *Spirulina platensis*.

Embodiment 14 is the method of any one of embodiments 12 or 15-24, wherein the *Spirulina* is *Athrospiria platensis* NIES-39 or *Arthrospira* sp. PCC 8005.

Embodiment 15 is the method of any one of embodiments 12-24, wherein the osmotic stabilizer is at least one of polyethylene glycol, ethylene glycol, glycerol, glucose, or sucrose.

Embodiment 16 is the method of any one of embodiments 12-24, wherein the vector is a DNA vector, a linear vector, a circular vector, a single stranded polynucleotide, or a double stranded polynucleotide.

Embodiment 17 is the method of any one of embodiments 12-24, wherein the vector comprises a vector having SEQ ID NO: 1, SEQ ID NO: 2, or SEQ ID NO: 4.

Embodiment 18 is the method of any one of embodiments 12-24, wherein at least one of the homology arms is at least 500 bp.

Embodiment 19 is the method of any one of embodiments 12-24, wherein at least one of the homology arms is at least 1000 bp.

Embodiment 20 is the method of any one of embodiments 12-24, wherein at least one of the homology arms is at least 2000 bp.

Embodiment 21 is the method of any one of embodiments 12-20 and 22-24, wherein the artificial competence is induced by incubation in a solution containing divalent cations, by electroporation, or by ultrasound.

Embodiment 22 is the method of any one of embodiments 12-24, further comprising contacting the *Spirulina* with a pH balancer.

Embodiment 23 is the method according to any one of embodiments 22 or 24, wherein contacting the *Spirulina* with the pH balancer is prior to contacting the *Spirulina* with the vector.

Embodiment 24 is the method according to any one of embodiments 22 or 23, wherein a pH of a media containing the *Spirulina* and the pH balancer is about 7 to about 8.

Embodiment 25 is a *Spirulina* lacking at least one protein as a result of introducing a modification at the loci of the protein by transformation of the *Spirulina* with at least one DNA construct comprising a sequence homologous with at least a portion of the loci and the modification and integration of the DNA construct at the loci, the *Spirulina* being otherwise capable of functioning in its native manner.

Embodiment 26 is a *Spirulina* comprising an exogenous gene encoding phycocyanin as a result of introducing the exogenous gene at a targeted loci by transformation of the *Spirulina* with at least one DNA construct comprising a sequence homologous with at least a portion of the targeted loci and the exogenous gene and integration of the DNA construct at the locus, the *Spirulina* producing an increased amount of phycocyanin relative to wild-type *Spirulina* and maintaining the transformation throughout multiple generations.

What is claimed is:

1. A non-naturally occurring, stable transformant *Spirulina* comprising:
   a. at least one introduced targeted nucleotide mutation incorporated into the *Spirulina* genome, wherein the introduced targeted nucleotide mutation is adjacent to a region of nucleotides that is homologous to a nucleotide homology arm contained in a vector utilized to transform said cell via homologous recombination.

2. The *Spirulina* of claim 1, wherein the *Spirulina* is *Arthrospira platensis* or *Arthrospira maxima*.

3. The *Spirulina* of claim 2, wherein the *Spirulina* is *Arthrospira platensis* NIES-39 or *Arthrospira* sp. PCC 8005.

4. The *Spirulina* of claim 1, wherein the introduced targeted nucleotide mutation is inherited for at least 10 generations.

5. The *Spirulina* of claim 1, wherein the introduced targeted nucleotide mutation comprises a deletion or disruption of at least a portion of a gene.

6. The *Spirulina* of claim 1, wherein the introduced targeted nucleotide mutation comprises addition of an additional copy of an endogenous gene or addition of an exogenous gene.

7. The *Spirulina* of claim 1, wherein the introduced targeted nucleotide mutation comprises addition of a gene regulatory element.

8. The *Spirulina* of claim 7, wherein the gene regulatory element is a promoter, a regulatory protein binding site, a RNA binding site, a ribosome binding site, or an RNA stability element.

9. The *Spirulina* of claim 1, wherein the introduced targeted nucleotide mutation comprises addition of a polynucleotide sequence encoding an exogenous protein domain.

10. The *Spirulina* of claim 9, wherein the exogenous protein domain is a phosphorylation site, a stability domain, a protein targeting domain, or protein-protein interaction domain.

11. A method of creating a introduced targeted mutation in *Spirulina*, the method comprising:
    contacting the *Spirulina* with an osmotic stabilizer;
    contacting the *Spirulina* with a vector having a nucleotide homology arm; and
    inducing artificial competence in the *Spirulina*.

12. The method of claim 11, wherein the *Spirulina* is *Spirulina platensis*.

13. The method of claim 11, wherein the *Spirulina* is *Arthrospria platensis* NIES-39 or *Arthrospira* sp. PCC 8005.

14. The method of claim 11, wherein the osmotic stabilizer is at least one of polyethylene glycol, ethylene glycol, glycerol, glucose, or sucrose.

15. The method of claim 11, wherein the vector is a DNA vector, a linear vector, a circular vector, a single stranded polynucleotide, or a double stranded polynucleotide.

16. The method of claim 11, wherein the vector comprises a vector having SEQ ID NO: 1, SEQ ID NO: 2, or SEQ ID NO: 4.

17. The method of claim 11, wherein the nucleotide homology arm is at least 500 bp.

18. The method of claim 11 wherein the nucleotide homology arm is at least 1000 bp.

19. The method of claim 11, wherein the nucleotide homology arm is at least 2000 bp.

20. The method of claim 11, wherein the artificial competence is induced by electroporation.

21. The method of claim 11, further comprising contacting the *Spirulina* with a pH balancer.

22. The method according to claim 21, wherein contacting the *Spirulina* with the pH balancer is prior to contacting the *Spirulina* with the vector.

23. The method according to claim 21, wherein a pH of a media containing the *Spirulina* and the pH balancer is about 7 to about 8.

24. A *Spirulina* lacking at least one protein as a result of introducing a modification at the loci of the protein by transformation of the *Spirulina* with at least one DNA construct comprising a sequence homologous with at least a portion of the loci and the modification and integration of the DNA construct at the loci, the *Spirulina* being otherwise capable of functioning in its native manner.

25. A *Spirulina* comprising an exogenous gene encoding phycocyanin as a result of introducing the exogenous gene at a targeted loci by transformation of the *Spirulina* with at least one DNA construct comprising a sequence homologous with at least a portion of the targeted loci and the exogenous gene and integration of the DNA construct at the locus, the *Spirulina* producing an increased amount of phycocyanin relative to wild-type *Spirulina* and maintaining the transformation throughout multiple generations.

26. The non-naturally occurring, stable transformant *Spirulina* of claim 1, wherein the introduced targeted nucleotide mutation is flanked by two regions of nucleotides that are homologous to nucleotide homology arms contained in a vector utilized to transform said cell via homologous recombination.

\* \* \* \* \*

SEQUENCE LISTING

```
<160> NUMBER OF SEQ ID NOS: 27

<210> SEQ ID NO 1
<211> LENGTH: 6994
<212> TYPE: DNA
<213> ORGANISM: Artificial Sequence
<220> FEATURE:
<223> OTHER INFORMATION: pApl-pilA plasmid backbone including addA gene
      with homology arms and restriction sites for Asd (GGCGCGCC) and
      EcoRI (GAATTC)

<400> SEQUENCE: 1
gaattcacat acgcggccgc ctgggccttg agctcgaatt tcctgcatta atgaatcggc      60
caacgcgcgg ggagaggcgg tttgcgtatt gggcgctctt ccgcttcctc gctcactgac    120
tcgctgcgct cggtcgttcg gctgcggcga gcggtatcag ctcactcaaa ggcggtaata    180
cggttatcca cagaatcagg ggataacgca ggaaagaaca tgtgagcaaa aggccagcaa    240
aaggccagga accgtaaaaa ggccgcgttg ctggcgtttt tccataggct ccgcccccct    300
gacgagcatc acaaaaatcg acgctcaagt cagaggtggc gaaacccgac aggactataa    360
agataccagg cgtttccccc tggaagctcc ctcgtgcgct ctcctgttcc gaccctgccg    420
cttaccggat acctgtccgc ctttctccct tcgggaagcg tggcgctttc tcatagctca    480
cgctgtaggt atctcagttc ggtgtaggtc gttcgctcca agctgggctg tgtgcacgaa    540
ccccccgttc agcccgaccg ctgcgcctta tccggtaact atcgtcttga gtccaacccg    600
gtaagacacg acttatcgcc actggcagca gccactggta acaggattag cagagcgagg    660
tatgtaggcg gtgctacaga gttcttgaag tggtggccta actacggcta cactagaaga    720
acagtatttg gtatctgcgc tctgctgaag ccagttacct tcggaaaaag agttggtagc    780
tcttgatccg gcaaacaaac caccgctggt agcggtggtt tttttgtttg caagcagcag    840
attacgcgca gaaaaaaagg atctcaagaa gatcctttga tcttttctac ggggtctgac    900
gctcagtgga acgaaaactc acgttaaggg attttggtca tgagattatc aaaaaggatc    960
ttcacctaga tccttttaaa ttaaaaatga agttttaaat caatctaaag tatatatgag   1020
taaacttggt ctgacagtta ccaatgctta atcagtgagg cacctatctc agcgatctgt   1080
ctatttcgtt catccatagt tgcctgactc cccgtcgtgt agataactac gatacgggag   1140
ggcttaccat ctggccccag tgctgcaatg ataccgcgag acccacgctc accggctcca   1200
gatttatcag caataaacca gccagccgga agggccgagc gcagaagtgg tcctgcaact   1260
ttatccgcct ccatccagtc tattaattgt tgccgggaag ctagagtaag tagttcgcca   1320
gttaatagtt tgcgcaacgt tgttgccatt gctacaggca tcgtggtgtc acgctcgtcg   1380
tttggtatgg cttcattcag ctccggttcc caacgatcaa ggcgagttac atgatccccc   1440
atgttgtgca aaaaagcggt tagctccttc ggtcctccga tcgttgtcag aagtaagttg   1500
gccgcagtgt tatcactcat ggttatggca gcactgcata attctcttac tgtcatgcca   1560
tccgtaagat gcttttctgt gactggtgag tactcaacca agtcattctg agaatagtgt   1620
```

```
atgcggcgac cgagttgctc ttgcccggcg tcaatacggg ataataccgc gccacatagc    1680
agaactttaa aagtgctcat cattggaaaa cgttcttcgg ggcgaaaact ctcaaggatc    1740
ttaccgctgt tgagatccag ttcgatgtaa cccactcgtg cacccaactg atcttcagca    1800
tcttttactt tcaccagcgt ttctgggtga gcaaaaacag gaaggcaaaa tgccgcaaaa    1860
aagggaataa gggcgacacg gaaatgttga atactcatac tcttcctttt tcaatattat    1920
tgaagcattt atcagggtta ttgtctcatg agcggataca tatttgaatg tatttagaaa    1980
aataaacaaa taggggttcc gcgcacattt ccccgaaaag tgccacctga cgtctaagaa    2040
accattatta tcatgacatt aacctataaa aataggcgta tcacgaggcc ctttcgtctc    2100
gcgcgtttcg gtgatgacgg tgaaaacctc tgacacatgc agctcccgga cggtcaca     2160 gcttgtctgt aagcggatgc caagcttgca tgcctgcagg tggcgcgccg aatgacgcta    2220
acagcaggac ctatattggg aattaggttg aggagtccgg cgagaatggc attggcgaaa    2280
attaagggga ctctcagtat ccacaagccg actactgtta gtagggtgac accaatcatg    2340
ttgagtaagg caccgattag ccaacgacct agggctattt cgcaagtatc gagaatgtcg    2400
ttcattcgcc ttcggtaaaa ggcgggaatt agttgtaagc tgctgcgacg gtaggcttgg    2460
gggtcggcta aaagcatgag ggtgaggacg aggattaata agatgctgac taatccttct    2520
actgtggttc cgacgacgac cccaaaaccg ccgattaatt gattgctgag gcttgggct    2580 tgttggataa tttgttcgat gcggatctgt ctcaggtcgc gactgacttc tgatagatat    2640
tcccgtaagg gtccgttgag gtcggtgcgt aaatagtcaa ttaacaggtt cagcagcttt    2700
agaccttgtt cgagaccggc ggggaccctgt ttggctagtt gttctaattg gttgattagg    2760 gggggggacta ccaataaaaa gccgatggta atccctaaga agaatagact aatggatagg    2820
aagacggcaa gcgatcgcgg tagtttcaga cgctggaatt gacgggtgag acggtttaag    2880
gcggtggcta ggacgacggc ggcgaaaatc atcagcaggg cttgtttaat ccgccacagg    2940
atgtatatag cgattaagaa agctgtgaag cctatccatg tacctagggt cattgcgact    3000
gttgagggtg agagaatttg cttttctaca ggcgatcgcc tgtacaatag ttatctatca    3060
tagaatacta gattctgtgg tgggattcca ccaaagccag ccagctacct atgacgcaac    3120
ccagatatga tgaacaggaa aatatatctc gccacgcagc ggtagatgaa ggatgctgcg    3180
aggatatgga acgaaaatat gggtggaatc ttgtgcgaat tgaggtaacc tcagatccta    3240
tccttgaggt tgattgcgta tttctgggga aaacggagtt ccctcggccc tataatgaaa    3300
ctgataagga ggaagattga tgcgaaaata catcattttt cgggctgata agggtgaacc    3360
tggttggaaa gaacgtaaac tccaacatac ccagggttta actagaattt ggctgaaca    3420 tttcgactct tctgatcaac ctattcctga gttgggatat cgaccgaggg agtttattcg    3480
tattgatggg ttgcataatc ccactgaaca tggctacagc acccattatc gtcagggtga    3540
ctgggaagta actagggtag aaagttactc tcctgatgtg tctatggctg agtttgatat    3600
gatcgtgatt tgcttttgca aatatagccc tgttaatggt cctgtgcaac ctatgccaga    3660
gcgtcgagtg tctgtagatg ggttcgctgg ggatgagaag cggttggagc aatggcacga    3720
gtcccaaaag aaaccgactg aggtttagtt ggtcccggt ttgcttattt gactagccag    3780
attcgccacg acaacagaac cgccagcagg gaagagggga atagaaccgc gaaaagagcg    3840
atcgcattgg tttcgggaat ggcgaaattt ggcccgccat atttgatcag taaggatagc    3900
cctagggata ggatcaggat tttggccacc aataacagtt tgttgtccat ttatatatag    3960
```

```
gatgcgatgg gatgcgatcg cctatatttt accaattggt ggcggcctta accccctaag    4020
ccctatgtct gacacccagt caccccaacc gccttagtcg gtattcccca ctgggtgggc    4080
gatacacgat ttcccggaaa aattgaaaaa aaattttgtg gcaggtgata tgatttgcga    4140
tcgaggtggt taagttagaa ctacagaaaa caaataacct catttcaccc cgaggagaac    4200
gaattatgag ggaagcggtg atcgccgaag tatcgactca actatcagag gtagttggcg    4260
tcatcgagcg ccatctcgaa ccgacgttgc tggccgtaca tttgtacggc tccgcagtgg    4320
atggcggcct gaagccacac agtgatattg atttgctggt tacggtgacc gtaaggcttg    4380
atgaaacaac gcggcgagct ttgatcaacg acctttggga aacttcggct tccccctggag   4440 agagcgagat tctccgcgct gtagaagtca ccattgttgt gcacgacgac atcattccgt    4500
ggcgttatcc agctaagcgc gaactgcaat ttggagaatg gcagcgcaat gacattcttg    4560
caggtatctt cgagccagcc acgatcgaca ttgatctggc tatcttgctg acaaaagcaa    4620
gagaacatag cgttgccttg gtaggtccag cggcggagga actctttgat ccggttcctg    4680
aacaggatct atttgaggcg ctaaatgaaa ccttaacgct atggaactcg ccgcccgact    4740
gggctggcga tgagcgaaat gtagtgctta cgttgtcccg catttggtac agcgcagtaa    4800
ccggcaaaat cgcgccgaag gatgtcgctg ccgactgggc aatggagcgc ctgccggccc    4860
agtatcagcc cgtcatactt gaagctagac aggcttatct tggacaagaa gaagatcgct    4920
tggcctcgcg cgcagatcag ttggaagaat ttgtccacta cgtgaaaggc gagatcacca    4980
aggtagtcgg caaataacag ataatctagc agtttaggtt tcagatggag tcagctaggg    5040
tctttaaccc catcgtcaac tataagatgg agagatggca tacggtgaca ctgttaaagc    5100
cataactata ttgctcttgt tgataaaatc agaaactgag gccacttgag agtattgtaa    5160
ataggtagta cagtagtgct acctattttg ttttaaaata actaattgag tttatcgctg    5220
ggactatggt tgataatcag atgtcggaaa agcagaatat tttatcagca gaagctgata    5280
tttacttgca taaagggat tatcaacaag cagccatttt tatgaacaa gccatcaatc     5340 tcaatcccga ctataaatat aattactgga aactggggtt aaccctgctg ctacaggagc    5400
gggaggaaga agcccagacc acctggctgg tggcgatgag tgatggagac ccagaacaga    5460
ttgaccagtg gacgatagac ttactcgagg tgctatcatc agaagccgat gcacgaacct    5520
ccgccgaaga ctattccgtg gcttggggga ttcgccaaca cattttagaa ataaaccccc    5580
atggtattga taatatatta aagttaattg atttgtcaat taccctgaca acctataccg    5640
gaaatgagat cgcagaatat ggactggttc ccttactgca acaggagtcc atcaatgtca    5700
atccagattt actactgcac ctgtggaaaa aactcctagt tgtagatgca attaatcccc    5760
tatctctgga attgggagag gcggtgatta accatcttgg tgagcaaccg gagtttgtca    5820
ctagcttaat ccctaaatta tacgatattg cctattcctt tggtgaaata ggtatagcca    5880
agggctatgg agagttgttg ttgaacctgg caccgcatca tcaagagttg ctgagggctc    5940
tggctcaatt ttgtattcaa ttaaccgagt atgaccatgg cattgaatat gccagacgtt    6000
cctatcatct cactgaatcc ccagatcagc aagccctgga tagcaatttt atgatcagtg    6060
gtctgatgtc tcaagggga tgcacaaagc aagtgcgaga ggtggtcaac catcaggaat    6120
cattgctgga tgctatgctg aaagacccgc ccctagactt gggaactggg gttatgcaat    6180
tatataatac cagcttttc tttccttatg ttagagattc acctgctgtc aactcacaaa    6240
taaaagccca agttgctcaa atttgccaag ccaacttaga aacggctcag gcagaaaata    6300
tcgccacata tcaagcccgg aatttacaga aacgccatca atccgcgacc aatcaacccc    6360
```

```
taaaaattgg ttatatatct tattgtttcc ggcggcattc tgtgggttgg atatctcgct    6420
ggttatttca acatcacgat cgcgataaat ttgaaattta tgcctatatg attggggcag    6480
aaaatcgaca agatgctctc caaaactggt atgcagaaca agccaacaag tcttatcaat    6540
atggaatagt aagcacagaa gttgccgagc aaatttctga agaccagatt gatattctca    6600
ttgatttaga tagcctgaca ttaaccaata cctgcgccat tatggcactt aaacccgcac    6660
ctgtacaagt cacctggttg ggatgggatg cctctgctat acccaccgtt gactatttta    6720
ttgctgaccc ctatgttttg ccagaaaatg cccaggatta ttactcagaa accatctggc    6780
gactacctca aacctatgtg gccgtcggtg gcttcgaggt cggcattccc agtttgcgaa    6840
gagaggatat caatattccc gaaaatgcca ttgtttattt taccgcccaa aggggggccga   6900 aatacaaccc agaactagcc caattgcaaa tgcaaattct gaaacaagta cccaatagtt    6960
atttggtaat taagggattc gataaagagc aatc                                6994
```

<210> SEQ ID NO 2
<211> LENGTH: 5967
<212> TYPE: DNA
<213> ORGANISM: Artificial Sequence
<220> FEATURE:
<223> OTHER INFORMATION: pApl-pilA8005/aadA plasmid including aadA gene
      flanked by homology arms

<400> SEQUENCE: 2

```
gcctgggcct tgagctcgaa tttcctgcat taatgaatcg gccaacgcgc ggggagaggc      60
ggtttgcgta ttgggcgctc ttccgcttcc tcgctcactg actcgctgcg ctcggtcgtt     120
cggctgcggc gagcggtatc agctcactca aaggcggtaa tacggttatc cacagaatca     180
ggggataacg caggaaagaa catgtgagca aaaggccagc aaaaggccag gaaccgtaaa     240
aaggccgcgt tgctggcgtt tttccatagg ctccgccccc ctgacgagca tcacaaaaat     300
cgacgctcaa gtcagaggtg gcgaaacccg acaggactat aaagatacca ggcgtttccc     360
cctggaagct ccctcgtgcg ctctcctgtt ccgaccctgc cgcttaccgg atacctgtcc     420
gcctttctcc cttcgggaag cgtggcgctt tctcatagct cacgctgtag gtatctcagt     480
tcggtgtagg tcgttcgctc caagctgggc tgtgtgcacg aaccccccgt tcagcccgac     540
cgctgcgcct tatccggtaa ctatcgtctt gagtccaacc cggtaagaca cgacttatcg     600
ccactggcag cagccactgg taacaggatt agcagagcga ggtatgtagg cggtgctaca     660
gagttcttga agtggtggcc taactacggc tacactagaa gaacagtatt tggtatctgc     720
gctctgctga agccagttac cttcggaaaa agagttggta gctcttgatc cggcaaacaa     780
accaccgctg gtagcggtgg tttttttgtt tgcaagcagc agattacgcg cagaaaaaaa     840
ggatctcaag aagatccttt gatcttttct acggggtctg acgctcagtg gaacgaaaac     900
tcacgttaag ggattttggt catgagatta tcaaaaagga tcttcaccta gatccttta     960 aattaaaaat gaagttttaa atcaatctaa agtatatatg agtaaacttg gtctgacagt    1020
taccaatgct taatcagtga ggcacctatc tcagcgatct gtctatttcg ttcatccata    1080
gttgcctgac tccccgtcgt gtagataact acgatacggg agggcttacc atctggcccc    1140
agtgctgcaa tgataccgcg agacccacgc tcaccggctc cagatttatc agcaataaac    1200
cagccagccg gaagggccga gcgcagaagt ggtcctgcaa ctttatccgc ctccatccag    1260
tctattaatt gttgccggga agctagagta agtagttcgc cagttaatag tttgcgcaac    1320
gttgttgcca ttgctacagg catcgtggtg tcacgctcgt cgtttggtat ggcttcattc    1380
```

```
agctccggtt cccaacgatc aaggcgagtt acatgatccc ccatgttgtg caaaaaagcg    1440
gttagctcct tcggtcctcc gatcgttgtc agaagtaagt tggccgcagt gttatcactc    1500
atggttatgg cagcactgca taattctctt actgtcatgc catccgtaag atgcttttct    1560
gtgactggtg agtactcaac caagtcattc tgagaatagt gtatgcggcg accgagttgc    1620
tcttgcccgg cgtcaatacg ggataatacc gcgccacata gcagaacttt aaaagtgctc    1680
atcattggaa aacgttcttc ggggcgaaaa ctctcaagga tcttaccgct gttgagatcc    1740
agttcgatgt aacccactcg tgcacccaac tgatcttcag catcttttac tttcaccagc    1800
gtttctgggt gagcaaaaac aggaaggcaa aatgccgcaa aaaagggaat aagggcgaca    1860
cggaaatgtt gaatactcat actcttcctt tttcaatatt attgaagcat ttatcagggt    1920
tattgtctca tgagcggata catatttgaa tgtatttaga aaaataaaca aatagggggtt    1980 ccgcgcacat ttccccgaaa agtgccacct gacgtctaag aaaccattat tatcatgaca    2040
ttaacctata aaaataggcg tatcacgagg ccctttcgtc tcgcgcgttt cggtgatgac    2100
ggtgaaaacc tctgacacat gcagctcccg gagacggtca cagcttgtct gtaagcggat    2160
gccaagcttg catgcctgca ggtggcgcga acagaagacg accaacactt tctccctgat    2220
gggttgcgcc ctgatcaatg tcctttaaac cctgatacgt tcttcaaccg tcgaacctag    2280
tccaaccgag tagcccataa ctgaccaccc tatttaatca tgttgcattc tgagcggaac    2340
catgttcaac cccaaactat ccccaagtt ctcccggtcc agtgaatctg gctacaccct    2400
gcttgagtcc atcatggcta tggtggtggt cagcatcctg atggtcggca tttctccggt    2460
gttgggtttt gccttcgcca cacgggtaca ggctcggcgc atagaactag ccagcagagc    2520
cgctaacagt tatatcagtg ctgtccgtac tgacccaacc aataccaact tggtgctgtt    2580
caatcccagt gaccggaacg ctggaccaac tgcaactggt agcttgaact gtggggctgg    2640
tcgagcctgt accaccccag ccaacttgtt ctgtgtggat aatgacgaa gtgggggatg    2700 tgaaaccgat agccccacgg atatgattgt tcagggaatt ggcataaatg agtgtagcga    2760
cgagctagag aatggttatc agttgattgt caggggtgtat cgtgctgacg catttgccca    2820
atcgggacaa ctagagggggg ctaatgatga cgggtctagt aatttagcga gttcccgagt    2880
cggtttagga accccagag accccctagt gcaggtgcga accgagatta gccccactag    2940
caccagttcc tttgggagtt tacgtgaccg tttagcagga tgcagttctg acgatgaagg    3000
ggattaatag gtttggtgat ggttcccatg gagtgcaaaa gtaagattat cccggtagag    3060
aggtagttat gctgtcccta gttcggtttt ggttaatttg tgtattgaaa tctaggtcaa    3120
aaaccaccca ggggaatgac ttaggcttca cgatgattga gttattgatt tcggctgttg    3180
tggctagtat gatcatcacg cccatcctat tctttgtggt ggatgttta cgaaccgata    3240 cccgggaaga aatcacagcc agatcggaac aggagttaca ggcggcagca gatttcattc    3300
gtcgcgacct ctcccaggct atctatatct acgacggtga aggggttaat gcgattagga    3360
gccaacttcc tgattccgat aatgtggtat tggtgttctg gaaacaggag tttcgcgaag    3420
gtgtgattcc tcacggtgac gtccccaggc cagttgctgc taatcattgc gatacgaggc    3480
gttgcgatga tgtccaagtt ttatctttag ttgcttacta tttacaaaca gaaagagagc    3540
ctaatagtcc ttggtctgat caggcgcgta tttctcgctt acaaatcaac gatggtgtca    3600
tcgatccgaa tccagaagat gaatgcaccc aaccaccatg ttatgtcaaa ctgggtgata    3660
aggaattcaa accagaccga ggttttgatc gacctcctgg ccgtacaagc atgaatgctt    3720
```

```
gggaagcaaa agagggcgag cagattgaag catcacgaga agttctgatt gattacatag    3780
acaaaacaga actaacaggt gatatagatt gtgaatctcg tggcatcagt aatgatgata    3840
gtgaggattt actatccgtg ggtaagaatt ctgagggaa tcctatctat ggcttttttg     3900
tatgtgtaga ctcccgtaat acagcagctt tagttaacct gagaatgaat gcggcaattc    3960
gcattgatcc gaatgctaca gaattcgacg aggataggcg atcgcttttt ccagagacca    4020
gcttttggt taaaggctta ggtgttttca attaaccgat aaaatcaggg aatttataat     4080
aaaaggaacc tataaaatga gtattttaat taacccaaaa tcggtgaatc ccaggcgcac    4140
caaaaaccag tcgggcttca ccatcattga gacgttggtg gtagttttaa tgagggaagc    4200
ggtgatcgcc gaagtatcga ctcaactatc agaggtagtt ggcgtcatcg agcgccatct    4260
cgaaccgacg ttgctggccg tacatttgta cggctccgca gtggatggcg gcctgaagcc    4320
acacagtgat attgatttgc tggttacggt gaccgtaagg cttgatgaaa caacgcggcg    4380
agctttgatc aacgaccttt tggaaacttc ggcttcccct ggagagagcg agattctccg    4440
cgctgtagaa gtcaccattg ttgtgcacga cgacatcatt ccgtggcgtt atccagctaa    4500
gcgcgaactg caatttggag aatggcagcg caatgacatt cttgcaggta tcttcgagcc    4560
agccacgatc gacattgatc tggctatctt gctgacaaaa gcaagagaac atagcgttgc    4620
cttggtaggt ccagcggcgg aggaactctt tgatccggtt cctgaacagg atctatttga    4680
ggcgctaaat gaaaccttaa cgctatggaa ctcgccgccc gactgggctg gcgatgagcg    4740
aaatgtagtg cttacgttgt cccgcatttg gtacagcgca gtaaccggca aaatcgcgcc    4800
gaaggatgtc gctgccgact gggcaatgga gcgcctgccg gcccagtatc agcccgtcat    4860
acttgaagct agacaggctt atcttggaca agaagaagat cgcttggcct cgcgcgcaga    4920
tcagttggaa gaatttgtcc actacgtgaa aggcgagatc accaaggtag tcggcaaata    4980
agtagttata actagccaat tgtaacacaa aaaattaatt atctactgaa tattttacaa    5040
aactttaccc ccaatttcgg aaaacatagt ttagaataca ccaccaaaga tatcacccgt    5100
aacgaggcct tttacgagtg agattagttg tgtatgctgc ggttagctga cctacacgac    5160
atctatcctt gtgacccagg ttaaataatg gaaaatacat taattaagca cttgcttctg    5220
gttcagaaac aggctattaa tttagtgcct gaaaaacctg ttagcagtga ctatcagggt    5280
gcgaaatcgc gaaaatcctc tacagaatca gggttttctt tgttagaagt gttaggggtg    5340
atggtgatta tatcaatact aggtgggata gcggttccga cttggttagg tttcgcgaat    5400
aaccagaaac tgcaaacctc tatccggcga ctcaactggg ctatccactc agccaaaagt    5460
gaggctatac tatctagtac atcatggcaa gcgagtatca gggaatatgg gggacgagta    5520
caggtagcag tccatcccgc gaagactccc cctggtcaac tcccagaagg ttcatggact    5580
aacctagaac cggggataga aattgacaac cgggaaagga acaccaggaa taaatatgaa    5640
actaccctgc gaagagtaga cccggacacc aaccaagtcc gaaacgcggg gacggtgtac    5700
cgagttttat tcaactacca aggctgtccg gtctataacc cgtctaattt atgcacgcaa    5760
acttctctag ctgcgaaggg acgcattgct atccatcatc ctgaagttcc aggtcaaaag    5820
cgatgtatca tcatttcgac gctgataggt gcgactcgca ttggtcagca acagcaaaga    5880
ccggatcaaa atggctacta ttgccattaa ttaataatta ataattaata attaataatt    5940
attaattggg tagcgaccct gtgggcc                                        5967
```

<210> SEQ ID NO 3
<211> LENGTH: 8117

<212> TYPE: DNA
<213> ORGANISM: Artificial Sequence
<220> FEATURE:
<223> OTHER INFORMATION: pApl-NS1/Prs-crtW-crtZ plasmid including aadA gene, crtW, crtZ, and homology arms

<400> SEQUENCE: 3

```
gcctgggcct tgagctcgaa tttcctgcat taatgaatcg gccaacgcgc ggggagaggc      60
ggtttgcgta ttgggcgctc ttccgcttcc tcgctcactg actcgctgcg ctcggtcgtt     120
cggctgcggc gagcggtatc agctcactca aaggcggtaa tacggttatc cacagaatca     180
ggggataacg caggaaagaa catgtgagca aaaggccagc aaaaggccag gaaccgtaaa     240
aaggccgcgt tgctggcgtt tttccatagg ctccgccccc ctgacgagca tcacaaaaat     300
cgacgctcaa gtcagaggtg gcgaaacccg acaggactat aaagatacca ggcgtttccc     360
cctggaagct ccctcgtgcg ctctcctgtt ccgaccctgc cgcttaccgg atacctgtcc     420
gcctttctcc cttcgggaag cgtggcgctt tctcatagct cacgctgtag gtatctcagt     480
tcggtgtagg tcgttcgctc caagctgggc tgtgtgcacg aaccccccgt tcagcccgac     540
cgctgcgcct tatccggtaa ctatcgtctt gagtccaacc cggtaagaca cgacttatcg     600
ccactggcag cagccactgg taacaggatt agcagagcga gtatgtaggc ggtgctaca      660
gagttcttga agtggtggcc taactacggc tacactagaa gaacagtatt tggtatctgc     720
gctctgctga agccagttac cttcggaaaa agagttggta gctcttgatc cggcaaacaa     780
accaccgctg gtagcggtgg tttttttgtt tgcaagcagc agattacgcg cagaaaaaaa     840
ggatctcaag aagatccttt gatcttttct acggggtctg acgctcagtg gaacgaaaac     900
tcacgttaag ggattttggt catgagatta tcaaaaagga tcttcaccta gatcctttta     960
aattaaaaat gaagttttaa atcaatctaa agtatatatg agtaaacttg gtctgacagt    1020
taccaatgct taatcagtga ggcacctatc tcagcgatct gtctatttcg ttcatccata    1080
gttgcctgac tccccgtcgt gtagataact acgatacggg agggcttacc atctggcccc    1140
agtgctgcaa tgataccgcg agacccacgc tcaccggctc cagatttatc agcaataaac    1200
cagccagccg gaagggccga gcgcagaagt ggtcctgcaa cttta tccgc ctccatccag    1260
tctattaatt gttgccggga agctagagta agtagttcgc cagttaatag tttgcgcaac    1320
gttgttgcca ttgctacagg catcgtggtg tcacgctcgt cgtttggtat ggcttcattc    1380
agctccggtt cccaacgatc aaggcgagtt acatgatccc ccatgttgtg caaaaaagcg    1440
gttagctcct tcggtcctcc gatcgttgtc agaagtaagt tggccgcagt gttatcactc    1500
atggttatgg cagcactgca taattctctt actgtcatgc catccgtaag atgcttttct    1560
gtgactggtg agtactcaac caagtcattc tgagaatagt gtatgcggcg accgagttgc    1620
tcttgcccgg cgtcaatacg ggataatacc gcgccacata gcagaacttt aaaagtgctc    1680
atcattggaa aacgttcttc ggggcgaaaa ctctcaagga tcttaccgct gttgagatcc    1740
agttcgatgt aacccactcg tgcacccaac tgatcttcag catcttttac tttcaccagc    1800
gtttctgggt gagcaaaaac aggaaggcaa atgccgcaa aaagggaat aagggcgaca     1860
cggaaatgtt gaatactcat actcttcctt tttcaatatt attgaagcat ttatcagggt    1920
tattgtctca tgagcggata catatttgaa tgtatttaga aaataaaca aatagggg tt    1980
ccgcgcacat ttccccgaaa agtgccacct gacgtctaag aaaccattat tatcatgaca    2040
ttaacctata aaaataggcg tatcacgagg cccttcgtc tcgcgcgttt cggtgatgac    2100
ggtgaaaacc tctgacacat gcagctcccg gagacggtca cagcttgtct gtaagcggat    2160
```

```
gccaagcttg catgcctgca ggtggcgcgc caggtccgaa gaagaacgca ccatagctgc    2220
tggtaaagaa gcccgcgcca gggctgaaca actcctgcaa actgtccgcg ctgagttgga    2280
aaggttgcga ctcgaagctg ataccgtcct acctgcagag gcggagcgag aagccagaga    2340
actgcaagcc agaggtaatg cggccgcttt agcggaaaat tcccgcgcgg cggcggaagt    2400
aaacgacctg attaacgcag tttggcagga atgggcgac gacgcatcgg aactgtttta    2460
cttacaacaa attgagatgg tcttgcgcga agctgcccaa attccccgcc gggttagtct    2520
ggaatatgtc aatgttattg atagtggaga cggggaagcg atcgctggtt tggttcgcgc    2580
ctatcccgaa attttccgcc aattcctcga agtgtcgat cgcactttgg gtattaatgt     2640
atctaggact ttgggggaac ataacaagca gaaattaaat aacaattagt caatttgatg    2700
gcaaccaaac acaggtacag gaattatgga aattatcatc gccttattag cagccctggg    2760
tttaggaacc ggagcgactg tatttattat ccgcaatctc tactatattt gtcagcctag    2820
cgaagtgttg attttgccg gaggtcgtcg ccctacacaa gatgatcgca ctgtgggata     2880
tcgcctggtg aaaggtggta gcagcattcg gacacccctg ctagaacaag cctttcacat    2940
ggatttaacc aatatgatta ttgagttaaa ggtggctaat gcttactcga aaggaggcat    3000
tcctttacag gttgatgggg tggcgaatat taaaattgct ggggaagaac ccacaattca    3060
taatgcgatc gagcgtttgt tggggaaaac tcgccaggaa attgaacgca ttgctaaaga    3120
taccctggaa ggaaacctgc gcggggtatt agccagcctt actcctgaac aggttaatgg    3180
ggataaattg gcttttgcta aaagtctcct cgaagaagct gaggatgact agaacaact     3240 ggggctgatt ttagatactc tccaaattca aaatatttct gatgacgtgg gatatcttga    3300
ctccatcgga cgacaacaac gggcggaatt gtttagagat tctcgtgtcg ctgaagcaca    3360
agctaaggct gatgctgcta ccgtactgc ggaaaatcat aaaatgactc agttgaaaaa      3420
gttggaaact gaggtagagg tatctaaggc ggaagctgaa cgccgggtgg ctgatgctat    3480
gactaaacgg gcggcggtgg tagcagagtc ggagtcggaa acagcggctg aggtggctag    3540
gactcaggct gaggtctctg ttcaaaaaga aaggattaag caggtagaac agcaactaca    3600
agctgatgtg gtcgcaccag cagaggcgga atgtaaaaag gcgatcgcta gggcgcgggg    3660
ggatgctgcc caaattattg aagatgggaa agcacaagct gaagggacac gacgactggc    3720
tgagtcttgg aaagcagccg gtcggaccgt cactgcaata ttcgtgtcgc tcaaggcgca    3780
ctcccgttct ggataatgtt ttttgcgccg acatcataac ggttctggca aatattctga    3840
aatgagctgt tgacaattaa tcatccggct cgtataatgt gtggaattgt gagcggataa    3900
caatttcata cgctcacaat tggtaccggt gataccagca tcgtcttgat gcccttggca    3960
gcaccctgct aaggaggcaa caagatgacg gctgcggtcg ctgagccgcg aatcgtgcct    4020
cgtcaaacct ggatcgggct cacacttgca gggatgattg tggcaggctg ggggagtctt    4080
cacgtctatg gagtctactt tcatcgctgg ggacaagta gcctcgttat tgtgccagca     4140
atcgtggctg tccagacctg gctcagtgtg ggcctattca ttgtcgcaca cgacgctatg    4200
cacgggtcgc tggcgccggg tcggcctcgc ctaaacgcag ccgtaggcag actcaccta     4260 gggctctatg ccggtttccg atttgatcgc cttaaacgg cccaccacgc acatcacgcc     4320
gcccccggta ctgccgatga ccctgatttc tacgcccag caccgcgagc gttttgcct     4380 tggttcctca acttctttcg cacttacttt ggctggcgtg agatggctgt tctgacagct    4440
ttagtcctaa tagccttgtt tggtttgggt gcccggccgg caaatcttct cacgttctgg    4500
```

```
gcagctccgg cgctgttaag tgctctacag ctattcactt ttggcacgtg gctgccgcac    4560
cgccacactg atcagccttt tgcggacgcc caccatgctc ggtcttccgg ttacggcccg    4620
gtgctcagcc tgcttacctg ttttcacttt ggtcggcacc acgaacacca tctgacaccg    4680
tggcgcccct ggtggcggct atggcgaggt gagagctaaa cacaggaaac aggaattaga    4740
tatgctgtgg atttggaacg cgctgatcgt gtttgtcaca gtcatcggga tggaagttat    4800
tgccgccttg gcacacaaat acatcatgca cggctggggc tggggatggc atctgtctca    4860
ccacgaaccc cgcaaaggcg ctttcgaagt caatgatctg tatgctgtcg tgtttgcagc    4920
cctgagcatt ttgctcatct acctgggctc gaccggtatg tggccgttgc aatggattgg    4980
tgccggcatg accgcctacg gtctgctgta tttcatggtg cacgatggcc tggtccatca    5040
acggtggcct tttcggtata ttccccgaaa gggctacctg aagcgcctat atatggccca    5100
tcgaatgcat cacgcagtcc gggggaagga agggtgtgtg agttttgggt ttctatatgc    5160
tcccccgttg tcgaaactgc aagcaaccct gcgtgagcgt catggcgctc gcgctggggc    5220
ggcgcgggac gcgcaagggg gcgaagatga accggcatcg gggaaataaa ctagtcatcg    5280
agctagcaag cttggccgga tccggccgga tccggagttt gtagaaacgc aaaaaggcca    5340
tccgtcagga tggccttctg cttaatttga tgcctgcag tttatggcgg gcgtcctgcc    5400
cgccaccctc cgggccgttg cttcgcaacg ttcaaatccg ctcccggcgg atttgtccta    5460
ctcaggagag cgttcaccga caaacaacag ataaaacgaa aggcccagtc tttcgactga    5520
gcctttcgtt ttatttgatg cctggcagtt ccctactctc gagtcacccc aaccgcctta    5580
gtcggtattc cccactgggt gggcgataca cgatttcccg gaaaaattga aaaaaaattt    5640
tgtggcaggt gatatgattt gcgatcgagg tgggtaagtt agaactacag aaaacaaata    5700
acctcatttc accccgagga gaacgaatta tgagggaagc ggtgatcgcc gaagtatcga    5760
ctcaactatc agaggtagtt ggcgtcatcg agcgccatct cgaaccgacg ttgctggccg    5820
tacatttgta cggctccgca gtggatggcg gcctgaagcc acacagtgat attgatttgc    5880
tggttacggt gaccgtaagg cttgatgaaa caacgcggcg agctttgatc aacgaccttt    5940
tggaaacttc ggcttcccct ggagagagcg agattctccg cgctgtagaa gtcaccattg    6000
ttgtgcacga cgacatcatt ccgtggcgtt atccagctaa gcgcgaactg caatttggag    6060
aatggcagcg caatgacatt cttgcaggta tcttcgagcc agccacgatc gacattgatc    6120
tggctatctt gctgacaaaa gcaagagaac atagcgttgc cttggtaggt ccagcggcgg    6180
aggaactctt tgatccggtt cctgaacagg atctatttga ggcgctaaat gaaaccttaa    6240
cgctatggaa ctcgccgccc gactgggctg gcgatgagcg aaatgtagtg cttacgttgt    6300
cccgcatttg gtacagcgca gtaaccggca aaatcgcgcc gaaggatgtc gctgccgact    6360
gggcaatgga gcgcctgccg gcccagtatc agcccgtcat acttgaagct agacaggctt    6420
atcttggaca agaagaagat cgcttggcct cgcgcgcaga tcagttggaa gaatttgtcc    6480
actacgtgaa aggcgagatc accaaggtag tcggcaaata actagctggc ctggaagggt    6540
gggaaagtgt taacaactgg ttgacaatat tccgcttttc caggtcttgt cgaagtacga    6600
ctacgggtat tgatgtggcg acggctgttc aaaattgggg cggcggttct tctcaacctc    6660
aacctacttc cacagctaaa agtctcaaat cttcccgcac taatggtcaa gctgttcgcc    6720
gcactaatgg cgcagcacct aagccagaag atactcacaca aagcctacag agcgaggtta    6780
aacaactact tgatcatgtc gcacaaaata ctaagaataa tgctgaggct gaagaggcga    6840
tcgcccaggc tttgcgacag tatcctaacc tcaagcgtcg tttacagatg cttttttaagt    6900
```

```
ctcagggaac tcaggcgatc cgaaatatgt taatcaccc tactatctac atccctaccg    6960
ctatgctgca aatgtggcta gaacaggatt agagcgtatt cccccccctc tcgtctaggg   7020
tgggggatct gtctctgtaa ctgtatatgc acaaaatggc gttttttgtca ataagccgaa  7080 aaatggaccc cgcttttaac cccaaaactc gtgcatcgcc agttttattt tttggtaaga   7140
taataattat aaccgcgaca aaataagggt tttagccttt attttttggaa atagacacag   7200 taagcccttg ggtgcgattt ccttgagcat accataaccc ccataatctc gtcaactttt   7260
tgcgaggtat ttgccataaa attgtattaa ttcttaacaa tattttaaaa ataaaatcta   7320
tctagccgta taaattagta aaatttatgt aatttcccga ttgagggggt ggggtgtggg    7380
ggggtttata gtcaaattaa tgtgattgga tctcatttaa cctctgacgt actacttgca    7440
tatcctgcca cattaaccat ttaggtttac caacatctcg cgaggaattt ctgagtaggt    7500
atgcagggtg aaaaatcggc atacattgac gaccttccca ctgaaaccac tgaccgcgaa   7560
ttttagtaat cgggcgttta tctcctagaa tagacttaac tgcagtcgcc ccagttagga    7620
ggataatttg aggattaatg aggcggattt gttctaatag ataaggctta caggcttgga    7680
gttctgaagc ggttggggtg cgattttccg ggggacgaca gcggatagca ttagaaatat   7740
aaacttcggt atctgtactc agtcctacgg agtctaaaat attatcaaga agttttccag    7800
atctaccgac aaacggaaga ccttgttcat cttcatgttg tcctggtgct tctccgataa    7860
tcataatggg ggcggtgggg ttccctcgac caatcacagc atgagtgcgg ttttttccaa    7920
gttcacagcg cgagcaccta ttacaatgat cggcaatttg tgcgagagtt tgataggttc   7980
ccggcggtat gggagtcttg gcattttggg gaatttcttc taggtcaaaa tctaccgact    8040
taggggattg taatgggtct tgattaacac taagaatatc gaacaggctg agttgttggg    8100
aattcacata cgcggcc                                                   8117
```

<210> SEQ ID NO 4
<211> LENGTH: 8146
<212> TYPE: DNA
<213> ORGANISM: Artificial Sequence
<220> FEATURE:
<223> OTHER INFORMATION: pApl-NS1/aadA-cpcBA plasmid backbone including
      aadA, cpcA, and cpcB genes with a p15A origin of replication

<400> SEQUENCE: 4

```
aggtccgaag aagaacgcac catagctgct ggtaaagaag cccgcgccag ggctgaacaa     60
ctcctgcaaa ctgtccgcgc tgagttggaa aggttgcgac tcgaagctga taccgtccta   120
cctgcagagg cggagcgaga agccagagaa ctgcaagcca gaggtaatgc ggccgcttta   180
gcggaaaatt cccgcgcggc ggcggaagta aacgacctga ttaacgcagt ttggcaggaa    240
atgggcgacg acgcatcgga actgttttac ttacaacaaa ttgagatggt cttgcgcgaa    300
gctgcccaaa ttccccgccg ggttagtctg gaatatgtca atgttattga tagtggagac    360
ggggaagcga tcgctggttt ggttcgcgcc tatcccgaaa ttttccgcca attcctcgaa    420
agtgtcgatc gcactttggg tattaatgta tctaggactt tggggaaaca taacaagcag    480
aaattaaata caattagtc aatttgatgg caaccaaaca caggtacagg aattatggaa    540
attatcatcg ccttattagc agccctgggt ttaggaaccg gagcgactgt atttattatc    600
cgcaatctct actatatttg tcagcctagc gaagtgttga ttttttgcgg aggtcgtcgc    660
cctacacaag atgatcgcac tgtgggatat cgcctggtga aagtggtag cagcattcgg    720 acaccccctgc tagaacaagc ctttcacatg gatttaacca atatgattat tgagttaaag    780
```

```
gtggctaatg cttactcgaa aggaggcatt cctttacagg ttgatggggt ggcgaatatt    840
aaaattgctg gggaagaacc cacaattcat aatgcgatcg agcgtttgtt ggggaaaact    900
cgccaggaaa ttgaacgcat tgctaaagat accctggaag gaaacctgcg cggggtatta    960
gccagcctta ctcctgaaca ggttaatggg gataaattgg cttttgctaa aagtctcctc   1020
gaagaagctg aggatgactt agaacaactg gggctgattt tagatactct ccaaattcaa   1080
aatatttctg atgacgtggg atatcttgac tccatcggac gacaacaacg ggcggaattg   1140
tttagagatt ctcgtgtcgc tgaagcacaa gctaaggctg atgctgctat ccgtactgcg   1200
gaaaatcata aaatgactca gttgaaaaag ttggaaactg aggtagaggt atctaaggcg   1260
gaagctgaac gccgggtggc tgatgctatg actaaacggg cggcggtggt agcagagtcg   1320
gagtcggaaa cagcggctga ggtggctagg actcaggctg aggtctctgt tcaaaaagaa   1380
aggattaagc aggtagaaca gcaactacaa gctgatgtgg tcgcaccagc agaggcggaa   1440
tgtaaaaagg cgatcgctag ggcgcggggg gatgctgccc aaattattga agatgggaaa   1500
gcacaagctg aagggacacg acgactggct gagtcttgga aagcagccgg tagtcacccc   1560
aaccgcctta gtcggtattc cccactgggt gggcgataca cgatttcccg gaaaaattga   1620
aaaaaaattt tgtggcaggt gatatgattt gcgatcgagg tgggtaagtt agaactacag   1680
aaaacaaata acctcatttc accccgagga gaacgaatta tgagggaagc ggtgatcgcc   1740
gaagtatcga ctcaactatc agaggtagtt ggcgtcatcg agcgccatct cgaaccgacg   1800
ttgctggccg tacatttgta cggctccgca gtggatggcg gcctgaagcc acacagtgat   1860
attgatttgc tggttacggt gaccgtaagg cttgatgaaa caacgcggcg agctttgatc   1920
aacgaccttt tggaaacttc ggcttcccct ggagagagcg agattctccg cgctgtagaa   1980
gtcaccattg ttgtgcacga cgacatcatt ccgtggcgtt atccagctaa gcgcgaactg   2040
caatttggag aatggcagcg caatgacatt cttgcaggta tcttcgagcc agccacgatc   2100
gacattgatc tggctatctt gctgacaaaa gcaagagaac atagcgttgc cttggtaggt   2160
ccagcggcgg aggaactctt tgatccggtt cctgaacagg atctatttga ggcgctaaat   2220
gaaaccttaa cgctatggaa ctcgccgccc gactgggctg gcgatgagcg aaatgtagtg   2280
cttacgttgt cccgcatttg gtacagcgca gtaaccggca aaatcgcgcc gaaggatgtc   2340
gctgccgact gggcaatgga gcgcctgccg gcccagtatc agcccgtcat acttgaagct   2400
agacaggctt atcttggaca agaagaagat cgcttggcct cgcgcgcaga tcagttggaa   2460
gaatttgtcc actacgtgaa aggcgagatc accaaggtag tcggcaaata actagctggc   2520
ctggaagggt gggaaagtgt taacaactgg ttgacaatat tccgcttttc caggtcttgt   2580
cgaagtacgc ggaccgttga aggggtgaga aggaaggcga atgttgattt atgaagtttg   2640
attaacattt gtatcaaaat ataaaattct tctcataaac cctgtacaat cttttaagat   2700
ttcggaaagt gttctaggat actgaagaaa tgaaccacgg ggcaattgtt aaaagccttt   2760
gtcgatggtt cgccccggaa ggggtcttag gaggtgacac cgatggattg attgtcgtga   2820
tcattcatgg tgtgtccaat cccaactcaa ctctaagcaa gtcaacaagt aggagataaa   2880
tccatgtttg atgccttcac caaggtggtt tctcaagcta atactcgcgg cgaaatgctg   2940
agtacagctc aaatcgatgc tctgagccaa atggttgctg aaagcaacaa acgtttggat   3000
tctgttaacc gcattaccag caacgcttcc accattgttt ccaacgctgc tcgttctttg   3060
ttcgcagagc aaccccaact gattgctccc ggtggaaacg cctacaccag ccgtcgtatg   3120
```

-continued

```
gctgcttgct tgcgtgacat ggaaatcatc ctgcgctatg taacctacgc tgtgtttgct    3180
ggcgatgcaa gtgttctcga agatcgttgc ttgaacggtt tgcgtgaaac ttacctggct    3240
ttgggaactc ccggttcttc cgttgctgtc ggtgttggca aaatgaaaga agctgctctg    3300
gcgatcgtta acgatcccgc aggtatcact cctggtgatt gtagcgcttt ggcttcagaa    3360
atcgctggtt actttgaccg tgctgctgca gcagtttcct aatcaagcag atccatagca    3420
tataacaatt gaaacagttt agctgaagtc taagtgactg gacttctgtt tgttacctaa    3480
ttttttgtaa accaatcggg agataactcg agaatgaaaa ccccctaac cgaagcagtt    3540 tctatcgctg attcccaagg tcgtttccta agcagcaccg aaatccaagt agcttttggc    3600
cgttttcgtc aagccaaagc tggtctggaa gctgctaaag ctttgacctc taaagctgat    3660
agtctgatca gtggtgctgc caagcagtg tacaacaagt tcccctacac cacccaaatg    3720
cagggaccta actacgcggc agaccaacgc ggtaaggaca aatgtgctcg tgacataggc    3780
tactacctgc ggatggtaac ttattgcctg attgctggtg gaactggccc catggatgag    3840
tacctgattg ccgtgattga tgaaatcaac cggactttcg agctttctcc aagctggtac    3900
attgaagccc tgaaatacat caaagctaac cacggtttgt ctggtgacgc tgctgttgaa    3960
gctaactcct acctcgacta cgcgatcaac gccctgagct agactagtca tcgagctagc    4020
aagcttggcc ggatccggcc ggatccggag tttgtagaaa cgcaaaaagg ccatccgtca    4080
ggatggcctt ctgcttaatt tgatgcctgg cagtttatgg cgggcgtcct gcccgccacc    4140
ctccgggccg ttgcttcgca acgttcaaat ccgctcccgg cggatttgtc ctactcagga    4200
gagcgttcac cgacaaacaa cagataaaac gaaaggccca gtctttcgac tgagcctttc    4260
gttttatttg atgcctggca gttccctact ctcgactacg ggtattgatg tggcgacggc    4320
tgttcaaaat tggggcggcg gttcttctca acctcaacct acttccacag ctaaaagtct    4380
caaatcttcc cgcactaatg gtcaagctgt tcgccgcact aatggcgcag cacctaagcc    4440
agaagatact acacaaagcc tacagagcga ggttaaacaa ctacttgatc atgtcgcaca    4500
aaatactaag aataatgctg aggctgaaga ggcgatcgcc caggctttgc gacagtatcc    4560
taacctcaag cgtcgtttac agatgctttt taagtctcag ggaactcagg cgatccgaaa    4620
tatgtttaat caccctacta tctacatccc taccgctatg ctgcaaatgt ggctagaaca    4680
ggattagagc gtattccccc ccctctcgtc tagggtgggg gatctgtctc tgtaactgta    4740
tatgcacaaa atggcgtttt tgtcaataag ccgaaaaatg gaccccgctt ttaaccccaa    4800
aactcgtgca tcgccagttt tatttttgg taagataata attataaccg cgacaaaata    4860
agggttttag cctttatttt tggaaataga cacagtaagc ccttgggtgc gatttccttg    4920
agcataccat aaccccata atctcgtcaa cttttttgcga ggtatttgcc ataaaattgt    4980
attaattctt aacaatattt taaaaataaa atctatctag ccgtataaat tagtaaaatt    5040
tatgtaattt cccgattgag ggggtggggt gtggggggt ttatagtcaa attaatgtga    5100
ttggatctca tttaacctct gacgtactac ttgcatatcc tgccacatta accatttagg    5160
tttaccaaca tctcgcgagg aatttctgag taggtatgca gggtgaaaaa tcggcataca    5220
ttgacgacct tcccactgaa accactgacc gcgaatttta gtaatcgggc gtttatctcc    5280
tagaatagac ttaactgcag tcgccccagt taggaggata atttgaggat taatgaggcg    5340
gatttgttct aatagataag gcttacaggc ttgagttct gaagcggttg gggtgcgatt    5400
ttccggggga cgacagcgga tagcattaga aatataaact tcggtatctg tactcagtcc    5460
tacggagtct aaaatattat caagaagttt tccagatcta ccgacaaacg gaagaccttg    5520
```

```
ttcatcttca tgttgtcctg gtgcttctcc gataatcata atgggggcgg tggggttccc   5580
tcgaccaatc acagcatgag tgcggttttt tccaagttca cagcgcgagc acctattaca   5640
atgatcggca atttgtgcga gagtttgata ggttcccggc ggtatgggag tcttggcatt   5700
ttggggaatt tcttctaggt caaaatctac cgacttaggg gattgtaatg ggtcttgatt   5760
aacactaaga atatcgaaca ggctgagttg ttgggaattc acatacgcgg ccgcctgggc   5820
cttgagctcg aatttcctgc attaatgaat cggccaacgc gcggggagag gcggtttgcg   5880
tattgggcgc tcttccgctt cctcgctcac tgactcgctg cgctcggtcg ttcggctgcg   5940
gcgagcggta tcagctcact caaaggcggt aatacggtta tccacagaat caggggataa   6000
cgcaggaaag aacatgtgag caaaaggcca gcaaaaggcc aggaaccgta aaaatagcgg   6060
agtgtatact ggcttactat gttggcactg atgagggtgt cagtgaagtg cttcatgtgg   6120
caggagaaaa aaggctgcac cggtgcgtca gcagaatatg tgatacagga tatattccgc   6180
ttcctcgctc actgactcgc tacgctcggt cgttcgactg cggcgagcgg aaatggctta   6240
cgaacggggc ggagatttcc tggaagatgc caggaagata cttaacaggg aagtgagagg   6300
gccgcggcaa agccgttttt ccataggctc cgcccccctg acaagcatca cgaaatctga   6360
cgctcaaatc agtggtggcg aaacccgaca ggactataaa gataccaggc gtttccccct   6420
ggcggctccc tcgtgcgctc tcctgttcct gcctttcggt ttaccggtgt cattccgctg   6480
ttatggccgc gtttgtctca ttccacgcct gacactcagt tccgggtagg cagttcgctc   6540
caagctggac tgtatgcacg aaccccccat tcagtccgac cgctgcgcct tatccggtaa   6600
ctatcgtctt gagtccaacc cggaaagaca tgcaaaagca ccactggcag cagccactgg   6660
taattgattt agaggagtta gtcttgaagt catgcgccgg ttaaggctaa actgaaagga   6720
caagttttgg tgactgcgct cctccaagcc agttacctcg gttcaaagag ttggtagctc   6780
agagaacctt cgaaaaaccg ccctgcaagg cggttttttc gttttcagag caagagatta   6840
cgcgcagacc aaaacgatct caagaagatc atcttattaa gattatcaaa aaggatcttc   6900
acctagatcc ttttaaatta aaaatgaagt tttaaatcaa tctaaagtat atatgagtaa   6960
acttggtctg acagttacca atgcttaatc agtgaggcac ctatctcagc gatctgtcta   7020
tttcgttcat ccatagttgc ctgactcccc gtcgtgtaga taactacgat acgggagggc   7080
ttaccatctg gccccagtgc tgcaatgata ccgcgagacc cacgctcacc ggctccagat   7140
ttatcagcaa taaaccagcc agccggaagg gccgagcgca gaagtggtcc tgcaacttta   7200
tccgcctcca tccagtctat taattgttgc cgggaagcta gagtaagtag ttcgccagtt   7260
aatagtttgc gcaacgttgt tgccattgct acaggcatcg tggtgtcacg ctcgtcgttt   7320
ggtatggctt cattcagctc cggttcccaa cgatcaaggc gagttacatg atcccccatg   7380
ttgtgcaaaa aagcggttag ctccttcggt cctccgatcg ttgtcagaag taagttggcc   7440
gcagtgttat cactcatggt tatggcagca ctgcataatt ctcttactgt catgccatcc   7500
gtaagatgct tttctgtgac tggtgagtac tcaaccaagt cattctgaga atagtgtatg   7560
cggcgaccga gttgctcttg cccggcgtca atacgggata ataccgcgcc acatagcaga   7620
actttaaaag tgctcatcat tggaaaacgt tcttcggggc gaaaactctc aaggatctta   7680
ccgctgttga gatccagttc gatgtaaccc actcgtgcac ccaactgatc ttcagcatct   7740
tttactttca ccagcgtttc tgggtgagca aaaacaggaa ggcaaaatgc cgcaaaaaag   7800
ggaataaggg cgacacggaa atgttgaata ctcatactct tcctttttca atattattga   7860
```

-continued

```
agcatttatc agggttattg tctcatgagc ggatacatat ttgaatgtat ttagaaaaat    7920
aaacaaatag ggttccgcg cacatttccc cgaaaagtgc cacctgacgt ctaagaaacc    7980
attattatca tgacattaac ctataaaaat aggcgtatca cgaggcccttt cgtctcgcg    8040 cgtttcggtg atgacggtga aaacctctga cacatgcagc tcccggagac ggtcacagct   8100
tgtctgtaag cggatgccaa gcttgcatgc ctgcaggtgg cgcgcc                  8146
```

<210> SEQ ID NO 5
<211> LENGTH: 458
<212> TYPE: PRT
<213> ORGANISM: Acinetobacter baylii sp.

<400> SEQUENCE: 5

```
Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Gln Ile Pro
                20                  25                  30

Asp Asn Ala Pro Asp Thr Phe Ile Gln Asp Leu Val Asn Asp Ile Arg
            35                  40                  45

Ile Ser Lys Ser Ile Pro Val Pro Pro Phe Asn Asn Lys Leu Asn Gly
        50                  55                  60

Leu Phe Trp Asp Glu Asp Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Arg Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
        275                 280                 285

Pro Ala Ser Ile Arg Asn Asp Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
```

```
            325                 330                 335
Arg Met Thr Ser Asp Gln Ile Leu Asn Tyr Ser Ala Val Val Tyr Gly
        340                 345                 350

Pro Ala Gly Leu Asn Ile Ile Ser Gly Met Met Pro Lys Arg Gln Ala
    355                 360                 365

Phe Asn Leu Val Ile Ser Asn Val Pro Gly Pro Arg Glu Pro Leu Tyr
370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Ile Gln Leu Phe Glu Gly Val Ile
        435                 440                 445

Ala Lys Gln Glu Asp Ile Lys Thr Ala Asn
    450                 455

<210> SEQ ID NO 6
<211> LENGTH: 446
<212> TYPE: PRT
<213> ORGANISM: Streptomyces coelicolor

<400> SEQUENCE: 6

Met Thr Pro Asp Pro Leu Ala Pro Leu Asp Leu Ala Phe Trp Asn Ile
1               5                   10                  15

Glu Ser Ala Glu His Pro Met His Leu Gly Ala Leu Gly Val Phe Glu
            20                  25                  30

Ala Asp Ser Pro Thr Ala Gly Ala Leu Ala Ala Asp Leu Leu Ala Ala
        35                  40                  45

Arg Ala Pro Ala Val Pro Gly Leu Arg Met Arg Ile Arg Asp Thr Trp
    50                  55                  60

Gln Pro Pro Met Ala Leu Arg Arg Pro Phe Ala Phe Gly Gly Ala Thr
65                  70                  75                  80

Arg Glu Pro Asp Pro Arg Phe Asp Pro Leu Asp His Val Arg Leu His
                85                  90                  95

Ala Pro Ala Thr Asp Phe His Ala Arg Ala Gly Arg Leu Met Glu Arg
            100                 105                 110

Pro Leu Glu Arg Gly Arg Pro Trp Glu Ala His Val Leu Pro Gly
        115                 120                 125

Ala Asp Gly Gly Ser Phe Ala Val Leu Phe Lys Phe His His Ala Leu
    130                 135                 140

Ala Asp Gly Leu Arg Ala Leu Thr Leu Ala Ala Gly Val Leu Asp Pro
145                 150                 155                 160

Met Asp Leu Pro Ala Pro Arg Pro Arg Pro Glu Gln Pro Pro Arg Gly
                165                 170                 175

Leu Leu Pro Asp Val Arg Ala Leu Pro Asp Arg Leu Arg Gly Ala Leu
            180                 185                 190

Ser Asp Ala Gly Arg Ala Leu Asp Ile Gly Ala Ala Ala Leu Ser
        195                 200                 205

Thr Leu Asp Val Arg Ser Ser Pro Ala Leu Thr Ala Ala Ser Ser Gly
    210                 215                 220

Thr Arg Arg Thr Ala Gly Val Ser Val Asp Leu Asp Asp Val His His
225                 230                 235                 240
```

-continued

Val Arg Lys Thr Thr Gly Gly Thr Val Asn Asp Val Leu Ile Ala Val
            245                 250                 255

Val Ala Gly Ala Leu Arg Arg Trp Leu Asp Glu Arg Gly Asp Gly Ser
        260                 265                 270

Glu Gly Val Ala Pro Arg Ala Leu Ile Pro Val Ser Arg Arg Pro
    275                 280                 285

Arg Ser Ala His Pro Gln Gly Asn Arg Leu Ser Gly Tyr Leu Met Arg
    290                 295                 300

Leu Pro Val Gly Asp Pro Asp Pro Leu Ala Arg Leu Gly Thr Val Arg
305                 310                 315                 320

Ala Ala Met Asp Arg Asn Lys Asp Ala Gly Pro Gly Arg Gly Ala Gly
                325                 330                 335

Ala Val Ala Leu Leu Ala Asp His Val Pro Ala Leu Gly His Arg Leu
            340                 345                 350

Gly Gly Pro Leu Val Ser Gly Ala Ala Arg Leu Trp Phe Asp Leu Leu
        355                 360                 365

Val Thr Ser Val Pro Leu Pro Ser Leu Gly Leu Arg Leu Gly Gly His
    370                 375                 380

Pro Leu Thr Glu Val Tyr Pro Leu Ala Pro Leu Ala Arg Gly His Ser
385                 390                 395                 400

Leu Ala Val Ala Val Ser Thr Tyr Arg Gly Arg Val His Tyr Gly Leu
                405                 410                 415

Leu Ala Asp Ala Lys Ala Val Pro Asp Leu Asp Arg Leu Ala Val Ala
            420                 425                 430

Val Ala Glu Glu Val Glu Thr Leu Leu Thr Ala Cys Arg Pro
        435                 440                 445

<210> SEQ ID NO 7
<211> LENGTH: 457
<212> TYPE: PRT
<213> ORGANISM: Alcanivorax borkumensis

<400> SEQUENCE: 7

Met Lys Ala Leu Ser Pro Val Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Gly Pro Lys Tyr Val Ser Glu Leu Ala Gln Gln Met Arg
        35                  40                  45

Asp Tyr Cys His Pro Val Ala Pro Phe Asn Gln Arg Leu Thr Arg Arg
    50                  55                  60

Leu Gly Gln Tyr Tyr Trp Thr Arg Asp Lys Gln Phe Asp Ile Asp His
65                  70                  75                  80

His Phe Arg His Glu Ala Leu Pro Lys Pro Gly Arg Ile Arg Glu Leu
                85                  90                  95

Leu Ser Leu Val Ser Ala Glu His Ser Asn Leu Leu Asp Arg Glu Arg
            100                 105                 110

Pro Met Trp Glu Ala His Leu Ile Glu Gly Ile Arg Gly Arg Gln Phe
        115                 120                 125

Ala Leu Tyr Tyr Lys Ile His His Ser Val Met Asp Gly Ile Ser Ala
    130                 135                 140

Met Arg Ile Ala Ser Lys Thr Leu Ser Thr Asp Pro Ser Glu Arg Glu
145                 150                 155                 160

Met Ala Pro Ala Trp Ala Phe Asn Thr Lys Lys Arg Ser Arg Ser Leu
                165                 170                 175

Pro Ser Asn Pro Val Asp Met Ala Ser Ser Met Ala Arg Leu Thr Ala
            180                 185                 190

Ser Ile Ser Lys Gln Ala Ala Thr Val Pro Gly Leu Ala Arg Glu Val
        195                 200                 205

Tyr Lys Val Thr Gln Lys Ala Lys Lys Asp Glu Asn Tyr Val Ser Ile
    210                 215                 220

Phe Gln Ala Pro Asp Thr Ile Leu Asn Asn Thr Ile Thr Gly Ser Arg
225                 230                 235                 240

Arg Phe Ala Ala Gln Ser Phe Pro Leu Pro Arg Leu Lys Val Ile Ala
                245                 250                 255

Lys Ala Tyr Asn Cys Thr Ile Asn Thr Val Val Leu Ser Met Cys Gly
            260                 265                 270

His Ala Leu Arg Glu Tyr Leu Ile Ser Gln His Ala Leu Pro Asp Glu
        275                 280                 285

Pro Leu Ile Ala Met Val Pro Met Ser Leu Arg Gln Asp Asp Ser Thr
    290                 295                 300

Gly Gly Asn Gln Ile Gly Met Ile Leu Ala Asn Leu Gly Thr His Ile
305                 310                 315                 320

Cys Asp Pro Ala Asn Arg Leu Arg Val Ile His Asp Ser Val Glu Glu
                325                 330                 335

Ala Lys Ser Arg Phe Ser Gln Met Ser Pro Glu Glu Ile Leu Asn Phe
            340                 345                 350

Thr Ala Leu Thr Met Ala Pro Thr Gly Leu Asn Leu Leu Thr Gly Leu
        355                 360                 365

Ala Pro Lys Trp Arg Ala Phe Asn Val Val Ile Ser Asn Ile Pro Gly
    370                 375                 380

Pro Lys Glu Pro Leu Tyr Trp Asn Gly Ala Gln Leu Gln Gly Val Tyr
385                 390                 395                 400

Pro Val Ser Ile Ala Leu Asp Arg Ile Ala Leu Asn Ile Thr Leu Thr
                405                 410                 415

Ser Tyr Val Asp Gln Met Glu Phe Gly Leu Ile Ala Cys Arg Arg Thr
            420                 425                 430

Leu Pro Ser Met Gln Arg Leu Leu Asp Tyr Leu Glu Gln Ser Ile Arg
        435                 440                 445

Glu Leu Glu Ile Gly Ala Gly Ile Lys
    450                 455

<210> SEQ ID NO 8
<211> LENGTH: 2595
<212> TYPE: DNA
<213> ORGANISM: Artificial Sequence
<220> FEATURE:
<223> OTHER INFORMATION: Codon-optimized S. cerevisiae phosphatidate
      phosphatase (PAH1)

<400> SEQUENCE: 8
atggaattcc aatatgttgg tcgggctttg ggtagtgtta gtaaaacgtg gtcgagtatc      60
aaccccgcca ccctgagcgg cgctatcgat gtcattgtcg tggaacaccc cgatggccgg     120
ctcagttgta gccccttcca tgtgcgcttt ggtaaattcc agattctgaa acccagccaa     180
aagaaagtcc aggtctttat taacgagaaa ctgtcgaata tgcccatgaa actctcggat     240
agcggcgagg cgtacttcgt ttttgagatg ggtgatcaag tgacggatgt cccggatgaa     300
ctgctcgtct cgccggtcat gagtgccacg agtagtccgc ccaatcgcc ggaaacctcg      360 attctcgaag gcggtaccga aggcgagggc gaaggtgaga tgaaaataa gaaaaaggaa      420

```
aagaaggtgt tggaggagcc cgactttctg acattaatg acaccggtga cagcggcagc    480
aagaacagtg agacgacggg ttcgctctcg ccgaccgaaa gtagtacgac gacgccgccc    540
gatagcgtcg aggaacgcaa gttggtcgaa caacggacca agaattttca gcaaaagctg    600
aataagaaac tgaccgaaat ccatattccg agcaaattgg acaataacgg tgatttgctc    660
ctggacaccg agggttataa gccgaataaa aacatgatgc acgacacgga tattcagctg    720
aagcaattgc tcaaggatga gttcggtaac gatagcgata tttcgagctt catcaaagaa    780
gacaagaatg gcaacattaa atcgtgaac ccctatgagc atttgaccga tttgagtccc    840
ccgggtacgc ccccgaccat ggccacgagt ggcagtgtcc tgggcttgga tgcgatggag    900
agtggttcga cgctgaacag cttgagcagc agcccgagcg gcagtgacac cgaggatgag    960
acgagcttta gcaaggaaca gtcgtcgaag agtgaaaaaa cgtcgaagaa aggcaccgcg   1020
ggttcgggtg aaacggagaa acgctacatc cgcacgatcc ggctcacgaa tgatcagctg   1080
aaatgcctca acttgacgta cggtgaaaat gacttgaaat ttagtgttga ccatggcaaa   1140
gccattgtga ccagcaaatt gtttgtctgg cgctgggacg tccccatcgt tatcagcgac   1200
attgacggta cgattacgaa aagtgatgcg ctgggccacg tcctcgccat gatcggcaaa   1260
gattggaccc atctcggcgt cgctaagctg ttcagtgaga tctcgcgcaa cggttacaat   1320
atcctgtacc tgaccgcgcg ctcggccggt caggctgaca gtaccgctc gtatctccgc   1380 agtattgagc agaacggtag caagctcccg aacggccccg tcattctgag ccccgatcgg   1440
accatggctg ccctgcgccg ggaggtgatt ctgaaaaagc ccgaagtctt taaaatcgct   1500
tgcttgaacg atatccgctc gctctatttc gaagactcgg ataacgaagt ggacacggag   1560
gaaaagagca cgccgttttt cgcgggcttt ggcaatcgga tcaccgatgc gctcagctat   1620
cggacggtcg gcatcccgag tagccgcatc ttcacgatta acacggaagg cgaggtgcac   1680
atggagctgc tcgagctcgc cggttaccgg agtagctata tccatatcaa cgaactggtc   1740
gatcacttct tcccgccggt gagcctggac tcggtcgatc tgcgcacgaa cacgagcatg   1800
gtcccgggca gcccgccgaa ccgcacccctg ataactttg atagcgaaat caccagtggc   1860
cgcaagacgt tgtttcgcgg taatcaggag gaaaaattca cggacgtcaa cttttggcgc   1920
gatccgttgg tggacatcga caacctctcg gatatcagta acgatgattc ggacaatatt   1980
gatgaagaca ccgatgtgag ccaacagtcg aacatcagcc gcaaccgcgc taactcggtc   2040
aagacggcca aggtgaccaa ggctccgcag cggaatgtgt cgggcagtac gaataacaat   2100
gaagttctgg ctgcgagtag tgatgttgaa aatgccagtg acttggttag cagccactcg   2160
agtagcggct cgacccccaa caagtcgacg atgagtaagg gtgatatcgg caaacaaatc   2220
tatctggaac tgggctcgcc cttggcgagt cccaaactcc ggtatctgga cgatatggat   2280
gatgaggact cgaactataa tcgcaccaag agccgccggg ctagtagcgc cgctgctacc   2340
agcatcgaca aggagtttaa aaagctcagt gtgagtaaag ctggcgctcc cacccgcatc   2400
gttagcaaga tcaacgtgtc gaatgatgtg cacagtttgg gcaacagtga taccgaaagc   2460
cggcgggaac agagcgtcaa tgaaaccggt cgcaatcagt tgccgcacaa tagtatggat   2520
gataaggatt tggattcgcg ggtgagtgac gagttcgatg acgatgagtt tgatgaagat   2580
gagtttgagg attag                                                   2595
```

<210> SEQ ID NO 9
<211> LENGTH: 6936
<212> TYPE: DNA

<213> ORGANISM: Triticum aestivum

<400> SEQUENCE: 9

| | | | | | |
|---|---|---|---|---|---|
| atgggatcca | cacatttgcc | cattgtcggc | cttaatgcct | cgacaacacc | atcgctatcc | 60 |
| actattcgcc | cggtaaattc | agccggtgct | gcattccaac | catctgcccc | ttctagaacc | 120 |
| tccaagaaga | aaagtcgtcg | tgttcagtca | ttaagggatg | gaggcgatgg | aggcgtgtca | 180 |
| gaccctaacc | agtctattcg | ccaaggtctt | gccggcatca | ttgacctccc | aaaggagggc | 240 |
| acatcagctc | cggaagtgga | tatttcacat | gggtccgaag | aacccagggg | ctcctaccaa | 300 |
| atgaatggga | tactgaatga | agcacataat | gggaggcatg | cttcgctgtc | taaggttgtc | 360 |
| gaattttgta | tggcattggg | cggcaaaaca | ccaattcaca | gtgtattagt | tgcgaacaat | 420 |
| ggaagggcag | cagctaagtt | catgcggagt | gtccgaacat | gggctaatga | aacatttggg | 480 |
| tcagagaagg | caattcagtt | gatagctatg | gctactccag | aagacatgag | gataaatgca | 540 |
| gagcacatta | gaattgctga | tcaatttgtt | gaagtacccg | gtggaacaaa | caataacaac | 600 |
| tatgcaaatg | tccaactcat | agtggagata | gcagtgagaa | ccggtgtttc | tgctgtttgg | 660 |
| cctggttggg | gccatgcatc | tgagaatcct | gaacttccag | atgcactaaa | tgcaaacgga | 720 |
| attgtttttc | ttgggccacc | atcatcatca | atgaacgcac | taggtgacaa | ggttggttca | 780 |
| gctctcattg | ctcaagcagc | aggggttccg | actcttcctt | ggggtggatc | acaggtggaa | 840 |
| attccattag | aagtttgttt | ggactcgata | cctgcggaga | tgtataggaa | gcttgtgtt | 900 |
| agtactacgg | aggaagcact | tgcgagttgt | cagatgattg | ggtatccagc | catgattaaa | 960 |
| gcatcatggg | gtggtggtgg | taaagggatc | cgaaaggtta | taacgacga | tgatgtcaga | 1020 |
| gcactgttta | agcaagtgca | aggtgaagtt | cctggctccc | caatatttat | catgagactt | 1080 |
| gcatctcaga | gtcgacatct | tgaagttcag | ttgctttgtg | atcaatatgg | caatgtagct | 1140 |
| gcgcttcaca | gtcgtgactg | cagtgtgcaa | cggcgacacc | aaaagattat | tgaggaagga | 1200 |
| ccagttactg | ttgctcctcg | cgagacagtg | aaagagctag | agcaagcagc | aaggaggctt | 1260 |
| gctaaggctg | tgggttatgt | tggtgctgct | actgttgaat | atctctacag | catggagact | 1320 |
| ggtgaatact | attttctgga | acttaatcca | cggttgcagg | ttgagcatcc | agtcaccgag | 1380 |
| tggatagctg | aagtaaactt | gcctgcagct | caagttgcag | ttggaatggg | tatcccctt | 1440 |
| tggcaggttc | cagagatcag | acgtttctat | ggaatggaca | atggaggagg | ctatgacatt | 1500 |
| tggagggaaa | cagcagctct | tgctactcca | tttaacttcg | atgaagtgga | ttctcaatgg | 1560 |
| ccaaagggtc | attgtgtagc | agttaggata | accagtgagg | atccagatga | cggattcaag | 1620 |
| cctaccggtg | gaaaagtaaa | ggagatcagt | tttaaaagca | agccaaatgt | ttgggcctat | 1680 |
| ttctctgtta | agtccggtgg | aggcattcat | gaatttgctg | attctcagtt | tggacatgtt | 1740 |
| tttgcatatg | gagtgtctag | agcagcagca | ataaccaaca | tgtctcttgc | gctaaaagag | 1800 |
| attcaaattc | gtggagaaat | tcattcaaat | gttgattaca | cagttgatct | cttgaatgcc | 1860 |
| tcagacttca | agaaaacag | gattcatact | ggctggctgg | ataacagaat | agcaatgcga | 1920 |
| gtccaagctg | agagacctcc | gtggtatatt | tcagtggttg | gaggagctct | atataaaaca | 1980 |
| ataacgagca | acacagacac | tgtttctgaa | tatgttagct | atctcgtcaa | gggtcagatt | 2040 |
| ccaccgaagc | atatatccct | tgtccattca | actgtttctt | tgaatataga | ggaaagcaaa | 2100 |
| tatacaattg | aaactataag | gagcggacag | ggtagctaca | gattgcgaat | gaatggatca | 2160 |
| gttattgaag | caaatgtcca | aacattatgt | gatggtggac | ttttaatgca | gttggatgga | 2220 |
| aacagccatg | taatttatgc | tgaagaagag | gccggtggta | cacggcttct | aattgatgga | 2280 |

```
aagacatact tgttacagaa tgatcacgat ccttcaaggt tattagctga gacaccctgc    2340
aaacttcttc gtttcttggt tgccgatggt gctcatgttg aagctgatgt accatatgcg    2400
gaagttgagg ttatgaagat gtgcatgccc ctcttgtcac ctgctgctgg tgtcattaat    2460
gttttgttgt ctgagggcca gcctatgcag gctggtgatc ttatagcaag acttgatctt    2520
gatgacccct ctgctgtgaa gagagctgag ccatttaacg gatctttccc agaaatgagc    2580
cttcctattg ctgcttctgg ccaagttcac aaaagatgtg ccacaagctt gaatgctgct    2640
cggatggtcc ttgcaggata tgatcacccg atcaacaaag ttgtacaaga tctggtatcc    2700
tgtctagatg ctcctgagct tccttttccta caatgggaag agcttatgtc tgttttagca    2760
actagacttc caaggcttct taagagcgag ttggagggta aatacagtga atataagtta    2820
aatgttggcc atgggaagag caaggatttc ccttccaaga tgctaagaga gataatcgag    2880
gaaaatcttg cacatggttc tgagaaggaa attgctacaa atgagaggct tgttgagcct    2940
cttatgagcc tactgaagtc atatgagggt ggcagagaaa gccatgcaca ctttattgtg    3000
aagtcccttt tcgaggacta tctctcggtt gaggaactat tcagtgatgg cattcagtct    3060
gatgtgattg aacgcctgcg ccaacaacat agtaaagatc tccagaaggt tgtagacatt    3120
gtgttgtctc accagggtgt gagaaacaaa actaagctga tactaacact catggagaaa    3180
ctggtctatc caaaccctgc tgtctacaag gatcagttga ctcgcttttc ctccctcaat    3240
cacaaaagat attataagtt ggcccttaaa gctagcgagc ttcttgaaca aaccaagctt    3300
agtgagctcc gcacaagcat tgcaaggagc ctttcagaac ttgagatgtt tactgaagaa    3360
aggacggcca ttagtgagat catgggagat ttagtgactg ccccactgcc agttgaagat    3420
gcactggttt ctttgtttga ttgtagtgat caaactcttc agcagagggt gatcgagacg    3480
tacatatctc gattatacca gcctcatctt gtcaaggata gtatccagct gaaatatcag    3540
gaatctggtg ttattgcttt atgggaattc gctgaagcgc attcagagaa gagattgggt    3600
gctatggtta ttgtgaagtc gttagaatct gtatcagcag caattggagc tgcactaaag    3660
ggtacatcac gctatgcaag ctctgagggt aacataatgc atattgcttt attgggtgct    3720
gataatcaaa tgcatggaac tgaagacagt ggtgataacg atcaagctca agtcaggata    3780
gacaaacttt ctgcgacact ggaacaaaat actgtcacag ctgatctccg tgctgctggt    3840
gtgaaggtta ttagttgcat tgttcaaagg gatggagcac tcatgcctat gcgccatacc    3900
ttcctcttgt cggatgaaaa gctttgttat ggggaagagc cggttctccg gcatgtggag    3960
cctcctcttt ctgctcttct tgagttgggt aagttgaaag tgaaaggata caatgaggtg    4020
aagtatacac cgtcacgtga tcgtcagtgg aacatataca cacttagaaa tacagagaac    4080
cccaaaatgt tgcacagggt gttttttccga actcttgtca ggcaacccgg tgcttccaac    4140
aaattcacat caggcaacat cagtgatgtt gaagtgggag gagctgagga atctctttca    4200
tttacatcga gcagcatatt aagatcgctg atgactgcta tagaagagtt ggagcttcac    4260
gcgattagga caggtcactc tcatatgttt ttgtgcatat tgaaagagcg aaagcttctt    4320
gatcttgttc ccgtttcagg gaacaaagtt gtggatattg ccaagatgaa agctactgca    4380
tgcttgcttc tgaaagaaat ggctctacag atacatgaac ttgtgggtgc aaggatgcat    4440
catctttctg tatgccaatg ggaggtgaaa cttaagttgg acagcgatgg gcctgccagt    4500
ggtacctgga gagttgtaac aaccaatgtt actagtcaca cctgcactgt ggatatctac    4560
cgtgaggttg aagatacaga atcacagaaa ctagtatacc actctgctcc atcgtcatct    4620
```

```
ggtcctttgc atggcgttgc actgaatact ccatatcagc ctttgagtgt tattgatctg    4680
aaacgttgct ccgctagaaa caacagaact acatactgct atgattttcc gttggcattt    4740
gaaactgcag tgcagaagtc atggtctaac atttctagtg acaataaccg atgttatgtt    4800
aaagcaacgg agctggtgtt tgctcacaag aatgggtcat ggggcactcc tgtaattcct    4860
atggagcgtc ctgctgggct caatgacatt ggtatggtag cttggatctt ggacatgtcc    4920
actcctgaat atcccaatgg caggcagatt gttgtcatcg caaatgatat tacttttaga    4980
gctggatcgt ttggtccaag ggaagatgca ttttttgaaa ctgttaccaa cctagcttgt    5040
gagaggaggc ttcctctcat ctacttggca gcaaactctg gtgctcggat cggcatagca    5100
gatgaagtaa atcttgctt ccgtgttgga tggtctgatg atggcagccc tgaacgtggg    5160
tttcaatata tttatctgac tgaagaagac catgctcgta ttagcgcttc tgttatagcg    5220
cacaagatgc agcttgataa tggtgaaatt aggtgggtta ttgattctgt tgtagggaag    5280
gaggatgggc taggtgtgga gaacatacat ggaagtgctg ctattgccag tgcctattct    5340
agggcctatg aggagacatt tacgcttaca tttgtgactg gaaggactgt tggaatagga    5400
gcatatcttg ctcgacttgg catacggtgc attcagcgta ctgaccagcc cattatccta    5460
actgggtttt ctgccttgaa caagcttctt ggccgggaag tgtacagctc ccacatgcag    5520
ttgggtggcc ccaaaattat ggcgacaaac ggtgttgtcc atctgacagt ttcagatgac    5580
cttgaaggtg tatctaatat attgaggtgg ctcagctatg ttcctgccaa cattggtgga    5640
cctcttccta ttacaaaatc tttggaccca cctgacagac ccgttgctta catccctgag    5700
aatacatgcg atcctcgtgc tgccatcagt ggcattgatg atagccaagg gaaatggttg    5760
gggggcatgt tcgacaaaga cagttttgtg agacatttg aaggatgggc gaagtcagtt    5820
gttactggca gagcgaaact cggagggatt ccggtgggtg ttatagctgt ggagacacag    5880
actatgatgc agctcatccc tgctgatcca ggccagcttg attcccatga gcgatctgtt    5940
cctcgtgctg gcaagtctg gtttccagat tcagctacta agacagcgca ggcaatgctg    6000
gacttcaacc gtgaaggatt acctctgttc atccttgcta actggagagg cttctctggt    6060
ggacaaagag atcttttga aggaatcctt caggctgggt caacaattgt tgagaacctt    6120
agggcataca atcagcctgc ctttgtatat atccccaagg ctgcagagct acgtggaggg    6180
gcttgggtcg tgattgatag caagataaat ccagatcgca ttgagttcta tgctgagagg    6240
actgcaaagg gcaatgttct cgaacctcaa gggttgatcg agatcaagtt caggtcagag    6300
gaactccaag agtgcatggg taggcttgat ccagaattga taaatctgaa ggcaaagctc    6360
cagggagtaa agcatgaaaa tggaagtcta cctgagtcag aatcccttca gaagagcata    6420
gaagcccgga agaaacagtt gttgcctttg tatactcaaa ttgcggtacg gttcgctgaa    6480
ttgcatgaca cttcccttag aatggctgct aagggtgtga ttaagaaggt tgtagactgg    6540
gaagattcta ggtcgttctt ctacaagaga ttacggagga ggatatccga ggatgttctt    6600
gcgaaggaaa ttagaggtgt aagtggcaag cagttttctc accaatcggc aatcgagctg    6660
atccagaaat ggtacttggc ctctaaggga gctgaaacag gaagcactga atgggatgat    6720
gacgatgctt ttgttgcctg gagggaaaac cctgaaaact accaggagta tatcaaagaa    6780
cccagggctc aaagggtatc tcagttgctc tcagatgttg cagactccag tccagatcta    6840
gaagccttgc cacagggtct ttctatgcta ctagagaaga tggatcctgc aaagagggaa    6900
attgttgaag actttgaaat aaaccttgta aagtaa                              6936
```

<210> SEQ ID NO 10
<211> LENGTH: 996
<212> TYPE: DNA
<213> ORGANISM: Synechococcus PCC7942

<400> SEQUENCE: 10

```
atgtcagagg ctcaaacgcc cctgacagta ccgaagaagt tcttggtgc tccaggaggc      60
ttcaaccca ccgtcgcact cttcttggca ggttatacct gcgcggcgct ctcagttttg     120
gggtactggt gctggagttg gccccactgg ctatctttcc ttctgagtgt cacagcctta    180
catttggtag gcaccgtcat tcacgatgcc tctcataatg tggctcacgc agtcgcatt    240
ctgaatgcga ttttgggaca tggcagtgca ctattgctgg gctttacttt tccggtgttt    300
acgcgggttc acctgcaaca tcacgcccac gtcaacgatc caagaacga tcccgaccac    360
atcgttttcca cctttgggcc gctgtggttg atcgcaccgc gcttcttcta tcacgagatc    420
tatttcttcc agcgccgcct ttggaagaaa tttgaattac tcgaatggtt cctcagtcgc    480
gctgtggtca tcggcatctt tgcctgcggc gtcaagtttg gcttcctggg cttcctgatg    540
aactactggc tggctccagc cttggtcgtt ggcattgccc taggactctt cttcgactat    600
ttaccccacc gccccttcca agagcgcaac cgctggcgca atgcacgggt ctatcccggt    660
caggtgatga acatcctgat catgggtcag aactatcacc tgatccatca cctctggcca    720
tcgatcccct ggtatctcta ccgaccggcc taccacgcta ccaagccgtt gttggaccta    780
cgccagtcgc cgcaaacgct cgggattctc tccagcaaaa aagatttctg gaactttatc    840
tacgacgttt tcatcggcat ccgcattcac caatcgcacg aggctgagcc gcagagctcc    900
gtcgttcctg aaacgaagtc gagtgaatca gccgttctcg caaaagctcc gatgtctgcc    960
acagaagact ctcgtgagcc agccttgacg aagtag                              996
```

<210> SEQ ID NO 11
<211> LENGTH: 486
<212> TYPE: DNA
<213> ORGANISM: Brevundimonas sp. SD212

<400> SEQUENCE: 11

```
atggcctggc tgacgtggat cgcgctgttc ctgaccgcct ttttgggcat ggaggcgttc      60
gcctggatca tgcaccgcta tgtgatgcac ggtttcctgt ggtcctggca ccgcagccat    120
catgagccgc acgatcaccc cctggagaag aacgacctgt cgccgtggt cttcgccgcc    180
ccggccatcg tcatggtggc cgtgggtctg cacctgtggc cctgggccct gccggtcggc    240
ctggggatca cggcctatgg gatggtctat ttcttcttcc acgacggcct ggtgcaccgg    300
cggttcccga cgggcttttc cgggcggtcc ggcttctgga cgcggcgcat ccaggcgcac    360
cgtctgcatc acgccgtgcg cacgcgcgaa ggctgcgtct ccttcggctt tctgtgggtg    420
cggtcggcgc gggcgctgaa ggccgaactg gctcagaagc ggggctcttc cagcagcggc    480
gcctga                                                              486
```

<210> SEQ ID NO 12
<211> LENGTH: 735
<212> TYPE: DNA
<213> ORGANISM: Brevundimonas sp. SD212

<400> SEQUENCE: 12

```
atgaccgccg ccgtcgccga gccccgcatc gtcccgcgcc agacctggat cggtctgacc      60
ctggcgggaa tgatcgtggc gggatggggg agcctgcacg tctacggcgt ctatttcac     120
```

```
cgctggggca cctccagtct ggtgatcgtc ccggcgatcg tagcggtcca gacctggttg    180
tcggtcggcc ttttcatcgt cgcccatgac gccatgcacg gctccctggc gccgggacgg    240
ccgcggctga acgccgcagt cggccggctg accctggggc tctatgcggg cttccgcttc    300
gatcggctga agacggcgca ccacgcccac cacgccgcgc ccggcacggc cgacgacccg    360
gacttttacg ccccggcgcc ccgcgccttc cttccctggt tcctgaactt cttttcgcacc   420 tatttcggct ggcgcgagat ggcggtcctg accgccctgg tcctgatcgc cctcttcggc    480
ctgggggcgc ggccggccaa tctcctgacc ttctgggccg cgccggccct gctttcagcg    540
cttcagctct tcaccttcgg cacctggctg ccgcaccgcc acaccgacca gccgttcgcc    600
gacgcccacc acgcccgcag cagcggctac ggccccgttc tttccctgct cacctgcttc    660
cacttcggcc gccaccacga acaccacctc accccctggc ggccctggtg gcgtttgtgg    720
cgcggcgagt cttga                                                    735

<210> SEQ ID NO 13
<211> LENGTH: 23
<212> TYPE: DNA
<213> ORGANISM: Artificial Sequence
<220> FEATURE:
<223> OTHER INFORMATION: primer to A. plantensis genome outside of
      homology arm

<400> SEQUENCE: 13
actactaatg tggctttcca ggg                                            23

<210> SEQ ID NO 14
<211> LENGTH: 22
<212> TYPE: DNA
<213> ORGANISM: Artificial Sequence
<220> FEATURE:
<223> OTHER INFORMATION: primer to A. plantensis outside of the homology
      arm

<400> SEQUENCE: 14
gtaaattagc gcgatgggtt tg                                             22

<210> SEQ ID NO 15
<211> LENGTH: 21
<212> TYPE: DNA
<213> ORGANISM: Artificial Sequence
<220> FEATURE:
<223> OTHER INFORMATION: primer to homology arm upstream of pilA gene

<400> SEQUENCE: 15
gttggagcaa tggcacgagt c                                              21

<210> SEQ ID NO 16
<211> LENGTH: 23
<212> TYPE: DNA
<213> ORGANISM: Artificial Sequence
<220> FEATURE:
<223> OTHER INFORMATION: primer to upstream end of aadA gene

<400> SEQUENCE: 16
atgacgccaa ctacctctga tag                                            23

<210> SEQ ID NO 17
<211> LENGTH: 22
<212> TYPE: DNA
<213> ORGANISM: Artificial Sequence
<220> FEATURE:
<223> OTHER INFORMATION: primer to downstream end of aadA gene
```

<400> SEQUENCE: 17
gtatcagccc gtcatacttg aa                                          22

<210> SEQ ID NO 18
<211> LENGTH: 22
<212> TYPE: DNA
<213> ORGANISM: Artificial Sequence
<220> FEATURE:
<223> OTHER INFORMATION: primer to pilA gene

<400> SEQUENCE: 18
gacggtggtt tcaccttaat cg                                          22

<210> SEQ ID NO 19
<211> LENGTH: 22
<212> TYPE: DNA
<213> ORGANISM: Artificial Sequence
<220> FEATURE:
<223> OTHER INFORMATION: primer to pilA gene

<400> SEQUENCE: 19
tgctgtagta cctacccaga cc                                          22

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cataccctgc tgtgtggcaa                                             20

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
cgggtgatat ctttggtggt g                                           21

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
gtacaaatgt acggccagca ac                                          22

<210> SEQ ID NO 23
<211> LENGTH: 528
<212> TYPE: DNA
<213> ORGANISM: Artificial Sequence
<220> FEATURE:
<223> OTHER INFORMATION: codon-optomized Pantoea ananatis beta-carotene
      3,3'-hydroxylase (crtZ)

<400> SEQUENCE: 23
atgctgtgga tttggaacgc gctgatcgtg tttgtcacag tcatcgggat ggaagttatt       60
gccgccttgg cacacaaata catcatgcac ggctggggct ggggatggca tctgtctcac      120

```
cacgaacccc gcaaaggcgc tttcgaagtc aatgatctgt atgctgtcgt gtttgcagcc    180
ctgagcattt tgctcatcta cctgggctcg accggtatgt ggccgttgca atggattggt    240
gccggcatga ccgcctacgg tctgctgtat tcatggtgc acgatggcct ggtccatcaa     300
cggtggcctt tcggtatat tccccgaaag ggctacctga agcgcctata tatggcccat     360
cgaatgcatc acgcagtccg ggggaaggaa gggtgtgtga gttttgggtt tctatatgct    420 ccccccgttgt cgaaactgca agcaaccctg cgtgagcgtc atggcgctcg cgctggggcg    480
gcgcgggacg cgcaaggggg cgaagatgaa ccggcatcgg ggaaataa                 528
```

```
<210> SEQ ID NO 24
<211> LENGTH: 720
<212> TYPE: DNA
<213> ORGANISM: Artificial Sequence
<220> FEATURE:
<223> OTHER INFORMATION: codon-optomized Brevundimonas sp. SD212
      beta-carotene 4,4'-ketolase (crtW)

<400> SEQUENCE: 24
```

```
atgacggctg cggtcgctga gccgcgaatc gtgcctcgtc aaacctggat cgggctcaca    60
cttgcaggga tgattgtggc aggctggggg agtcttcacg tctatggagt ctactttcat    120
cgctggggga caagtagcct cgttattgtg ccagcaatcg tggctgtcca gacctggctc    180
agtgtgggcc tattcattgt cgcacacgac gctatgcacg gtcgctggc gccgggtcgg    240 cctcgcctaa acgcagccgt aggcagactc accttagggc tctatgccgg tttccgattt    300
gatcgcctta aaacggccca ccacgcacat cacgccgccc ccggtactgc cgatgacccc    360
gatttctacg ccccagcacc gcgagcgttt ttgccttggt tcctcaactt ctttcgcact    420
tactttggct ggcgtgagat ggctgttctg acagctttag tcctaatagc cttgtttggt    480
ttgggtgccc ggccggcaaa tcttctcacg ttctgggcag ctccggcgct gttaagtgct    540
ctacagctat tcacttttgg cacgtggctg ccgcaccgcc acactgatca gccttttgcg    600
gacgcccacc atgctcggtc ttccggttac ggcccggtgc tcagcctgct acctgttttt    660
cactttggtc ggcaccacga acaccatctg acaccgtggc gcccctggtg gcggctatgg    720
```

```
<210> SEQ ID NO 25
<211> LENGTH: 489
<212> TYPE: DNA
<213> ORGANISM: Athrospira plantensis

<400> SEQUENCE: 25
```

```
atgaaaaccc ccctaaccga agcagtttct atcgctgatt cccaaggtcg tttcctaagc    60
agcaccgaaa tccaagtagc ttttggccgt tttcgtcaag ccaaagctgg tctgaaagct    120
gctaaagctt tgacctctaa agctgatagt ctgatcagtg gtgctgccca agcagtgtac    180
aacaagttcc cctacaccac ccaaaatgcag ggacctaact acgcggcaga ccaacgcggt    240
aaggacaaat gtgctcgtga cataggctac tacctgcgga tggtaactta ttgcctgatt    300
gctggtggaa ctggccccat ggatgagtac ctgattgccg gtattgatga aatcaaccgg    360
actttcgagc tttctccaag ctggtacatt gaagccctga atacatcaa agctaaccac    420 ggtttgtctg gtgacgctgc tgttgaagct aactcctacc tcgactacgc gatcaacgcc    480
ctgagctag                                                            489
```

```
<210> SEQ ID NO 26
<211> LENGTH: 519
```

```
<212> TYPE: DNA
<213> ORGANISM: Athroisma gracile

<400> SEQUENCE: 26
atgtttgatg ccttcaccaa ggtggtttct caagctgata ctcgcggcga aatgctgagt     60
acagctcaaa tcgatgctct gagccaaatg gttgctgaaa gcaacaaacg tttggattct    120
gttaaccgca ttaccagcaa cgcttccacc attgtttcca acgctgctcg ttctttgttc    180
gcagagcaac cccaactgat tgctcccggt ggaaacgcct acaccagccg tcgtatggct    240
gcttgcttgc gtgacatgga atcatcctg cgctatgtaa cctacgctgt gtttgctggc    300
gatgcaagtg ttctcgaaga tcgttgcttg aacggtttgc gtgaaactta cctggctttg    360
ggaactcccg ttcttccgt tgctgtcggt gttggcaaaa tgaaagaagc tgctctggcg    420
atcgttaacg atcccgcagg tatcactcct ggtgattgta gcgctttggc ttcagaaatc    480
gctggttact ttgaccgtgc tgctgcagca gtttcctaa                           519

<210> SEQ ID NO 27
<211> LENGTH: 1406
<212> TYPE: DNA
<213> ORGANISM: Athrospira plantensis

<400> SEQUENCE: 27 ttgaagggt gagaaggaag gcgaatgttg atttatgaag tttgattaac atttgtatca     60
aaatataaaa ttcttctcat aaaccctgta caatctttta agatttcgga agtgttcta    120
ggatactgaa gaaatgaacc acggggcaat tgttaaaagc ctttgtcgat ggttcgcccc    180
ggaagggtc ttaggaggtg acaccgatgg attgattgtc gtgatcattc atggtgtgtc    240
caatcccaac tcaactctaa gcaagtcaac aagtaggaga taaatccatg tttgatgcct    300
tcaccaaggt ggtttctcaa gctgatactc gcggcgaaat gctgagtaca gctcaaatcg    360
atgctctgag ccaaatggtt gctgaaagca caaacgtttt ggattctgtt aaccgcatta    420
ccagcaacgc ttccaccatt gtttccaacg ctgctcgttc tttgttcgca gagcaacccc    480
aactgattgc tcccggtgga aacgcctaca ccagccgtcg tatggctgct tgcttgcgtg    540
acatggaaat catcctgcgc tatgtaacct acgctgtgtt tgctggcgat gcaagtgttc    600
tcgaagatcg ttgcttgaac ggtttgcgtg aaacttacct ggctttggga actcccggtt    660
cttccgttgc tgtcggtgtt ggcaaaatga agaagctgc tctggcgatc gttaacgatc    720
ccgcaggtat cactcctggt gattgtagcg ctttggcttc agaaatcgct ggttactttg    780
accgtgctgc tgcagcagtt cctaatcaa gcagatccat agcatataac aattgaaaca    840
gtttagctga agtctaagtg actggacttc tgtttgttac ctaattttttt gtaaaccaat    900
cgggagataa ctcgagaatg aaaaccccccc taaccgaagc agtttctatc gctgattccc    960
aaggtcgttt cctaagcagc accgaaatcc aagtagcttt tggccgtttt cgtcaagcca   1020
aagctggtct ggaagctgct aaagctttga cctctaaagc tgatagtctg atcagtggtg   1080
ctgcccaagc agtgtacaac aagttcccct acaccaccca aatgcaggga cctaactacg   1140
cggcagacca acgcggtaag gacaaatgtg ctcgtgacat aggctactac ctgcggatgg   1200
taacttattg cctgattgct ggtggaactg gccccatgga tgagtacctg attgccggta   1260
ttgatgaaat caaccggact ttcgagcttt tccaagctg gtacattgaa gccctgaaat   1320
acatcaaagc taaccacggt ttgtctggtg acgtgctgt tgaagctaac tcctacctcg   1380
actacgcgat caacgccctg agctag                                         1406
```